(12) United States Patent
Taga et al.

(10) Patent No.: US 8,569,454 B2
(45) Date of Patent: Oct. 29, 2013

(54) YS68 POLYPEPTIDE INVOLVED IN PRIMITIVE HEMATOPOIESIS

(75) Inventors: Tetsuya Taga, Kumamoto (JP); Naoki Kimura, Ibaraki (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/837,241

(22) Filed: Jul. 15, 2010

(65) Prior Publication Data

US 2010/0304401 A1 Dec. 2, 2010

Related U.S. Application Data

(60) Division of application No. 11/643,069, filed on Dec. 20, 2006, now Pat. No. 7,794,973, which is a continuation of application No. 10/118,513, filed on Apr. 8, 2002, now abandoned, which is a continuation-in-part of application No. PCT/JP00/05756, filed on Aug. 25, 2000.

(30) Foreign Application Priority Data

Oct. 8, 1999 (JP) .................................... 11-288738
Oct. 8, 1999 (JP) .................................... 11-288739
Apr. 19, 2000 (JP) ................................ 2000-123721

(51) Int. Cl.
*C07K 14/475* (2006.01)

(52) U.S. Cl.
USPC ........................... 530/350; 530/838; 530/402

(58) Field of Classification Search
None
See application file for complete search history.

(56) References Cited

FOREIGN PATENT DOCUMENTS

WO    WO 00/78954 A2    12/2000

OTHER PUBLICATIONS

Bowie et al., "Deciphering the Message in Protein Sequences: Tolerance to Amino Acid Substitutions," Science, vol. 247, pp. 1306-1310 (1990).
Promega, "Protocols and Applications Guide," Catalogue (1989/1990).
Chui et al., "cDNA cloning of murine Nrf 2 gene, coding for a p45 NF-E2 related transcription factor," Biochem. Biophys. Res. Comm. vol. 209, pp. 40-46 (1995).
EMBL Accession No. AL080144, dated Jun. 23, 1999.
EMBL Accession No. AC009487, dated Aug. 25, 1999.
Guimaraes et al., "A new approach to the study of haematopoietic development in the yolk sac and embryoid bodies," Development, vol. 121, pp. 3335-3346 (1995).
International Search Report, International Application No. PCT/JP00/05756, mailed Nov. 14, 2000.
Iwama et al., "Molecular cloning and characterization of mouse Tie and Tek receptor tyrosine kinase genes and their expression in hematopoietic stem cells," Biochem. Biophys. Res. Comm. vol. 195, pp. 301-309 (1993).
Kimura, et al. , "Searching for novel genes involved in early hematopoiesis in mice", Seikagku vol. 71(8), p. 1038 (1999) (Translation of Japanese Reference).
Kimura, et al., "Identification of a novel transcription factor, ELYS, expressed predominantly in mouse foetal haematopoietic tissues", Genes to Cells, vol. 7(4), pp. 435-446 (2002).
Larsson-BlomBerg et al., "Isolation of tyrosine kinase related genes expressed in the early hematopoietic system", FEBS Letters, vol. 348(2), pp. 119-125 (1994).
Malhotra et al., "Identification of differentially expressed mRNAs in human fetal liver across gestation," Nucleic Acids Research, vol. 27, No. 3, pp. 839-847 (1999).
Palis et al., "Differential Gene Expression During Early Murine Yolk Sac Development," Molecular Reproduction and Development, vol. 42, pp. 19-27 (1995).
Rudinger, in "Peptide Hormones" (ed., J.A. Parsons) University Park Press, Baltimore, pp. 1-7 (1976).
Sato, et al. "Involvement of Stromal Membrane-Associated Protein (SMAP-1) in Erythorpoietic Microenvironment", The Journal of Biochemistry, vol. 124(1), pp. 209-216 (1998).
Waterston, GenBank/EMBL Accession No. AC009487.3 (Aug. 24, 1999), human BAC clone RP11-334E15.
Wambutt et al., GenBank/EMBL Accession No. T12528 (Jul. 23, 1999), human clone DKFZp434N093.1.
Wambutt et al., GenBank/EMBL Accession No. AL080144 (Jun. 23, 1999), human clone DKFZp434N093.
EP, Supplementary Partial European Search Report, European Application No. 00955032.8, mailed Mar. 4, 2003.
Restriction Requirement, U.S. Appl. No. 10/118,513, mailed Sep. 21, 2005 (7 pages).
Fish & Richardson P.C., Response to Restriction Requirement, U.S. Appl. No. 10/118,513, filed Mar. 20, 2006 (3 pages).
Non-final Office Action, U.S. Appl. No. 10/118,513, mailed Jun. 20, 2006 (12 pages).
Fish & Richardson P.C., Preliminary Amendment in U.S. Appl. No. 11/643,069, filed Dec. 20, 2006 (3 pages).
Fish & Richardson P.C., Preliminary Amendment in U.S. Appl. No. 11/643,069, filed Nov. 21, 2007 (8 pages).
Office Action in U.S. Appl. No. 11/643,069, mailed Mar. 20, 2009 (14 pages).
Fish & Richardson P.C., Response to Office Action in U.S. Appl. No. 11/643,069, mailed Mar. 20, 2009, filed Jul. 9, 2009 (33 pages).
Final Office Action in U.S. Appl. No. 11/643,069, mailed Oct. 19, 2009 (8 pages).

(Continued)

Primary Examiner — Robert C Hayes
(74) Attorney, Agent, or Firm — Fish & Richardson P.C.

(57) ABSTRACT

A novel gene, dubbed "YS68", involved in primitive hematopoiesis was successfully isolated from cDNA derived from mouse yolk sacs. In addition, a human gene corresponding to this gene was successfully isolated. Expression characteristics of these genes suggested their involvement in primitive hematopoiesis. The proteins of this invention and genes encoding the proteins may be utilized as tools for drug development against diseases, such as hematological disorders.

13 Claims, 13 Drawing Sheets

(56) References Cited

OTHER PUBLICATIONS

Fish & Richardson P.C., Response to Final Office Action in U.S. Appl. No. 11/643,069, mailed Oct. 19, 2009, filed Feb. 17, 2010 (6 pages).

Notice of Allowance in U.S. Appl. No. 11/643,069, mailed Apr. 19, 2010 (5 pages).

Rasala et al., "ELYS is a dual nucleoporin/kinetochore protein required for nuclear pore assembly and proper cell division," Proc. Natl. Acad. Sci. USA, vol. 103(47), Nov. 21, 2006, pp. 17801-17806 (epub Nov. 10, 2006).

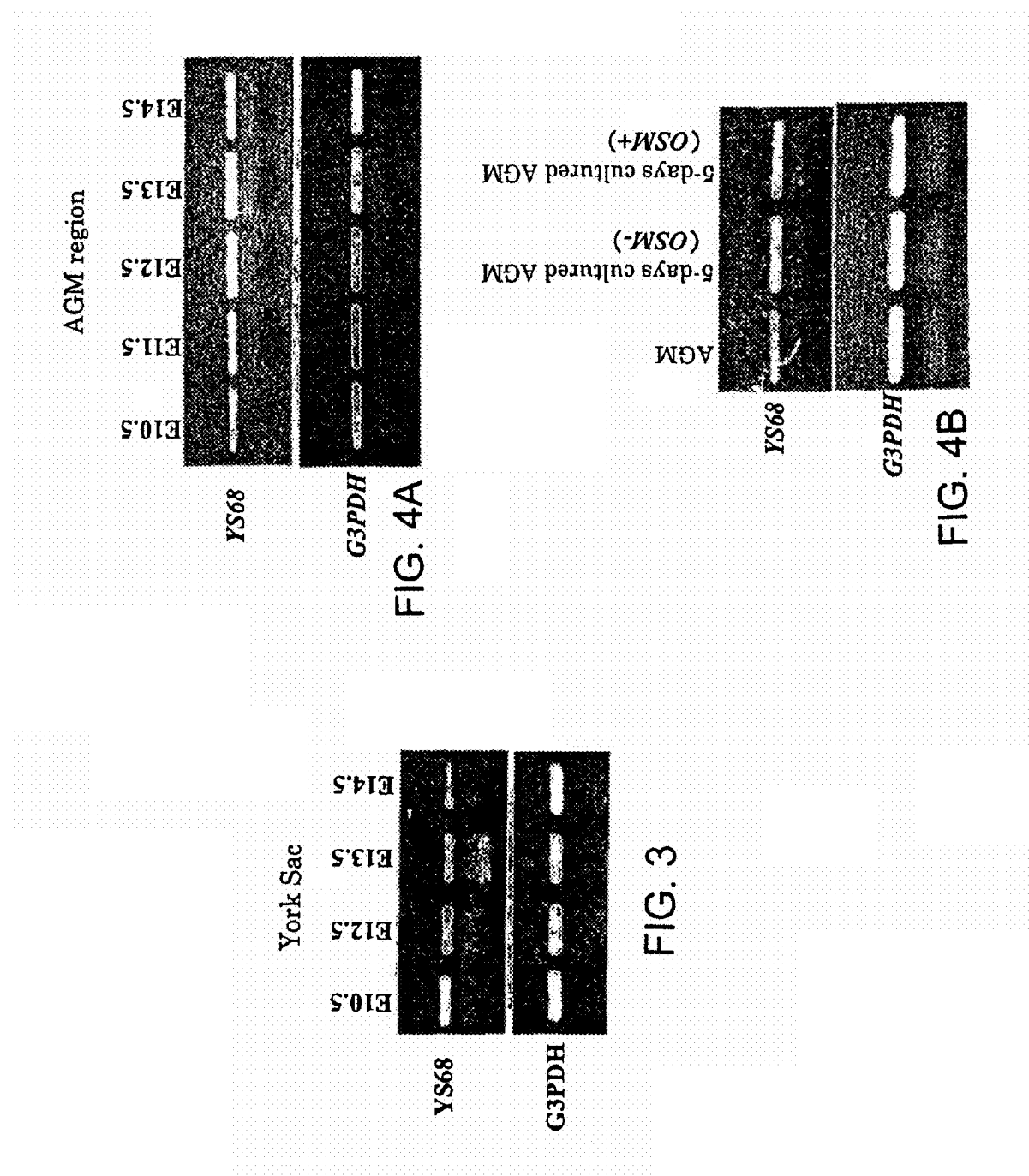

FIG. 8

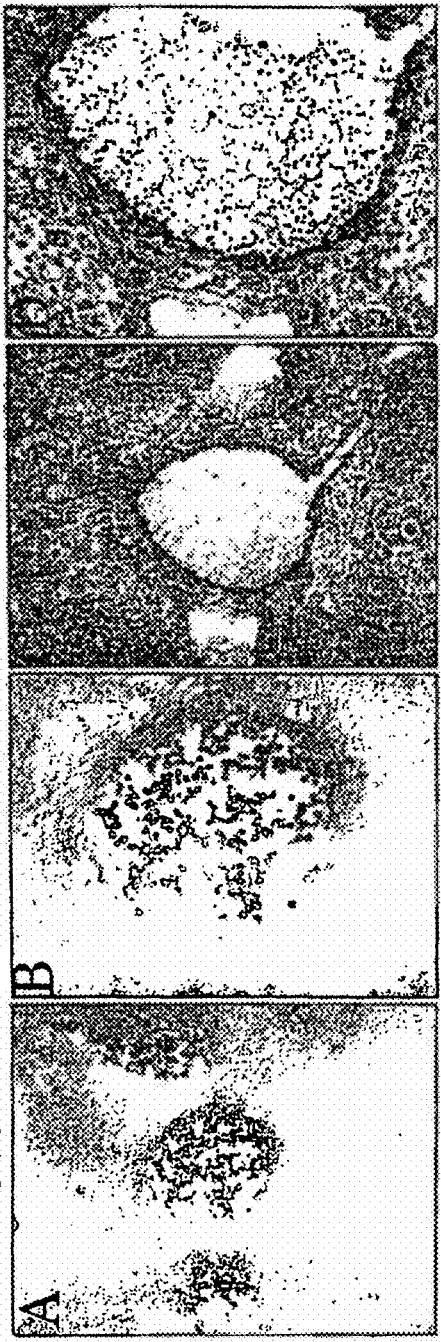

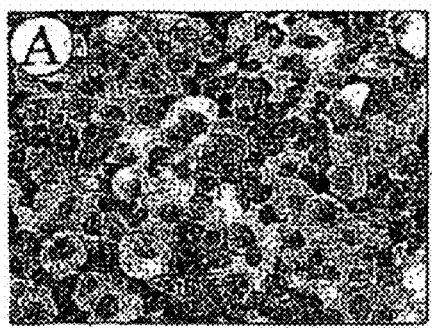
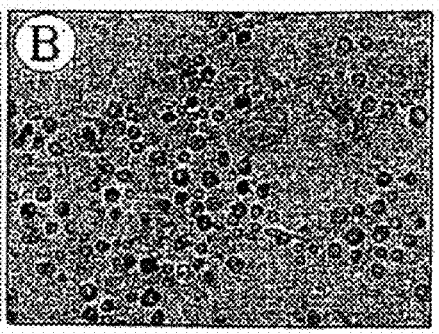
FIG. 13A　　　　　　　FIG. 13B
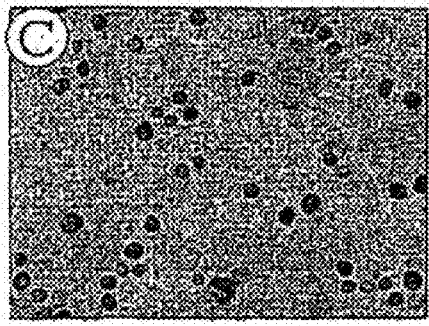
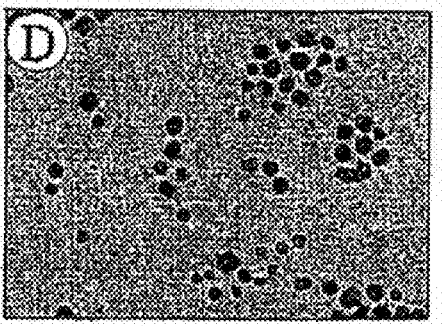
FIG. 13C　　　　　　　FIG. 13D
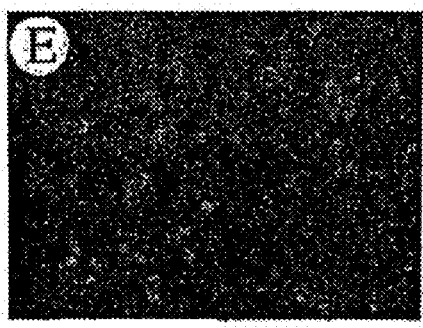
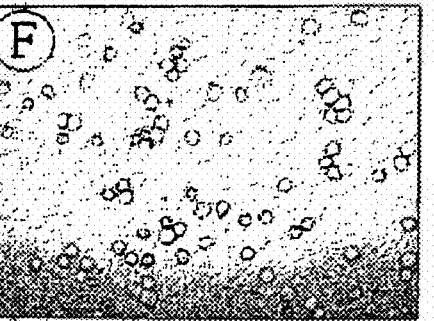
FIG. 13E　　　　　　　FIG. 13F
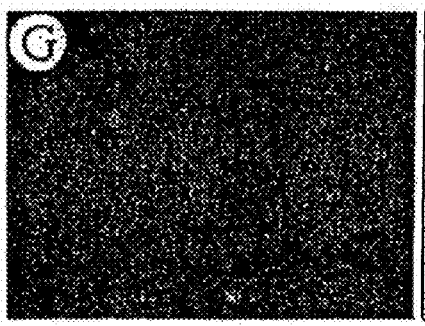
FIG. 13G　　　　　　　FIG. 13H

SEQUENCE LISTING

```
<160> NUMBER OF SEQ ID NOS: 16

<210> SEQ ID NO 1
<211> LENGTH: 4115
<212> TYPE: DNA
<213> ORGANISM: Mus musculus
<220> FEATURE:
<221> NAME/KEY: CDS
<222> LOCATION: (2)..(3817)
<220> FEATURE:
<221> NAME/KEY: misc_feature
<222> LOCATION: (3101)..(3101)
<223> OTHER INFORMATION: n is a, c, g, or t

<400> SEQUENCE: 1 t cag att ctg aag aat aat ctc atg agt gat cgt gac cct cga ttg cgg      49
  Gln Ile Leu Lys Asn Asn Leu Met Ser Asp Arg Asp Pro Arg Leu Arg
  1               5                   10                  15 gaa aga tcg gtg act cga aat tct ata tta gac cag tat ggg aaa atc       97
Glu Arg Ser Val Thr Arg Asn Ser Ile Leu Asp Gln Tyr Gly Lys Ile
            20                  25                  30 cta cct aga gtc cag aga aag tta gct gtt gag cga gct aag cct tac      145
Leu Pro Arg Val Gln Arg Lys Leu Ala Val Glu Arg Ala Lys Pro Tyr
        35                  40                  45 cac ctg tcg aca tcc tca gtt ttt cat gaa gtt tct aga ccc aaa ccg      193
His Leu Ser Thr Ser Ser Val Phe His Glu Val Ser Arg Pro Lys Pro
    50                  55                  60 tta tcg gca ttt cca aag aaa gct ata act gga aca gtg tta acc cga      241
Leu Ser Ala Phe Pro Lys Lys Ala Ile Thr Gly Thr Val Leu Thr Arg
65                  70                  75                  80 tct acg ttc atc agc aat gtt tta tct aaa att gga gag gtg tgg gca      289
Ser Thr Phe Ile Ser Asn Val Leu Ser Lys Ile Gly Glu Val Trp Ala
                85                  90                  95 agt cat gag cct aga aat ggc gtc tca ctt ttt aac agt cct aaa aca      337
Ser His Glu Pro Arg Asn Gly Val Ser Leu Phe Asn Ser Pro Lys Thr
            100                 105                 110 gaa cag cca tct cct gta gta cac tct ttc cca cac cca gag ctt cct      385
Glu Gln Pro Ser Pro Val Val His Ser Phe Pro His Pro Glu Leu Pro
        115                 120                 125 gag gcg ttt gtt gga act cca att tca aat aca tcc cag aga att tct      433
Glu Ala Phe Val Gly Thr Pro Ile Ser Asn Thr Ser Gln Arg Ile Ser
    130                 135                 140 aga tta ctg gat ttg gtt gtc cat cct gta ccc cag cct tct cag tgt      481
Arg Leu Leu Asp Leu Val Val His Pro Val Pro Gln Pro Ser Gln Cys
145                 150                 155                 160 ttg gag ttt att caa caa agt ccc aca aga tct cct ttg tgt ctg ctg      529
Leu Glu Phe Ile Gln Gln Ser Pro Thr Arg Ser Pro Leu Cys Leu Leu
                165                 170                 175 tcc agt tcg tta cca tta agt tca cag ttt aaa agg cca cat cag aat      577
```

```
                Ser Ser Ser Leu Pro Leu Ser Ser Gln Phe Lys Arg Pro His Gln Asn
                            180                 185                 190 acc tcc agg cct tca gag ttg ctt tta ctt gag act cct ctc ata gtt       625
Thr Ser Arg Pro Ser Glu Leu Leu Leu Leu Glu Thr Pro Leu Ile Val
            195                 200                 205 aag aaa gct aaa tct ttg gct ctg tca gcc acg tct tct gga ttt gcc       673
Lys Lys Ala Lys Ser Leu Ala Leu Ser Ala Thr Ser Ser Gly Phe Ala
            210                 215                 220 gag ttt act cct cca tcc atc ctt agg tct ggt ttt cga aca aca cct       721
Glu Phe Thr Pro Pro Ser Ile Leu Arg Ser Gly Phe Arg Thr Thr Pro
225                 230                 235                 240 tta gca tct ccc tct ttg tca cct gga aga tct ctc act ccg cct ttc       769
Leu Ala Ser Pro Ser Leu Ser Pro Gly Arg Ser Leu Thr Pro Pro Phe
                245                 250                 255 aga gtt aaa gaa aca agg att tca ttc atg gaa gaa ggc atg aat aca       817
Arg Val Lys Glu Thr Arg Ile Ser Phe Met Glu Glu Gly Met Asn Thr
                260                 265                 270 cac tgg act gat aga gct aca gat gac cga aat aca aaa gcg ttt gtt       865
His Trp Thr Asp Arg Ala Thr Asp Asp Arg Asn Thr Lys Ala Phe Val
            275                 280                 285 agc aca tct ttc cat aaa tgt gga ctt cca gca gaa act gag tgg atg       913
Ser Thr Ser Phe His Lys Cys Gly Leu Pro Ala Glu Thr Glu Trp Met
290                 295                 300 aag acc agt gat aag aat aca tat ttt cct ctg gat gtc cct gca aag       961
Lys Thr Ser Asp Lys Asn Thr Tyr Phe Pro Leu Asp Val Pro Ala Lys
305                 310                 315                 320 ggc cct cag aaa gtg gtg gca gag tca ctg gct acc cat tca gga agg      1009
Gly Pro Gln Lys Val Val Ala Glu Ser Leu Ala Thr His Ser Gly Arg
                325                 330                 335 ctg gag aaa ctg gat gtg agc aaa gaa gac agc aca gct tcc acc agg      1057
Leu Glu Lys Leu Asp Val Ser Lys Glu Asp Ser Thr Ala Ser Thr Arg
            340                 345                 350 tca gac cag acc tcc tta gag tat cat gac gca cca tca cca gaa gac      1105
Ser Asp Gln Thr Ser Leu Glu Tyr His Asp Ala Pro Ser Pro Glu Asp
            355                 360                 365 ttg gaa ggt gct gtt ttt gtg tct ccc aag cca gca tct tcc tcc act      1153
Leu Glu Gly Ala Val Phe Val Ser Pro Lys Pro Ala Ser Ser Ser Thr
            370                 375                 380 gaa cta act act aat tca act cta caa aca gag agg gat aat gat aaa      1201
Glu Leu Thr Thr Asn Ser Thr Leu Gln Thr Glu Arg Asp Asn Asp Lys
385                 390                 395                 400 gat gcg ttt aag tca gaa ggt act cct tca ccc gtg aag aaa caa ata      1249
Asp Ala Phe Lys Ser Glu Gly Thr Pro Ser Pro Val Lys Lys Gln Ile
                405                 410                 415 ggc acg gga gac gct gca gtg gaa gca ttt tca gaa ctg agt cgc tta      1297
Gly Thr Gly Asp Ala Ala Val Glu Ala Phe Ser Glu Leu Ser Arg Leu
            420                 425                 430 gac cct gtt gaa aga gct gaa gct tct ttt ggt gtg tcg tca gtc tgt      1345
Asp Pro Val Glu Arg Ala Glu Ala Ser Phe Gly Val Ser Ser Val Cys
            435                 440                 445 gaa ggg gaa acc tcc act tca aac tcc aag acg tca gtt ctg gat gga      1393
Glu Gly Glu Thr Ser Thr Ser Asn Ser Lys Thr Ser Val Leu Asp Gly
450                 455                 460 atc gtg cct att gag agc cga acc tcc ata ctt aca gca gac cac aaa      1441
Ile Val Pro Ile Glu Ser Arg Thr Ser Ile Leu Thr Ala Asp His Lys
465                 470                 475                 480 gag tct gtg gcc aac acg gtt gca gat gtt gaa agc tct ggg tcc acc      1489
Glu Ser Val Ala Asn Thr Val Ala Asp Val Glu Ser Ser Gly Ser Thr
            485                 490                 495 agc tcc aag tgc ccg gtt acc tct gaa cgc agc ctc ggc caa aaa cta      1537
```

```
        Ser Ser Lys Cys Pro Val Thr Ser Glu Arg Ser Leu Gly Gln Lys Leu
                    500                 505                 510 aca tta aac tta aaa gaa gat gaa ata gaa gct cat gta cca aag gag      1585
Thr Leu Asn Leu Lys Glu Asp Glu Ile Glu Ala His Val Pro Lys Glu
            515                 520                 525 aac gtt ggt tta cca gaa gaa agc cct cga att tct gct gct cct tct      1633
Asn Val Gly Leu Pro Glu Glu Ser Pro Arg Ile Ser Ala Ala Pro Ser
        530                 535                 540 gat act cac gag att cat cta att gga tgt gaa aat ctt gaa gtt caa      1681
Asp Thr His Glu Ile His Leu Ile Gly Cys Glu Asn Leu Glu Val Gln
545                 550                 555                 560 aat tca gaa gag gag gcc aag aat ctt tca ttt gat gag ttg tat ccc      1729
Asn Ser Glu Glu Glu Ala Lys Asn Leu Ser Phe Asp Glu Leu Tyr Pro
                565                 570                 575 tta ggg gca gag aaa ctt gag tat aat ctc agt act att gag cag cag      1777
Leu Gly Ala Glu Lys Leu Glu Tyr Asn Leu Ser Thr Ile Glu Gln Gln
            580                 585                 590 ttt tgt gac ttg cct gat gac aaa gac tct gct gaa tgt gat gct gct      1825
Phe Cys Asp Leu Pro Asp Asp Lys Asp Ser Ala Glu Cys Asp Ala Ala
        595                 600                 605 gaa gta gac ggg gaa ctt ttt gtg gcc cag agc aac ttt acc ctg att      1873
Glu Val Asp Gly Glu Leu Phe Val Ala Gln Ser Asn Phe Thr Leu Ile
610                 615                 620 tta gaa ggt gaa gaa gga gaa gct gag gca agc gac tct gca gca cct      1921
Leu Glu Gly Glu Glu Gly Glu Ala Glu Ala Ser Asp Ser Ala Ala Pro
625                 630                 635                 640 aat atg tta ccg aaa tcg acc aag gaa aaa cct gtg tgc tac agg gaa      1969
Asn Met Leu Pro Lys Ser Thr Lys Glu Lys Pro Val Cys Tyr Arg Glu
                645                 650                 655 ccc cat aat cag gag cgc gtt aca gat ttg cca tct gct gtg act gct      2017
Pro His Asn Gln Glu Arg Val Thr Asp Leu Pro Ser Ala Val Thr Ala
            660                 665                 670 gac caa gaa tcc cac aag gta gag act tta ccg tat gtg cct gaa ccg      2065
Asp Gln Glu Ser His Lys Val Glu Thr Leu Pro Tyr Val Pro Glu Pro
        675                 680                 685 gtt aaa gtg gca att gca gaa aat ctg ttg gat gta att aaa gac acc      2113
Val Lys Val Ala Ile Ala Glu Asn Leu Leu Asp Val Ile Lys Asp Thr
690                 695                 700 aga agt aag gaa gca act ccc gtg gca gca ggt gag gct ggt gat gag      2161
Arg Ser Lys Glu Ala Thr Pro Val Ala Ala Gly Glu Ala Gly Asp Glu
705                 710                 715                 720 gac gga gca gtg ata gtc tca aag gct gca cat tcg tcc agg ctg aca      2209
Asp Gly Ala Val Ile Val Ser Lys Ala Ala His Ser Ser Arg Leu Thr
                725                 730                 735 aac tct aca ccg aag act gtt aag gaa cca cgt gca gag act gta aat      2257
Asn Ser Thr Pro Lys Thr Val Lys Glu Pro Arg Ala Glu Thr Val Asn
            740                 745                 750 acc agc cag agt gat gac atg gtt tct tct aga act ctc aca aga agg      2305
Thr Ser Gln Ser Asp Asp Met Val Ser Ser Arg Thr Leu Thr Arg Arg
        755                 760                 765 cag cat gcc cta agc ctg aat gtc aca tca gaa caa gag cct tca gca      2353
Gln His Ala Leu Ser Leu Asn Val Thr Ser Glu Gln Glu Pro Ser Ala
770                 775                 780 gtt gcc act cct aag aag aga act aga aaa att aaa gaa act cct gag      2401
Val Ala Thr Pro Lys Lys Arg Thr Arg Lys Ile Lys Glu Thr Pro Glu
785                 790                 795                 800 tct tct gaa agg acc tgt tct gac cta aaa gta gca cct gag aac caa      2449
Ser Ser Glu Arg Thr Cys Ser Asp Leu Lys Val Ala Pro Glu Asn Gln
                805                 810                 815 ctg aca gct cag aat cct ccc gct cct agg aga aga aag aag aag gac      2497
```

```
        Leu Thr Ala Gln Asn Pro Pro Ala Pro Arg Arg Arg Lys Lys Lys Asp
                    820                 825                 830 gtt agc caa ggc aca ctg cca agt tct ggt gct gtg gag ccg gag ccg         2545
Val Ser Gln Gly Thr Leu Pro Ser Ser Gly Ala Val Glu Pro Glu Pro
            835                 840                 845 gaa cct cag ggt acg ccg gga aga ctg agg ctg aga acg cag cca ccc         2593
Glu Pro Gln Gly Thr Pro Gly Arg Leu Arg Leu Arg Thr Gln Pro Pro
    850                 855                 860 gag cca gca gct gaa gaa act cct tct aga aca aaa gtc agg ctt tca         2641
Glu Pro Ala Ala Glu Glu Thr Pro Ser Arg Thr Lys Val Arg Leu Ser
865                 870                 875                 880 tct gtt aga aag gga acc cct aga aga ctt aag aag tct gta gaa aat         2689
Ser Val Arg Lys Gly Thr Pro Arg Arg Leu Lys Lys Ser Val Glu Asn
                885                 890                 895 ggg caa agt ata gaa att cta gat gat ctc aaa ggg agt gag gca gca         2737
Gly Gln Ser Ile Glu Ile Leu Asp Asp Leu Lys Gly Ser Glu Ala Ala
            900                 905                 910 agt cat gac ggg act gtc aca gag ctg agg aat gcc aat tta gaa gat         2785
Ser His Asp Gly Thr Val Thr Glu Leu Arg Asn Ala Asn Leu Glu Asp
        915                 920                 925 act cag aat atg gag tat aaa caa gat gaa cac agt gac cag caa ccg         2833
Thr Gln Asn Met Glu Tyr Lys Gln Asp Glu His Ser Asp Gln Gln Pro
    930                 935                 940 cct cta aaa cga aag agg gtc aga gag aga gaa gtt agt gtg tca agt         2881
Pro Leu Lys Arg Lys Arg Val Arg Glu Arg Glu Val Ser Val Ser Ser
945                 950                 955                 960 gtg aca gaa gag cca aag ctt gac tca tcc cag ttg cct ctt cag aca         2929
Val Thr Glu Glu Pro Lys Leu Asp Ser Ser Gln Leu Pro Leu Gln Thr
                965                 970                 975 gga ctc gat gta cct gcc acc cct agg aaa cgt ggt aga ccc agg aag         2977
Gly Leu Asp Val Pro Ala Thr Pro Arg Lys Arg Gly Arg Pro Arg Lys
            980                 985                 990 gta gtt ccc tta gaa gct gac ggt  ggc aca act ggt aag  gaa cag aca       3025
Val Val Pro Leu Glu Ala Asp Gly  Gly Thr Thr Gly Lys  Glu Gln Thr
        995                 1000                1005 agt cct cag aag aaa gat gtt  ccg gtt gtc cgg aga  tct aca cgg           3070
Ser Pro Gln Lys Lys Asp Val  Pro Val Val Arg Arg  Ser Thr Arg
    1010                1015                1020 aac acc cca gct aga aat gtg  agt act tta naa aaa  tca gtt tta           3115
Asn Thr Pro Ala Arg Asn Val  Ser Thr Leu Xaa Lys  Ser Val Leu
1025                1030                1035 gtg cca aat aag gaa gct gct  cta gtg gtg aca tct  aag agg aga           3160
Val Pro Asn Lys Glu Ala Ala  Leu Val Val Thr Ser  Lys Arg Arg
    1040                1045                1050 cct aca aag aag tct gca gag  gaa agc tca aaa gat  cca tca gcg           3205
Pro Thr Lys Lys Ser Ala Glu  Glu Ser Ser Lys Asp  Pro Ser Ala
    1055                1060                1065 gca gtc tca gac tgg gcg ggt  gga gca gcc cac aca  gag tcc gct           3250
Ala Val Ser Asp Trp Ala Gly  Gly Ala Ala His Thr  Glu Ser Ala
    1070                1075                1080 gac cga agg gac gga ctg ctt  gcc gcc gct gct ctc  acg cca tct           3295
Asp Arg Arg Asp Gly Leu Leu  Ala Ala Ala Ala Leu  Thr Pro Ser
    1085                1090                1095 gcc cag ggc aca agg act agg  tct aga agg acc atg  ttg ttg acg           3340
Ala Gln Gly Thr Arg Thr Arg  Ser Arg Arg Thr Met  Leu Leu Thr
    1100                1105                1110 gac att tct gaa ccc aaa act  gag cct tta ttt cct  cct cct tca           3385
Asp Ile Ser Glu Pro Lys Thr  Glu Pro Leu Phe Pro  Pro Pro Ser
    1115                1120                1125 gtg aag gtt cca aag aaa aaa  tca aaa gct gag aac  atg gag gcc           3430
```

-continued

| | | | | | | | | | | | | | | |
|---|---|---|---|---|---|---|---|---|---|---|---|---|---|---|
| Val | Lys | Val | Pro | Lys | Lys | Ser | Lys | Ala | Glu | Asn | Met | Glu | Ala | |
| | 1130 | | | | 1135 | | | | 1140 | | | | | |

```
gca gcc cag ctg aaa gaa ttg gtg tca gat tta tct tct cag ttt    3475
Ala Ala Gln Leu Lys Glu Leu Val Ser Asp Leu Ser Ser Gln Phe
    1145            1150                1155 gtt gtt tcc cct cct gcc ttg aga acc agg cag aaa agt ata tcc    3520
Val Val Ser Pro Pro Ala Leu Arg Thr Arg Gln Lys Ser Ile Ser
    1160            1165                1170 aat act tcc aag ctt cta ggt gaa ctg gag agt gac cct aaa cca    3565
Asn Thr Ser Lys Leu Leu Gly Glu Leu Glu Ser Asp Pro Lys Pro
1175            1180                1185 tta gag atc ata gaa caa aaa cca aaa aga agc agg act gtg aag    3610
Leu Glu Ile Ile Glu Gln Lys Pro Lys Arg Ser Arg Thr Val Lys
    1190            1195                1200 aca aga gca agc aga aac aca gga aaa gga agt tct tgg tca cct    3655
Thr Arg Ala Ser Arg Asn Thr Gly Lys Gly Ser Ser Trp Ser Pro
    1205            1210                1215 cct cct gta gaa att aag ctg gtt tct ccc ttg gcg agt cca gtg    3700
Pro Pro Val Glu Ile Lys Leu Val Ser Pro Leu Ala Ser Pro Val
    1220            1225                1230 gat gaa ata aag acc ggc aag cca aga aaa act gca gaa ata gca    3745
Asp Glu Ile Lys Thr Gly Lys Pro Arg Lys Thr Ala Glu Ile Ala
1235            1240                1245 gga aaa act ctt gga agg ggc aga aag aag cca tct tct ttt cca    3790
Gly Lys Thr Leu Gly Arg Gly Arg Lys Lys Pro Ser Ser Phe Pro
    1250            1255                1260 aag caa att tta cgc agg aaa atg ctg taattttag cccaagattt       3837
Lys Gln Ile Leu Arg Arg Lys Met Leu
    1265            1270 taacacgcac ctgtttgtaa aagtcaacag tatttgtgtg gattattaaa gtcaccaatt   3897
tggatgaaaa tactttatat aaattgtaca attttgtaag cagtaaatga gtaactccac   3957
atggagtgca gttcttgtag tgcaggcgtt ttatacgact tgatgcgttt atatcaatgt   4017
aaatatgact tatcattggg aggttaaata aactactgta aagtaaaaaa aaaaaaaaaa   4077
aaaaaaaaaa aaaaaaaaaa aaaaaaaaaa aaaaaaaa                            4115

<210> SEQ ID NO 2
<211> LENGTH: 1272
<212> TYPE: PRT
<213> ORGANISM: Mus musculus
<220> FEATURE:
<221> NAME/KEY: misc_feature
<222> LOCATION: (1034)..(1034)
<223> OTHER INFORMATION: The 'Xaa' at location 1034 stands for Lys, Glu,
      or Gln.

<400> SEQUENCE: 2

Gln Ile Leu Lys Asn Asn Leu Met Ser Asp Arg Asp Pro Arg Leu Arg
1               5                   10                  15

Glu Arg Ser Val Thr Arg Asn Ser Ile Leu Asp Gln Tyr Gly Lys Ile
                20                  25                  30

Leu Pro Arg Val Gln Arg Lys Leu Ala Val Glu Arg Ala Lys Pro Tyr
            35                  40                  45

His Leu Ser Thr Ser Ser Val Phe His Glu Val Ser Arg Pro Lys Pro
        50                  55                  60

Leu Ser Ala Phe Pro Lys Lys Ala Ile Thr Gly Thr Val Leu Thr Arg
65                  70                  75                  80

Ser Thr Phe Ile Ser Asn Val Leu Ser Lys Ile Gly Glu Val Trp Ala
                85                  90                  95
```

-continued

```
Ser His Glu Pro Arg Asn Gly Val Ser Leu Phe Asn Ser Pro Lys Thr
            100                 105                 110

Glu Gln Pro Ser Pro Val Val His Ser Phe Pro His Pro Glu Leu Pro
        115                 120                 125

Glu Ala Phe Val Gly Thr Pro Ile Ser Asn Thr Ser Gln Arg Ile Ser
130                 135                 140

Arg Leu Leu Asp Leu Val Val His Pro Val Pro Gln Pro Ser Gln Cys
145                 150                 155                 160

Leu Glu Phe Ile Gln Gln Ser Pro Thr Arg Ser Pro Leu Cys Leu Leu
                165                 170                 175

Ser Ser Ser Leu Pro Leu Ser Ser Gln Phe Lys Arg Pro His Gln Asn
            180                 185                 190

Thr Ser Arg Pro Ser Glu Leu Leu Leu Glu Thr Pro Leu Ile Val
        195                 200                 205

Lys Lys Ala Lys Ser Leu Ala Leu Ser Ala Thr Ser Ser Gly Phe Ala
        210                 215                 220

Glu Phe Thr Pro Pro Ser Ile Leu Arg Ser Gly Phe Arg Thr Thr Pro
225                 230                 235                 240

Leu Ala Ser Pro Ser Leu Ser Pro Gly Arg Ser Leu Thr Pro Pro Phe
                245                 250                 255

Arg Val Lys Glu Thr Arg Ile Ser Phe Met Glu Glu Gly Met Asn Thr
            260                 265                 270

His Trp Thr Asp Arg Ala Thr Asp Asp Arg Asn Thr Lys Ala Phe Val
        275                 280                 285

Ser Thr Ser Phe His Lys Cys Gly Leu Pro Ala Glu Thr Glu Trp Met
        290                 295                 300

Lys Thr Ser Asp Lys Asn Thr Tyr Phe Pro Leu Asp Val Pro Ala Lys
305                 310                 315                 320

Gly Pro Gln Lys Val Val Ala Glu Ser Leu Ala Thr His Ser Gly Arg
                325                 330                 335

Leu Glu Lys Leu Asp Val Ser Lys Glu Asp Ser Thr Ala Ser Thr Arg
            340                 345                 350

Ser Asp Gln Thr Ser Leu Glu Tyr His Asp Ala Pro Ser Pro Glu Asp
        355                 360                 365

Leu Glu Gly Ala Val Phe Val Ser Pro Lys Pro Ala Ser Ser Ser Thr
370                 375                 380

Glu Leu Thr Thr Asn Ser Thr Leu Gln Thr Glu Arg Asp Asn Asp Lys
385                 390                 395                 400

Asp Ala Phe Lys Ser Glu Gly Thr Pro Ser Pro Val Lys Lys Gln Ile
                405                 410                 415

Gly Thr Gly Asp Ala Ala Val Glu Ala Phe Ser Glu Leu Ser Arg Leu
            420                 425                 430

Asp Pro Val Glu Arg Ala Glu Ala Ser Phe Gly Val Ser Ser Val Cys
        435                 440                 445

Glu Gly Glu Thr Ser Thr Ser Asn Ser Lys Thr Ser Val Leu Asp Gly
        450                 455                 460

Ile Val Pro Ile Glu Ser Arg Thr Ser Ile Leu Thr Ala Asp His Lys
465                 470                 475                 480

Glu Ser Val Ala Asn Thr Val Ala Asp Val Glu Ser Ser Gly Ser Thr
                485                 490                 495

Ser Ser Lys Cys Pro Val Thr Ser Glu Arg Ser Leu Gly Gln Lys Leu
            500                 505                 510

Thr Leu Asn Leu Lys Glu Asp Glu Ile Glu Ala His Val Pro Lys Glu
        515                 520                 525
```

-continued

Asn Val Gly Leu Pro Glu Glu Ser Pro Arg Ile Ser Ala Ala Pro Ser
530                 535                 540

Asp Thr His Glu Ile His Leu Ile Gly Cys Glu Asn Leu Glu Val Gln
545                 550                 555                 560

Asn Ser Glu Glu Glu Ala Lys Asn Leu Ser Phe Asp Glu Leu Tyr Pro
                565                 570                 575

Leu Gly Ala Glu Lys Leu Glu Tyr Asn Leu Ser Thr Ile Glu Gln Gln
            580                 585                 590

Phe Cys Asp Leu Pro Asp Lys Asp Ser Ala Glu Cys Asp Ala Ala
        595                 600                 605

Glu Val Asp Gly Glu Leu Phe Val Ala Gln Ser Asn Phe Thr Leu Ile
610                 615                 620

Leu Glu Gly Glu Glu Gly Glu Ala Glu Ala Ser Asp Ser Ala Ala Pro
625                 630                 635                 640

Asn Met Leu Pro Lys Ser Thr Lys Glu Lys Pro Val Cys Tyr Arg Glu
                645                 650                 655

Pro His Asn Gln Glu Arg Val Thr Asp Leu Pro Ser Ala Val Thr Ala
                660                 665                 670

Asp Gln Glu Ser His Lys Val Glu Thr Leu Pro Tyr Val Pro Glu Pro
        675                 680                 685

Val Lys Val Ala Ile Ala Glu Asn Leu Leu Asp Val Ile Lys Asp Thr
690                 695                 700

Arg Ser Lys Glu Ala Thr Pro Val Ala Ala Gly Glu Ala Gly Asp Glu
705                 710                 715                 720

Asp Gly Ala Val Ile Val Ser Lys Ala His Ser Ser Arg Leu Thr
                725                 730                 735

Asn Ser Thr Pro Lys Thr Val Lys Glu Pro Arg Ala Glu Thr Val Asn
            740                 745                 750

Thr Ser Gln Ser Asp Asp Met Val Ser Ser Arg Thr Leu Thr Arg Arg
        755                 760                 765

Gln His Ala Leu Ser Leu Asn Val Thr Ser Glu Gln Glu Pro Ser Ala
770                 775                 780

Val Ala Thr Pro Lys Lys Arg Thr Arg Lys Ile Lys Glu Thr Pro Glu
785                 790                 795                 800

Ser Ser Glu Arg Thr Cys Ser Asp Leu Lys Val Ala Pro Glu Asn Gln
                805                 810                 815

Leu Thr Ala Gln Asn Pro Pro Ala Pro Arg Arg Arg Lys Lys Lys Asp
            820                 825                 830

Val Ser Gln Gly Thr Leu Pro Ser Gly Ala Val Glu Pro Glu Pro
835                 840                 845

Glu Pro Gln Gly Thr Pro Gly Arg Leu Arg Leu Arg Thr Gln Pro Pro
850                 855                 860

Glu Pro Ala Ala Glu Glu Thr Pro Ser Arg Thr Lys Val Arg Leu Ser
865                 870                 875                 880

Ser Val Arg Lys Gly Thr Pro Arg Arg Leu Lys Lys Ser Val Glu Asn
                885                 890                 895

Gly Gln Ser Ile Glu Ile Leu Asp Asp Leu Lys Gly Ser Glu Ala Ala
                900                 905                 910

Ser His Asp Gly Thr Val Thr Glu Leu Arg Asn Ala Asn Leu Glu Asp
        915                 920                 925

Thr Gln Asn Met Glu Tyr Lys Gln Asp Glu His Ser Asp Gln Gln Pro
930                 935                 940

Pro Leu Lys Arg Lys Arg Val Arg Glu Arg Glu Val Ser Val Ser Ser

```
                    945                 950                 955                 960
Val Thr Glu Glu Pro Lys Leu Asp Ser Ser Gln Leu Pro Leu Gln Thr
                    965                 970                 975
Gly Leu Asp Val Pro Ala Thr Pro Arg Lys Arg Gly Arg Pro Arg Lys
                    980                 985                 990
Val Val Pro Leu Glu Ala Asp Gly  Gly Thr Thr Gly Lys  Glu Gln Thr
        995                 1000                1005
Ser Pro  Gln Lys Lys Asp Val  Pro Val Val Arg  Ser Thr Arg
    1010                1015                1020
Asn Thr  Pro Ala Arg Asn Val  Ser Thr Leu Xaa  Lys Ser Val Leu
    1025                1030                1035
Val Pro  Asn Lys Glu Ala Ala  Leu Val Val Thr  Ser Lys Arg Arg
    1040                1045                1050
Pro Thr  Lys Lys Ser Ala Glu  Glu Ser Ser Lys  Asp Pro Ser Ala
    1055                1060                1065
Ala Val  Ser Asp Trp Ala Gly  Gly Ala Ala His  Thr Glu Ser Ala
    1070                1075                1080
Asp Arg  Arg Asp Gly Leu Leu  Ala Ala Ala Leu  Thr Pro Ser
    1085                1090                1095
Ala Gln  Gly Thr Arg Thr Arg  Ser Arg Arg Thr  Met Leu Leu Thr
    1100                1105                1110
Asp Ile  Ser Glu Pro Lys Thr  Glu Pro Leu Phe  Pro Pro Pro Ser
    1115                1120                1125
Val Lys  Val Pro Lys Lys Lys  Ser Lys Ala Glu  Asn Met Glu Ala
    1130                1135                1140
Ala Ala  Gln Leu Lys Glu Leu  Val Ser Asp Leu  Ser Ser Gln Phe
    1145                1150                1155
Val Val  Ser Pro Pro Ala Leu  Arg Thr Arg Gln  Lys Ser Ile Ser
    1160                1165                1170
Asn Thr  Ser Lys Leu Leu Gly  Glu Leu Glu Ser  Asp Pro Lys Pro
    1175                1180                1185
Leu Glu  Ile Ile Glu Gln Lys  Pro Lys Arg Ser  Arg Thr Val Lys
    1190                1195                1200
Thr Arg  Ala Ser Arg Asn Thr  Gly Lys Gly Ser  Ser Trp Ser Pro
    1205                1210                1215
Pro Pro  Val Glu Ile Lys Leu  Val Ser Pro Leu  Ala Ser Pro Val
    1220                1225                1230
Asp Glu  Ile Lys Thr Gly Lys  Pro Arg Lys Thr  Ala Glu Ile Ala
    1235                1240                1245
Gly Lys  Thr Leu Gly Arg Gly  Arg Lys Lys Pro  Ser Ser Phe Pro
    1250                1255                1260
Lys Gln  Ile Leu Arg Arg Lys  Met Leu
    1265                1270

<210> SEQ ID NO 3
<211> LENGTH: 24
<212> TYPE: DNA
<213> ORGANISM: Artificial
<220> FEATURE:
<223> OTHER INFORMATION: Description of Artificial Sequence:Artificially
      Synthesized Primer Sequence

<400> SEQUENCE: 3
cacccgtgaa gaaacaaata ggca                                              24

<210> SEQ ID NO 4
```

```
<211> LENGTH: 24
<212> TYPE: DNA
<213> ORGANISM: Artificial
<220> FEATURE:
<223> OTHER INFORMATION: Description of Artificial Sequence:Artificially
      Synthesized Primer Sequence

<400> SEQUENCE: 4
cctttggtac atgagcttct attt                                              24

<210> SEQ ID NO 5
<211> LENGTH: 4883
<212> TYPE: DNA
<213> ORGANISM: Homo sapiens
<220> FEATURE:
<221> NAME/KEY: CDS
<222> LOCATION: (1)..(4590)

<400> SEQUENCE: 5
```

| | | | | | | | | | | | | | | | | |
|---|---|---|---|---|---|---|---|---|---|---|---|---|---|---|---|---|
| gag | aag | ttg | tgg | aaa | cga | gat | gaa | gga | ggc | aca | gga | aaa | tat | cct | cct | 48 |
| Glu | Lys | Leu | Trp | Lys | Arg | Asp | Glu | Gly | Gly | Thr | Gly | Lys | Tyr | Pro | Pro | |
| 1 | | | | 5 | | | | | 10 | | | | | 15 | | |
| gct | agt | ctg | cat | gca | gta | ctt | gat | atg | tac | cta | tta | gac | ggc | gtt | act | 96 |
| Ala | Ser | Leu | His | Ala | Val | Leu | Asp | Met | Tyr | Leu | Leu | Asp | Gly | Val | Thr | |
| | | | 20 | | | | | 25 | | | | | 30 | | | |
| gaa | gca | gcc | aaa | cac | tct | att | acc | att | tat | ttg | cta | ctt | gat | att | atg | 144 |
| Glu | Ala | Ala | Lys | His | Ser | Ile | Thr | Ile | Tyr | Leu | Leu | Leu | Asp | Ile | Met | |
| | | 35 | | | | | 40 | | | | | 45 | | | | |
| tat | tcc | ttt | ccc | aac | aaa | aca | gac | act | ccc | att | gaa | tct | ttc | cca | act | 192 |
| Tyr | Ser | Phe | Pro | Asn | Lys | Thr | Asp | Thr | Pro | Ile | Glu | Ser | Phe | Pro | Thr | |
| | 50 | | | | | 55 | | | | | 60 | | | | | |
| gta | ttt | gcc | att | tct | tgg | ggc | caa | gtt | aaa | ctt | att | cag | ggg | ttt | tgg | 240 |
| Val | Phe | Ala | Ile | Ser | Trp | Gly | Gln | Val | Lys | Leu | Ile | Gln | Gly | Phe | Trp | |
| 65 | | | | | 70 | | | | | 75 | | | | | 80 | |
| ttg | ata | gat | cat | aat | gac | tat | gag | agt | ggt | ttg | gat | ctt | ttg | ttt | cat | 288 |
| Leu | Ile | Asp | His | Asn | Asp | Tyr | Glu | Ser | Gly | Leu | Asp | Leu | Leu | Phe | His | |
| | | | | 85 | | | | | 90 | | | | | 95 | | |
| cca | gct | act | gca | aaa | cct | ttg | tca | tgg | caa | cat | tca | aag | att | att | cag | 336 |
| Pro | Ala | Thr | Ala | Lys | Pro | Leu | Ser | Trp | Gln | His | Ser | Lys | Ile | Ile | Gln | |
| | | | 100 | | | | | 105 | | | | | 110 | | | |
| gca | ttc | atg | agt | cag | ggc | gag | cac | aga | caa | gcc | ctc | aga | tat | att | cag | 384 |
| Ala | Phe | Met | Ser | Gln | Gly | Glu | His | Arg | Gln | Ala | Leu | Arg | Tyr | Ile | Gln | |
| | | 115 | | | | | 120 | | | | | 125 | | | | |
| aca | atg | aag | cca | aca | gtg | tcc | agt | ggt | aac | gat | gtt | atc | ctt | cac | ctc | 432 |
| Thr | Met | Lys | Pro | Thr | Val | Ser | Ser | Gly | Asn | Asp | Val | Ile | Leu | His | Leu | |
| | 130 | | | | | 135 | | | | | 140 | | | | | |
| act | gtt | ttg | ctt | ttt | aat | agg | tgt | atg | gtt | gaa | gcc | tgg | aat | ttt | ttg | 480 |
| Thr | Val | Leu | Leu | Phe | Asn | Arg | Cys | Met | Val | Glu | Ala | Trp | Asn | Phe | Leu | |
| 145 | | | | | 150 | | | | | 155 | | | | | 160 | |
| cgg | caa | cat | tgc | aat | agg | ttg | aat | ata | gag | gag | tta | ctg | aag | cac | atg | 528 |
| Arg | Gln | His | Cys | Asn | Arg | Leu | Asn | Ile | Glu | Glu | Leu | Leu | Lys | His | Met | |
| | | | | 165 | | | | | 170 | | | | | 175 | | |
| tat | gaa | gtc | tgt | cag | gaa | atg | ggc | ttg | atg | gaa | gat | tta | ctg | aag | tta | 576 |
| Tyr | Glu | Val | Cys | Gln | Glu | Met | Gly | Leu | Met | Glu | Asp | Leu | Leu | Lys | Leu | |
| | | | 180 | | | | | 185 | | | | | 190 | | | |
| cca | ttt | aca | gac | act | gag | cag | gaa | tgt | tta | gtg | aaa | ttt | ttg | cag | tcc | 624 |
| Pro | Phe | Thr | Asp | Thr | Glu | Gln | Glu | Cys | Leu | Val | Lys | Phe | Leu | Gln | Ser | |
| | | 195 | | | | | 200 | | | | | 205 | | | | |
| agt | gcc | agc | gtt | cag | aat | cat | gaa | ttc | ctt | tta | gtg | cac | cat | ttg | cag | 672 |
| Ser | Ala | Ser | Val | Gln | Asn | His | Glu | Phe | Leu | Leu | Val | His | His | Leu | Gln | |
| | 210 | | | | | 215 | | | | | 220 | | | | | |
| cgt | gcc | aat | tat | gtg | cct | gcc | ttg | aag | ctg | aac | caa | act | ctg | aag | att | 720 |
| Arg | Ala | Asn | Tyr | Val | Pro | Ala | Leu | Lys | Leu | Asn | Gln | Thr | Leu | Lys | Ile | |

-continued

```
                225                 230                 235                 240
aat gtt atg aat gat cgt gat cct cgt ttg cgg gag aga tca ctg gct        768
Asn Val Met Asn Asp Arg Asp Pro Arg Leu Arg Glu Arg Ser Leu Ala
                    245                 250                 255 cga aat tct ata tta gac cag tat gga aaa atc ctt cct aga gtc cat        816
Arg Asn Ser Ile Leu Asp Gln Tyr Gly Lys Ile Leu Pro Arg Val His
                260                 265                 270 cga aaa tta gcc att gaa cga gct aag cct tat cat ctg tca aca tca        864
Arg Lys Leu Ala Ile Glu Arg Ala Lys Pro Tyr His Leu Ser Thr Ser
            275                 280                 285 tca gtt ttt cga tta gtt tct aga ccc aaa cca tta tca gca gtt cca        912
Ser Val Phe Arg Leu Val Ser Arg Pro Lys Pro Leu Ser Ala Val Pro
        290                 295                 300 aag caa gtt gta aca gga act gtg ttg aca aga tct gtt ttc atc aac        960
Lys Gln Val Val Thr Gly Thr Val Leu Thr Arg Ser Val Phe Ile Asn
305                 310                 315                 320 aat gtg tta tct aaa att gga gaa gtt tgg gca agc aaa gaa cct ata       1008
Asn Val Leu Ser Lys Ile Gly Glu Val Trp Ala Ser Lys Glu Pro Ile
                    325                 330                 335 aat agc acc aca cct ttc aat agt tct aaa ata gaa gaa cca tct cct       1056
Asn Ser Thr Thr Pro Phe Asn Ser Ser Lys Ile Glu Glu Pro Ser Pro
                340                 345                 350 ata gtg tat tcg ctc cca gct cca gag ctg cct gag gca ttt ttt gga       1104
Ile Val Tyr Ser Leu Pro Ala Pro Glu Leu Pro Glu Ala Phe Phe Gly
            355                 360                 365 aca cca att tca aaa gca tca caa aaa att tct aga ctg cta gat ttg       1152
Thr Pro Ile Ser Lys Ala Ser Gln Lys Ile Ser Arg Leu Leu Asp Leu
        370                 375                 380 gtt gtt cag cct gtc ccc cgg cct tct cag tgt tcg gag ttt att cag       1200
Val Val Gln Pro Val Pro Arg Pro Ser Gln Cys Ser Glu Phe Ile Gln
385                 390                 395                 400 caa agc tcc atg aaa tct cct ttg tac cta gta tcc cgt tca ctg ccc       1248
Gln Ser Ser Met Lys Ser Pro Leu Tyr Leu Val Ser Arg Ser Leu Pro
                    405                 410                 415 tca agt tcg caa tta aaa gga tcg cct cag gcc atc tcc agg gct tca       1296
Ser Ser Ser Gln Leu Lys Gly Ser Pro Gln Ala Ile Ser Arg Ala Ser
                420                 425                 430 gaa tta cat ttg ctt gaa act cct ctt gta gtt aag aaa gct aaa agt       1344
Glu Leu His Leu Leu Glu Thr Pro Leu Val Val Lys Lys Ala Lys Ser
            435                 440                 445 ttg gcc atg tca gtt act act tct gga ttt tct gag ttc act cct cag       1392
Leu Ala Met Ser Val Thr Thr Ser Gly Phe Ser Glu Phe Thr Pro Gln
        450                 455                 460 tcc atc ctg agg tct act cct cga tca aca cct tta gca tct ccc tct       1440
Ser Ile Leu Arg Ser Thr Pro Arg Ser Thr Pro Leu Ala Ser Pro Ser
465                 470                 475                 480 cca tca cct gga agg tct cct caa cga ctt aaa gaa act aga att tca       1488
Pro Ser Pro Gly Arg Ser Pro Gln Arg Leu Lys Glu Thr Arg Ile Ser
                    485                 490                 495 ttt gtg gaa gaa gat gtc cac cca aaa tgg att cct ggg gct gca gat       1536
Phe Val Glu Glu Asp Val His Pro Lys Trp Ile Pro Gly Ala Ala Asp
                500                 505                 510 gat agc aaa tta gaa gta ttt act aca cct aaa aaa tgt gca gtt cca       1584
Asp Ser Lys Leu Glu Val Phe Thr Thr Pro Lys Lys Cys Ala Val Pro
            515                 520                 525 gtg gaa act gaa tgg ccg aag agc aaa gat agg acc aca tct ttt ttc       1632
Val Glu Thr Glu Trp Pro Lys Ser Lys Asp Arg Thr Thr Ser Phe Phe
        530                 535                 540 ctg aac agc cct gaa aag gag cat caa gaa atg gat gag ggg tca caa       1680
Leu Asn Ser Pro Glu Lys Glu His Gln Glu Met Asp Glu Gly Ser Gln
```

-continued

```
        545                 550                 555                 560 agt tta gag aaa ctg gat gtg agc aaa gga aac agc agt gtt tca atc     1728
Ser Leu Glu Lys Leu Asp Val Ser Lys Gly Asn Ser Ser Val Ser Ile
                565                 570                 575 aca tcc gat gag act acc tta gag tat cag gat gca ccg tca ccg gaa     1776
Thr Ser Asp Glu Thr Thr Leu Glu Tyr Gln Asp Ala Pro Ser Pro Glu
                580                 585                 590 gac ctt gaa gag act gtt ttc acg gcc tct aag ccc aaa agc tct tcc     1824
Asp Leu Glu Glu Thr Val Phe Thr Ala Ser Lys Pro Lys Ser Ser Ser
                595                 600                 605 act gca cta act act aat gta act gaa caa act gaa aag gat gga gat     1872
Thr Ala Leu Thr Thr Asn Val Thr Glu Gln Thr Glu Lys Asp Gly Asp
                610                 615                 620 aaa gat gta ttt gca tca gaa gta act cct tca gac cta cag aaa caa     1920
Lys Asp Val Phe Ala Ser Glu Val Thr Pro Ser Asp Leu Gln Lys Gln
625                 630                 635                 640 atg ggc aat tta gaa gat gca gaa aca aag gat ctc tta gtt gca gca     1968
Met Gly Asn Leu Glu Asp Ala Glu Thr Lys Asp Leu Leu Val Ala Ala
                645                 650                 655 gag gca ttt tca gaa ttg aat cac tta agc ccg gtt caa gga act gaa     2016
Glu Ala Phe Ser Glu Leu Asn His Leu Ser Pro Val Gln Gly Thr Glu
                660                 665                 670 gct tct ctt tgt gca cca tca gtc tat gaa ggg aaa atc ttc acc cag     2064
Ala Ser Leu Cys Ala Pro Ser Val Tyr Glu Gly Lys Ile Phe Thr Gln
                675                 680                 685 aag tcc aag gta cca gtg ttg gac gaa gga tta aca tct gtt gaa acc     2112
Lys Ser Lys Val Pro Val Leu Asp Glu Gly Leu Thr Ser Val Glu Thr
                690                 695                 700 tac acc cct gca att aga gca aat gac aat aaa tct atg gct gat gtc     2160
Tyr Thr Pro Ala Ile Arg Ala Asn Asp Asn Lys Ser Met Ala Asp Val
705                 710                 715                 720 ctt ggt gat ggt gga aac tcc tcg ctc act atc tct gaa ggt cct att     2208
Leu Gly Asp Gly Gly Asn Ser Ser Leu Thr Ile Ser Glu Gly Pro Ile
                725                 730                 735 gtc tct gag cgc agg ctt aac cag gaa gta gcg ctg aac tta aaa gaa     2256
Val Ser Glu Arg Arg Leu Asn Gln Glu Val Ala Leu Asn Leu Lys Glu
                740                 745                 750 gat cat gaa gta gaa gtt ggt gta cta aaa gaa agt gtt gac tta cca     2304
Asp His Glu Val Glu Val Gly Val Leu Lys Glu Ser Val Asp Leu Pro
                755                 760                 765 gaa gaa aag ctt cca att tct gac agc cct cct gat act caa gaa att     2352
Glu Glu Lys Leu Pro Ile Ser Asp Ser Pro Pro Asp Thr Gln Glu Ile
                770                 775                 780 cat gtg att gaa caa gaa aag ctt gaa gct caa gat tca gga gaa gag     2400
His Val Ile Glu Gln Glu Lys Leu Glu Ala Gln Asp Ser Gly Glu Glu
785                 790                 795                 800 gct agg aat ctt tca ttt aat gag tta tat ccc tct gga aca ctt aag     2448
Ala Arg Asn Leu Ser Phe Asn Glu Leu Tyr Pro Ser Gly Thr Leu Lys
                805                 810                 815 ctt cag tac aat ttt gat act att gac caa cag ttt tgt gac tta gct     2496
Leu Gln Tyr Asn Phe Asp Thr Ile Asp Gln Gln Phe Cys Asp Leu Ala
                820                 825                 830 gat aac aaa gac act gct gaa tgt gac att gct gaa gta gat ggg gaa     2544
Asp Asn Lys Asp Thr Ala Glu Cys Asp Ile Ala Glu Val Asp Gly Glu
                835                 840                 845 ctt ttt gtg gct caa agc aac ttt acc ttg ata ttg gaa ggt gaa gaa     2592
Leu Phe Val Ala Gln Ser Asn Phe Thr Leu Ile Leu Glu Gly Glu Glu
                850                 855                 860 gga gaa gtt gag cca ggt gat ttt gca tca tct gat gtg tta cct aaa     2640
Gly Glu Val Glu Pro Gly Asp Phe Ala Ser Ser Asp Val Leu Pro Lys
```

-continued

```
            865                 870                 875                 880 gca gct aac aca gca act gaa gaa aaa ctt gta tgc agt ggg gaa aat          2688
Ala Ala Asn Thr Ala Thr Glu Glu Lys Leu Val Cys Ser Gly Glu Asn
                    885                 890                 895 gat aat cat gga caa att gca aat ttg cca tct gcc gta act agt gac          2736
Asp Asn His Gly Gln Ile Ala Asn Leu Pro Ser Ala Val Thr Ser Asp
                    900                 905                 910 caa aag tcc caa aaa gta gac act tta cca tat gtg cct gaa cct att          2784
Gln Lys Ser Gln Lys Val Asp Thr Leu Pro Tyr Val Pro Glu Pro Ile
            915                 920                 925 aaa gta gca att gca gaa aat tta cta gat gta att aaa gac aca aga          2832
Lys Val Ala Ile Ala Glu Asn Leu Leu Asp Val Ile Lys Asp Thr Arg
930                 935                 940 agt aaa gaa att act tca gat aca atg gaa cag tcc att cat gaa aca          2880
Ser Lys Glu Ile Thr Ser Asp Thr Met Glu Gln Ser Ile His Glu Thr
945                 950                 955                 960 ata cct tta gtg agc caa aac ata atg tgt ccc act aaa ttg gtc aaa          2928
Ile Pro Leu Val Ser Gln Asn Ile Met Cys Pro Thr Lys Leu Val Lys
                    965                 970                 975 tct gca ttt aag act gct cag gaa aca agc aca atg act atg aat gtc          2976
Ser Ala Phe Lys Thr Ala Gln Glu Thr Ser Thr Met Thr Met Asn Val
                    980                 985                 990 agc cag gtt gat gac gtg gtt tcc tcc aaa act cgt acg aga ggt caa          3024
Ser Gln Val Asp Asp Val Val Ser Ser Lys Thr Arg Thr Arg Gly Gln
            995                 1000                1005 cgt atc caa aac gtg aat gtc aaa tca gca caa cag gaa gca tca              3069
Arg Ile Gln Asn Val Asn Val Lys Ser Ala Gln Gln Glu Ala Ser
    1010                1015                1020 gca gat gtt gct act cct aag atg cca ggg cag tca gtc agg aag              3114
Ala Asp Val Ala Thr Pro Lys Met Pro Gly Gln Ser Val Arg Lys
    1025                1030                1035 aaa act agg aag gca aaa gaa att tct gaa gct tct gaa aac atc              3159
Lys Thr Arg Lys Ala Lys Glu Ile Ser Glu Ala Ser Glu Asn Ile
    1040                1045                1050 tat tct gat gtc aga gga cta ttt cag aac cag caa ata cct caa              3204
Tyr Ser Asp Val Arg Gly Leu Phe Gln Asn Gln Gln Ile Pro Gln
    1055                1060                1065 aat tct gtt acg cct agg aga gga agg aga aag aaa gaa gtt aat              3249
Asn Ser Val Thr Pro Arg Arg Gly Arg Arg Lys Lys Glu Val Asn
    1070                1075                1080 cag gac ata cta gaa aac acc agt tct gtg gaa caa gaa tta cag              3294
Gln Asp Ile Leu Glu Asn Thr Ser Ser Val Glu Gln Glu Leu Gln
    1085                1090                1095 atc act aca ggt agg gaa tca aaa aga tta aaa tca tct cag ctg              3339
Ile Thr Thr Gly Arg Glu Ser Lys Arg Leu Lys Ser Ser Gln Leu
    1100                1105                1110 ttg gaa cca gca gtt gaa gaa act act aaa aaa gaa gtt aag gtt              3384
Leu Glu Pro Ala Val Glu Glu Thr Thr Lys Lys Glu Val Lys Val
    1115                1120                1125 tca tct gtt aca aaa agg act cct aga aga att aaa aga tct gta              3429
Ser Ser Val Thr Lys Arg Thr Pro Arg Arg Ile Lys Arg Ser Val
    1130                1135                1140 gaa aat cag gaa agt gtt gaa att ata aat gat cta aaa gtt agt              3474
Glu Asn Gln Glu Ser Val Glu Ile Ile Asn Asp Leu Lys Val Ser
    1145                1150                1155 acg gta aca agt cct agc aga atg atc aga aaa ttg aga agt act              3519
Thr Val Thr Ser Pro Ser Arg Met Ile Arg Lys Leu Arg Ser Thr
    1160                1165                1170 aat tta gat gct tct gaa aat aca gga aat aag caa gat gat aaa              3564
Asn Leu Asp Ala Ser Glu Asn Thr Gly Asn Lys Gln Asp Asp Lys
```

|     |     |     |     |     |     |     |     |     |     |     |     |     |     |      |
|-----|-----|-----|-----|-----|-----|-----|-----|-----|-----|-----|-----|-----|-----|------|
|     | 1175 |     |     |     | 1180 |     |     |     |     | 1185 |     |     |     |      |
| tcc | agt | gac | aag | cag | ctg | cgt | att | aaa | cat | gtt | aga | agg | gtc | aga | 3609 |
| Ser | Ser | Asp | Lys | Gln | Leu | Arg | Ile | Lys | His | Val | Arg | Arg | Val | Arg |      |
| 1190 |   |   |   |   | 1195 |   |   |   |   | 1200 |   |   |   |   |      |
| ggg | aga | gaa | gtt | agt | cca | tca | gat | gtg | aga | gaa | gac | tcc | aac | ctt | 3654 |
| Gly | Arg | Glu | Val | Ser | Pro | Ser | Asp | Val | Arg | Glu | Asp | Ser | Asn | Leu |      |
| 1205 |   |   |   |   | 1210 |   |   |   |   | 1215 |   |   |   |   |      |
| gag | tca | tct | cag | ttg | act | gtt | caa | gca | gaa | ttt | gat | atg | tct | gcc | 3699 |
| Glu | Ser | Ser | Gln | Leu | Thr | Val | Gln | Ala | Glu | Phe | Asp | Met | Ser | Ala |      |
| 1220 |   |   |   |   | 1225 |   |   |   |   | 1230 |   |   |   |   |      |
| ata | cct | aga | aaa | cgt | ggt | aga | cca | aga | aaa | atc | aat | cca | tct | gaa | 3744 |
| Ile | Pro | Arg | Lys | Arg | Gly | Arg | Pro | Arg | Lys | Ile | Asn | Pro | Ser | Glu |      |
| 1235 |   |   |   |   | 1240 |   |   |   |   | 1245 |   |   |   |   |      |
| gat | gta | gga | tct | aag | gct | gtt | aag | gaa | gag | aga | agc | ccc | aag | aag | 3789 |
| Asp | Val | Gly | Ser | Lys | Ala | Val | Lys | Glu | Glu | Arg | Ser | Pro | Lys | Lys |      |
| 1250 |   |   |   |   | 1255 |   |   |   |   | 1260 |   |   |   |   |      |
| aaa | gaa | gct | ccc | agc | att | aga | agg | aga | tct | aca | aga | aat | acc | cca | 3834 |
| Lys | Glu | Ala | Pro | Ser | Ile | Arg | Arg | Arg | Ser | Thr | Arg | Asn | Thr | Pro |      |
| 1265 |   |   |   |   | 1270 |   |   |   |   | 1275 |   |   |   |   |      |
| gct | aaa | agt | gaa | aat | gtt | gat | gtt | gga | aaa | cca | gct | tta | gga | aaa | 3879 |
| Ala | Lys | Ser | Glu | Asn | Val | Asp | Val | Gly | Lys | Pro | Ala | Leu | Gly | Lys |      |
| 1280 |   |   |   |   | 1285 |   |   |   |   | 1290 |   |   |   |   |      |
| tcc | att | tta | gtg | cca | aac | gag | gaa | ctt | tcg | atg | gtg | atg | agc | tct | 3924 |
| Ser | Ile | Leu | Val | Pro | Asn | Glu | Glu | Leu | Ser | Met | Val | Met | Ser | Ser |      |
| 1295 |   |   |   |   | 1300 |   |   |   |   | 1305 |   |   |   |   |      |
| aag | aaa | aaa | ctt | aca | aaa | aag | act | gaa | agt | caa | agc | caa | aaa | cgt | 3969 |
| Lys | Lys | Lys | Leu | Thr | Lys | Lys | Thr | Glu | Ser | Gln | Ser | Gln | Lys | Arg |      |
| 1310 |   |   |   |   | 1315 |   |   |   |   | 1320 |   |   |   |   |      |
| tca | ttg | cac | tca | gta | tca | gaa | gaa | cgc | aca | gat | gaa | atg | aca | cat | 4014 |
| Ser | Leu | His | Ser | Val | Ser | Glu | Glu | Arg | Thr | Asp | Glu | Met | Thr | His |      |
| 1325 |   |   |   |   | 1330 |   |   |   |   | 1335 |   |   |   |   |      |
| aaa | gaa | aca | aat | gag | cag | gaa | gaa | aga | ttg | ctc | gcc | aca | gct | tcc | 4059 |
| Lys | Glu | Thr | Asn | Glu | Gln | Glu | Glu | Arg | Leu | Leu | Ala | Thr | Ala | Ser |      |
| 1340 |   |   |   |   | 1345 |   |   |   |   | 1350 |   |   |   |   |      |
| ttc | act | aaa | tca | tcc | cgc | agc | agc | agg | act | cgg | tct | agc | aag | gcc | 4104 |
| Phe | Thr | Lys | Ser | Ser | Arg | Ser | Ser | Arg | Thr | Arg | Ser | Ser | Lys | Ala |      |
| 1355 |   |   |   |   | 1360 |   |   |   |   | 1365 |   |   |   |   |      |
| atc | ttg | ttg | ccg | gac | ctt | tct | gaa | cca | aac | aat | gag | cct | tta | ttt | 4149 |
| Ile | Leu | Leu | Pro | Asp | Leu | Ser | Glu | Pro | Asn | Asn | Glu | Pro | Leu | Phe |      |
| 1370 |   |   |   |   | 1375 |   |   |   |   | 1380 |   |   |   |   |      |
| tct | cca | gcg | tca | gaa | gtt | cca | agg | aaa | gca | aaa | gct | aaa | aaa | ata | 4194 |
| Ser | Pro | Ala | Ser | Glu | Val | Pro | Arg | Lys | Ala | Lys | Ala | Lys | Lys | Ile |      |
| 1385 |   |   |   |   | 1390 |   |   |   |   | 1395 |   |   |   |   |      |
| gag | gtt | cct | gca | cag | ctg | aaa | gaa | tta | gtt | tcg | gat | tta | tct | tct | 4239 |
| Glu | Val | Pro | Ala | Gln | Leu | Lys | Glu | Leu | Val | Ser | Asp | Leu | Ser | Ser |      |
| 1400 |   |   |   |   | 1405 |   |   |   |   | 1410 |   |   |   |   |      |
| cag | ttt | gtc | atc | tca | cct | cct | gct | tta | agg | agc | aga | caa | aaa | aac | 4284 |
| Gln | Phe | Val | Ile | Ser | Pro | Pro | Ala | Leu | Arg | Ser | Arg | Gln | Lys | Asn |      |
| 1415 |   |   |   |   | 1420 |   |   |   |   | 1425 |   |   |   |   |      |
| aca | tcc | aat | aag | aac | aag | ctt | gaa | gat | gaa | ctg | aaa | gat | gat | gca | 4329 |
| Thr | Ser | Asn | Lys | Asn | Lys | Leu | Glu | Asp | Glu | Leu | Lys | Asp | Asp | Ala |      |
| 1430 |   |   |   |   | 1435 |   |   |   |   | 1440 |   |   |   |   |      |
| caa | tca | gta | gaa | act | ctg | gga | aag | cca | aaa | gcg | aaa | cga | atc | agg | 4374 |
| Gln | Ser | Val | Glu | Thr | Leu | Gly | Lys | Pro | Lys | Ala | Lys | Arg | Ile | Arg |      |
| 1445 |   |   |   |   | 1450 |   |   |   |   | 1455 |   |   |   |   |      |
| acg | tca | aaa | aca | aaa | caa | gca | agc | aaa | aac | aca | gaa | aaa | gaa | agt | 4419 |
| Thr | Ser | Lys | Thr | Lys | Gln | Ala | Ser | Lys | Asn | Thr | Glu | Lys | Glu | Ser |      |
| 1460 |   |   |   |   | 1465 |   |   |   |   | 1470 |   |   |   |   |      |
| gct | tgg | tca | ctt | cct | ccc | ata | gaa | att | cgg | ctg | att | tcc | ccc | ttg | 4464 |
| Ala | Trp | Ser | Leu | Pro | Pro | Ile | Glu | Ile | Arg | Leu | Ile | Ser | Pro | Leu |      |

```
                    1475                   1480                   1485
gct  agc  cca  gct  gac  gga  gtc  aag  agc  aaa  cca  aga  aaa  act  aca           4509
Ala  Ser  Pro  Ala  Asp  Gly  Val  Lys  Ser  Lys  Pro  Arg  Lys  Thr  Thr
          1490                   1495                   1500 gaa  gtg  aca  gga  aca  ggt  ctt  gga  agg  aac  aga  aag  aaa  ctg  tct           4554
Glu  Val  Thr  Gly  Thr  Gly  Leu  Gly  Arg  Asn  Arg  Lys  Lys  Leu  Ser
     1505                   1510                   1515 tcc  tat  cca  aag  caa  att  tta  cgc  aga  aaa  atg  ctg  taatttcttg              4600
Ser  Tyr  Pro  Lys  Gln  Ile  Leu  Arg  Arg  Lys  Met  Leu
               1520                   1525             1530 ggaagatttt aatgtacacc tatttgtaaa gtcatcagaa tagtgtggat tattaaatat                   4660
ctagtttgga agaaataat ttatataaat tattgtaaat ttttatgtaa acagaaggtc                    4720
ttcaataagt aaagtaactc catatggagt gattgtttca gtccaggcaa tttttctatt                   4780
ttatattaag acttcataca tttatatatg taaatatggc ttattaatgg aatgttaaat                   4840
aaaatgtata cttctcaaaa aaaaaaaaaa aaaaaaaaa aaa                                      4883

<210> SEQ ID NO 6
<211> LENGTH: 1530
<212> TYPE: PRT
<213> ORGANISM: Homo sapiens

<400> SEQUENCE: 6

Glu Lys Leu Trp Lys Arg Asp Glu Gly Gly Thr Gly Lys Tyr Pro Pro
1               5                   10                  15

Ala Ser Leu His Ala Val Leu Asp Met Tyr Leu Leu Asp Gly Val Thr
            20                  25                  30

Glu Ala Ala Lys His Ser Ile Thr Ile Tyr Leu Leu Leu Asp Ile Met
        35                  40                  45

Tyr Ser Phe Pro Asn Lys Thr Asp Thr Pro Ile Glu Ser Phe Pro Thr
    50                  55                  60

Val Phe Ala Ile Ser Trp Gly Gln Val Lys Leu Ile Gln Gly Phe Trp
65                  70                  75                  80

Leu Ile Asp His Asn Asp Tyr Glu Ser Gly Leu Asp Leu Leu Phe His
                85                  90                  95

Pro Ala Thr Ala Lys Pro Leu Ser Trp Gln His Ser Lys Ile Ile Gln
            100                 105                 110

Ala Phe Met Ser Gln Gly Glu His Arg Gln Ala Leu Arg Tyr Ile Gln
        115                 120                 125

Thr Met Lys Pro Thr Val Ser Ser Gly Asn Asp Val Ile Leu His Leu
    130                 135                 140

Thr Val Leu Leu Phe Asn Arg Cys Met Val Glu Ala Trp Asn Phe Leu
145                 150                 155                 160

Arg Gln His Cys Asn Arg Leu Asn Ile Glu Glu Leu Leu Lys His Met
                165                 170                 175

Tyr Glu Val Cys Gln Glu Met Gly Leu Met Glu Asp Leu Leu Lys Leu
            180                 185                 190

Pro Phe Thr Asp Thr Glu Gln Glu Cys Leu Val Lys Phe Leu Gln Ser
        195                 200                 205

Ser Ala Ser Val Gln Asn His Glu Phe Leu Leu Val His His Leu Gln
    210                 215                 220

Arg Ala Asn Tyr Val Pro Ala Leu Lys Leu Asn Gln Thr Leu Lys Ile
225                 230                 235                 240

Asn Val Met Asn Asp Arg Asp Pro Arg Leu Arg Glu Arg Ser Leu Ala
                245                 250                 255
```

-continued

```
Arg Asn Ser Ile Leu Asp Gln Tyr Gly Lys Ile Leu Pro Arg Val His
            260                 265                 270

Arg Lys Leu Ala Ile Glu Arg Ala Lys Pro Tyr His Leu Ser Thr Ser
        275                 280                 285

Ser Val Phe Arg Leu Val Ser Arg Pro Lys Pro Leu Ser Ala Val Pro
290                 295                 300

Lys Gln Val Val Thr Gly Thr Val Leu Thr Arg Ser Val Phe Ile Asn
305                 310                 315                 320

Asn Val Leu Ser Lys Ile Gly Glu Val Trp Ala Ser Lys Glu Pro Ile
                325                 330                 335

Asn Ser Thr Thr Pro Phe Asn Ser Ser Lys Ile Glu Glu Pro Ser Pro
            340                 345                 350

Ile Val Tyr Ser Leu Pro Ala Pro Glu Leu Pro Glu Ala Phe Phe Gly
        355                 360                 365

Thr Pro Ile Ser Lys Ala Ser Gln Lys Ile Ser Arg Leu Leu Asp Leu
    370                 375                 380

Val Val Gln Pro Val Pro Arg Pro Ser Gln Cys Ser Glu Phe Ile Gln
385                 390                 395                 400

Gln Ser Ser Met Lys Ser Pro Leu Tyr Leu Val Ser Arg Ser Leu Pro
                405                 410                 415

Ser Ser Ser Gln Leu Lys Gly Ser Pro Gln Ala Ile Ser Arg Ala Ser
            420                 425                 430

Glu Leu His Leu Leu Glu Thr Pro Leu Val Val Lys Ala Lys Ser
        435                 440                 445

Leu Ala Met Ser Val Thr Thr Ser Gly Phe Ser Glu Phe Thr Pro Gln
    450                 455                 460

Ser Ile Leu Arg Ser Thr Pro Arg Ser Thr Pro Leu Ala Ser Pro Ser
465                 470                 475                 480

Pro Ser Pro Gly Arg Ser Pro Gln Arg Leu Lys Glu Thr Arg Ile Ser
                485                 490                 495

Phe Val Glu Glu Asp Val His Pro Lys Trp Ile Pro Gly Ala Ala Asp
            500                 505                 510

Asp Ser Lys Leu Glu Val Phe Thr Thr Pro Lys Lys Cys Ala Val Pro
        515                 520                 525

Val Glu Thr Glu Trp Pro Lys Ser Lys Asp Arg Thr Thr Ser Phe Phe
    530                 535                 540

Leu Asn Ser Pro Glu Lys Glu His Gln Glu Met Asp Glu Gly Ser Gln
545                 550                 555                 560

Ser Leu Glu Lys Leu Asp Val Ser Lys Gly Asn Ser Ser Val Ser Ile
                565                 570                 575

Thr Ser Asp Glu Thr Thr Leu Glu Tyr Gln Asp Ala Pro Ser Pro Glu
            580                 585                 590

Asp Leu Glu Glu Thr Val Phe Thr Ala Ser Lys Pro Lys Ser Ser Ser
        595                 600                 605

Thr Ala Leu Thr Thr Asn Val Thr Glu Gln Thr Glu Lys Asp Gly Asp
    610                 615                 620

Lys Asp Val Phe Ala Ser Glu Val Thr Pro Ser Asp Leu Gln Lys Gln
625                 630                 635                 640

Met Gly Asn Leu Glu Asp Ala Glu Thr Lys Asp Leu Leu Val Ala Ala
                645                 650                 655

Glu Ala Phe Ser Glu Leu Asn His Leu Ser Pro Val Gln Gly Thr Glu
            660                 665                 670

Ala Ser Leu Cys Ala Pro Ser Val Tyr Glu Gly Lys Ile Phe Thr Gln
        675                 680                 685
```

```
Lys Ser Lys Val Pro Val Leu Asp Glu Gly Leu Thr Ser Val Glu Thr
    690             695                 700

Tyr Thr Pro Ala Ile Arg Ala Asn Asp Asn Lys Ser Met Ala Asp Val
705             710                 715                 720

Leu Gly Asp Gly Gly Asn Ser Ser Leu Thr Ile Ser Glu Gly Pro Ile
                725                 730                 735

Val Ser Glu Arg Arg Leu Asn Gln Glu Val Ala Leu Asn Leu Lys Glu
            740                 745                 750

Asp His Glu Val Glu Val Gly Val Leu Lys Glu Ser Val Asp Leu Pro
        755                 760                 765

Glu Glu Lys Leu Pro Ile Ser Asp Ser Pro Pro Asp Thr Gln Glu Ile
    770                 775                 780

His Val Ile Glu Gln Glu Lys Leu Glu Ala Gln Asp Ser Gly Glu Glu
785                 790                 795                 800

Ala Arg Asn Leu Ser Phe Asn Glu Leu Tyr Pro Ser Gly Thr Leu Lys
                805                 810                 815

Leu Gln Tyr Asn Phe Asp Thr Ile Asp Gln Gln Phe Cys Asp Leu Ala
            820                 825                 830

Asp Asn Lys Asp Thr Ala Glu Cys Asp Ile Ala Glu Val Asp Gly Glu
        835                 840                 845

Leu Phe Val Ala Gln Ser Asn Phe Thr Leu Ile Leu Glu Gly Glu Glu
    850                 855                 860

Gly Glu Val Glu Pro Gly Asp Phe Ala Ser Ser Asp Val Leu Pro Lys
865                 870                 875                 880

Ala Ala Asn Thr Ala Thr Glu Glu Lys Leu Val Cys Ser Gly Glu Asn
                885                 890                 895

Asp Asn His Gly Gln Ile Ala Asn Leu Pro Ser Ala Val Thr Ser Asp
            900                 905                 910

Gln Lys Ser Gln Lys Val Asp Thr Leu Pro Tyr Val Pro Glu Pro Ile
        915                 920                 925

Lys Val Ala Ile Ala Glu Asn Leu Leu Asp Val Ile Lys Asp Thr Arg
    930                 935                 940

Ser Lys Glu Ile Thr Ser Asp Thr Met Glu Gln Ser Ile His Glu Thr
945                 950                 955                 960

Ile Pro Leu Val Ser Gln Asn Ile Met Cys Pro Thr Lys Leu Val Lys
                965                 970                 975

Ser Ala Phe Lys Thr Ala Gln Glu Thr Ser Thr Met Thr Met Asn Val
            980                 985                 990

Ser Gln Val Asp Asp Val Val Ser  Ser Lys Thr Arg Thr  Arg Gly Gln
        995                 1000                1005

Arg Ile  Gln Asn Val Asn Val  Lys Ser Ala Gln Gln  Glu Ala Ser
    1010                1015                1020

Ala Asp  Val Ala Thr Pro Lys  Met Pro Gly Gln Ser  Val Arg Lys
    1025                1030                1035

Lys Thr  Arg Lys Ala Lys Glu  Ile Ser Glu Ala Ser  Glu Asn Ile
    1040                1045                1050

Tyr Ser  Asp Val Arg Gly Leu  Phe Gln Asn Gln Gln  Ile Pro Gln
    1055                1060                1065

Asn Ser  Val Thr Pro Arg Arg  Gly Arg Arg Lys Lys  Glu Val Asn
    1070                1075                1080

Gln Asp  Ile Leu Glu Asn Thr  Ser Ser Val Glu Gln  Glu Leu Gln
    1085                1090                1095

Ile Thr  Thr Gly Arg Glu Ser  Lys Arg Leu Lys Ser  Ser Gln Leu
```

-continued

```
                1100                1105                1110
Leu Glu Pro Ala Val Glu Thr Thr Lys Lys Glu Val Lys Val
    1115                1120                1125

Ser Ser Val Thr Lys Arg Thr Pro Arg Arg Ile Lys Arg Ser Val
    1130                1135                1140

Glu Asn Gln Glu Ser Val Glu Ile Ile Asn Asp Leu Lys Val Ser
    1145                1150                1155

Thr Val Thr Ser Pro Ser Arg Met Ile Arg Lys Leu Arg Ser Thr
    1160                1165                1170

Asn Leu Asp Ala Ser Glu Asn Thr Gly Asn Lys Gln Asp Asp Lys
    1175                1180                1185

Ser Ser Asp Lys Gln Leu Arg Ile Lys His Val Arg Arg Val Arg
    1190                1195                1200

Gly Arg Glu Val Ser Pro Ser Asp Val Arg Glu Asp Ser Asn Leu
    1205                1210                1215

Glu Ser Ser Gln Leu Thr Val Gln Ala Glu Phe Asp Met Ser Ala
    1220                1225                1230

Ile Pro Arg Lys Arg Gly Arg Pro Arg Lys Ile Asn Pro Ser Glu
    1235                1240                1245

Asp Val Gly Ser Lys Ala Val Lys Glu Arg Ser Pro Lys Lys
    1250                1255                1260

Lys Glu Ala Pro Ser Ile Arg Arg Arg Ser Thr Arg Asn Thr Pro
    1265                1270                1275

Ala Lys Ser Glu Asn Val Asp Val Gly Lys Pro Ala Leu Gly Lys
    1280                1285                1290

Ser Ile Leu Val Pro Asn Glu Glu Leu Ser Met Val Met Ser Ser
    1295                1300                1305

Lys Lys Lys Leu Thr Lys Lys Thr Glu Ser Gln Ser Gln Lys Arg
    1310                1315                1320

Ser Leu His Ser Val Ser Glu Glu Arg Thr Asp Glu Met Thr His
    1325                1330                1335

Lys Glu Thr Asn Glu Gln Glu Glu Arg Leu Leu Ala Thr Ala Ser
    1340                1345                1350

Phe Thr Lys Ser Ser Arg Ser Ser Arg Thr Arg Ser Ser Lys Ala
    1355                1360                1365

Ile Leu Leu Pro Asp Leu Ser Glu Pro Asn Asn Glu Pro Leu Phe
    1370                1375                1380

Ser Pro Ala Ser Glu Val Pro Arg Lys Ala Lys Ala Lys Lys Ile
    1385                1390                1395

Glu Val Pro Ala Gln Leu Lys Glu Leu Val Ser Asp Leu Ser Ser
    1400                1405                1410

Gln Phe Val Ile Ser Pro Pro Ala Leu Arg Ser Arg Gln Lys Asn
    1415                1420                1425

Thr Ser Asn Lys Asn Lys Leu Glu Asp Glu Leu Lys Asp Asp Ala
    1430                1435                1440

Gln Ser Val Glu Thr Leu Gly Lys Pro Lys Ala Lys Arg Ile Arg
    1445                1450                1455

Thr Ser Lys Thr Lys Gln Ala Ser Lys Asn Thr Glu Lys Glu Ser
    1460                1465                1470

Ala Trp Ser Leu Pro Pro Ile Glu Ile Arg Leu Ile Ser Pro Leu
    1475                1480                1485

Ala Ser Pro Ala Asp Gly Val Lys Ser Lys Ser Pro Arg Lys Thr Thr
    1490                1495                1500
```

-continued

```
Glu Val Thr Gly Thr Gly Leu Gly Arg Asn Arg Lys Lys Leu Ser
    1505                1510                1515

Ser Tyr Pro Lys Gln Ile Leu Arg Arg Lys Met Leu
    1520                1525                1530

<210> SEQ ID NO 7
<211> LENGTH: 4115
<212> TYPE: DNA
<213> ORGANISM: Mus musculus
<220> FEATURE:
<221> NAME/KEY: CDS
<222> LOCATION: (2)..(3817)
<220> FEATURE:
<221> NAME/KEY: misc_feature
<222> LOCATION: (3101)..(3101)
<223> OTHER INFORMATION: n is a, c, g, or t

<400> SEQUENCE: 7 t cag att ctg aag aat aat ctc atg agt gat cgt gac cct cga ttg cgg      49
  Gln Ile Leu Lys Asn Asn Leu Met Ser Asp Arg Asp Pro Arg Leu Arg
  1               5                   10                  15 gaa aga tcg gtg act cga aat tct ata tta gac cag tat ggg aaa atc       97
Glu Arg Ser Val Thr Arg Asn Ser Ile Leu Asp Gln Tyr Gly Lys Ile
                20                  25                  30 cta cct aga gtc cag aga aag tta gct gtt gag cga gct aag cct tac      145
Leu Pro Arg Val Gln Arg Lys Leu Ala Val Glu Arg Ala Lys Pro Tyr
            35                  40                  45 cac ctg tcg aca tcc tca gtt ttt cat gaa gtt tct aga ccc aaa ccg      193
His Leu Ser Thr Ser Ser Val Phe His Glu Val Ser Arg Pro Lys Pro
        50                  55                  60 tta tcg gca ttt cca aag aaa gct ata act gga aca gtg tta acc cga      241
Leu Ser Ala Phe Pro Lys Lys Ala Ile Thr Gly Thr Val Leu Thr Arg
65                  70                  75                  80 tct acg ttc atc agc aat gtt tta tct aaa att gga gag gtg tgg gca      289
Ser Thr Phe Ile Ser Asn Val Leu Ser Lys Ile Gly Glu Val Trp Ala
                85                  90                  95 agt cat gag cct aga aat ggc gtc tca ctt ttt aac agt cct aaa aca      337
Ser His Glu Pro Arg Asn Gly Val Ser Leu Phe Asn Ser Pro Lys Thr
            100                 105                 110 gaa cag cca tct cct gta gta cac tct ttc cca cac cca gag ctt cct      385
Glu Gln Pro Ser Pro Val Val His Ser Phe Pro His Pro Glu Leu Pro
        115                 120                 125 gag gcg ttt gtt gga act cca att tca aat aca tcc cag aga att tct      433
Glu Ala Phe Val Gly Thr Pro Ile Ser Asn Thr Ser Gln Arg Ile Ser
    130                 135                 140 aga tta ctg gat ttg gtt gtc cat cct gta ccc cag cct tct cag tgt      481
Arg Leu Leu Asp Leu Val Val His Pro Val Pro Gln Pro Ser Gln Cys
145                 150                 155                 160 ttg gag ttt att caa caa agt ccc aca aga tct cct ttg tgt ctg ctg      529
Leu Glu Phe Ile Gln Gln Ser Pro Thr Arg Ser Pro Leu Cys Leu Leu
                165                 170                 175 tcc agt tcg tta cca tta agt tca cag ttt aaa agg cca cat cag aat      577
Ser Ser Ser Leu Pro Leu Ser Ser Gln Phe Lys Arg Pro His Gln Asn
            180                 185                 190 acc tcc agg cct tca gag ttg ctt tta ctt gag act cct ctc ata gtt      625
Thr Ser Arg Pro Ser Glu Leu Leu Leu Leu Glu Thr Pro Leu Ile Val
        195                 200                 205 aag aaa gct aaa tct ttg gct ctg tca gcc acg tct tct gga ttt gcc      673
Lys Lys Ala Lys Ser Leu Ala Leu Ser Ala Thr Ser Ser Gly Phe Ala
    210                 215                 220 gag ttt act cct cca tcc atc ctt agg tct ggt ttt cga aca aca cct      721
Glu Phe Thr Pro Pro Ser Ile Leu Arg Ser Gly Phe Arg Thr Thr Pro
225                 230                 235                 240
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| tta | gca | tct | ccc | tct | ttg | tca | cct | gga | aga | tct | ctc | act | ccg | cct | ttc | 769  |
| Leu | Ala | Ser | Pro | Ser | Leu | Ser | Pro | Gly | Arg | Ser | Leu | Thr | Pro | Pro | Phe |      |
|     |     |     |     | 245 |     |     |     |     | 250 |     |     |     |     | 255 |     |      |
| aga | gtt | aaa | gaa | aca | agg | att | tca | ttc | atg | gaa | gaa | ggc | atg | aat | aca | 817  |
| Arg | Val | Lys | Glu | Thr | Arg | Ile | Ser | Phe | Met | Glu | Glu | Gly | Met | Asn | Thr |      |
|     |     |     | 260 |     |     |     |     | 265 |     |     |     |     | 270 |     |     |      |
| cac | tgg | act | gat | aga | gct | aca | gat | gac | cga | aat | aca | aaa | gcg | ttt | gtt | 865  |
| His | Trp | Thr | Asp | Arg | Ala | Thr | Asp | Asp | Arg | Asn | Thr | Lys | Ala | Phe | Val |      |
|     |     | 275 |     |     |     |     | 280 |     |     |     |     | 285 |     |     |     |      |
| agc | aca | tct | ttc | cat | aaa | tgt | gga | ctt | cca | gca | gaa | act | gag | tgg | atg | 913  |
| Ser | Thr | Ser | Phe | His | Lys | Cys | Gly | Leu | Pro | Ala | Glu | Thr | Glu | Trp | Met |      |
|     | 290 |     |     |     |     | 295 |     |     |     |     | 300 |     |     |     |     |      |
| aag | acc | agt | gat | aag | aat | aca | tat | ttt | cct | ctg | gat | gtc | cct | gca | aag | 961  |
| Lys | Thr | Ser | Asp | Lys | Asn | Thr | Tyr | Phe | Pro | Leu | Asp | Val | Pro | Ala | Lys |      |
| 305 |     |     |     |     | 310 |     |     |     |     | 315 |     |     |     |     | 320 |      |
| ggc | cct | cag | aaa | gtg | gtg | gca | gag | tca | ctg | gct | acc | cat | tca | gga | agg | 1009 |
| Gly | Pro | Gln | Lys | Val | Val | Ala | Glu | Ser | Leu | Ala | Thr | His | Ser | Gly | Arg |      |
|     |     |     |     | 325 |     |     |     |     | 330 |     |     |     |     | 335 |     |      |
| ctg | gag | aaa | ctg | gat | gtg | agc | aaa | gaa | gac | agc | aca | gct | tcc | acc | agg | 1057 |
| Leu | Glu | Lys | Leu | Asp | Val | Ser | Lys | Glu | Asp | Ser | Thr | Ala | Ser | Thr | Arg |      |
|     |     |     | 340 |     |     |     |     | 345 |     |     |     |     | 350 |     |     |      |
| tca | gac | cag | acc | tcc | tta | gag | tat | cat | gac | gca | cca | tca | cca | gaa | gac | 1105 |
| Ser | Asp | Gln | Thr | Ser | Leu | Glu | Tyr | His | Asp | Ala | Pro | Ser | Pro | Glu | Asp |      |
|     |     | 355 |     |     |     |     | 360 |     |     |     |     | 365 |     |     |     |      |
| ttg | gaa | ggt | gct | gtt | ttt | gtg | tct | ccc | aag | cca | gca | tct | tcc | tcc | act | 1153 |
| Leu | Glu | Gly | Ala | Val | Phe | Val | Ser | Pro | Lys | Pro | Ala | Ser | Ser | Ser | Thr |      |
|     | 370 |     |     |     |     | 375 |     |     |     |     | 380 |     |     |     |     |      |
| gaa | cta | act | act | aat | tca | act | cta | caa | aca | gag | agg | gat | aat | gat | aaa | 1201 |
| Glu | Leu | Thr | Thr | Asn | Ser | Thr | Leu | Gln | Thr | Glu | Arg | Asp | Asn | Asp | Lys |      |
| 385 |     |     |     |     | 390 |     |     |     |     | 395 |     |     |     |     | 400 |      |
| gat | gcg | ttt | aag | tca | gaa | ggt | act | cct | tca | ccc | gtg | aag | aaa | caa | ata | 1249 |
| Asp | Ala | Phe | Lys | Ser | Glu | Gly | Thr | Pro | Ser | Pro | Val | Lys | Lys | Gln | Ile |      |
|     |     |     |     | 405 |     |     |     |     | 410 |     |     |     |     | 415 |     |      |
| ggc | acg | gga | gac | gct | gca | gtg | gaa | gca | ttt | tca | gaa | ctg | agt | cgc | tta | 1297 |
| Gly | Thr | Gly | Asp | Ala | Ala | Val | Glu | Ala | Phe | Ser | Glu | Leu | Ser | Arg | Leu |      |
|     |     |     | 420 |     |     |     |     | 425 |     |     |     |     | 430 |     |     |      |
| gac | cct | gtt | gaa | aga | gct | gaa | gct | tct | ttt | ggt | gtg | tcg | tca | gtc | tgt | 1345 |
| Asp | Pro | Val | Glu | Arg | Ala | Glu | Ala | Ser | Phe | Gly | Val | Ser | Ser | Val | Cys |      |
|     |     | 435 |     |     |     |     | 440 |     |     |     |     | 445 |     |     |     |      |
| gaa | ggg | gaa | acc | tcc | act | tca | aac | tcc | aag | acg | tca | gtt | ctg | gat | gga | 1393 |
| Glu | Gly | Glu | Thr | Ser | Thr | Ser | Asn | Ser | Lys | Thr | Ser | Val | Leu | Asp | Gly |      |
|     | 450 |     |     |     |     | 455 |     |     |     |     | 460 |     |     |     |     |      |
| atc | gtg | cct | att | gag | agc | cga | acc | tcc | ata | ctt | aca | gca | gac | cac | aaa | 1441 |
| Ile | Val | Pro | Ile | Glu | Ser | Arg | Thr | Ser | Ile | Leu | Thr | Ala | Asp | His | Lys |      |
| 465 |     |     |     |     | 470 |     |     |     |     | 475 |     |     |     |     | 480 |      |
| gag | tct | gtg | gcc | aac | acg | gtt | gca | gat | gtt | gaa | agc | tct | ggg | tcc | acc | 1489 |
| Glu | Ser | Val | Ala | Asn | Thr | Val | Ala | Asp | Val | Glu | Ser | Ser | Gly | Ser | Thr |      |
|     |     |     |     | 485 |     |     |     |     | 490 |     |     |     |     | 495 |     |      |
| agc | tcc | aag | tgc | ccg | gtt | acc | tct | gaa | cgc | agc | ctc | ggc | caa | aaa | cta | 1537 |
| Ser | Ser | Lys | Cys | Pro | Val | Thr | Ser | Glu | Arg | Ser | Leu | Gly | Gln | Lys | Leu |      |
|     |     | 500 |     |     |     |     | 505 |     |     |     |     | 510 |     |     |     |      |
| aca | tta | aac | tta | aaa | gaa | gat | gaa | ata | gaa | gct | cat | gta | cca | aag | gag | 1585 |
| Thr | Leu | Asn | Leu | Lys | Glu | Asp | Glu | Ile | Glu | Ala | His | Val | Pro | Lys | Glu |      |
|     | 515 |     |     |     |     | 520 |     |     |     |     | 525 |     |     |     |     |      |
| aac | gtt | ggt | tta | cca | gaa | gaa | agc | cct | cga | att | tct | gct | gct | cct | tct | 1633 |
| Asn | Val | Gly | Leu | Pro | Glu | Glu | Ser | Pro | Arg | Ile | Ser | Ala | Ala | Pro | Ser |      |
| 530 |     |     |     |     | 535 |     |     |     |     | 540 |     |     |     |     |     |      |
| gat | act | cac | gag | att | cat | cta | att | gga | tgt | gaa | aat | ctt | gaa | gtt | caa | 1681 |
| Asp | Thr | His | Glu | Ile | His | Leu | Ile | Gly | Cys | Glu | Asn | Leu | Glu | Val | Gln |      |
| 545 |     |     |     |     | 550 |     |     |     |     | 555 |     |     |     |     | 560 |      |

```
aat tca gaa gag gag gcc aag aat ctt tca ttt gat gag ttg tat ccc    1729
Asn Ser Glu Glu Glu Ala Lys Asn Leu Ser Phe Asp Glu Leu Tyr Pro
            565                 570                 575 tta ggg gca gag aaa ctt gag tat aat ctc agt act att gag cag cag    1777
Leu Gly Ala Glu Lys Leu Glu Tyr Asn Leu Ser Thr Ile Glu Gln Gln
        580                 585                 590 ttt tgt gac ttg cct gat gac aaa gac tct gct gaa tgt gat gct gct    1825
Phe Cys Asp Leu Pro Asp Asp Lys Asp Ser Ala Glu Cys Asp Ala Ala
    595                 600                 605 gaa gta gac ggg gaa ctt ttt gtg gcc cag agc aac ttt acc ctg att    1873
Glu Val Asp Gly Glu Leu Phe Val Ala Gln Ser Asn Phe Thr Leu Ile
610                 615                 620 tta gaa ggt gaa gaa gga gaa gct gag gca agc gac tct gca gca cct    1921
Leu Glu Gly Glu Glu Gly Glu Ala Glu Ala Ser Asp Ser Ala Ala Pro
625                 630                 635                 640 aat atg tta ccg aaa tcg acc aag gaa aaa cct gtg tgc tac agg gaa    1969
Asn Met Leu Pro Lys Ser Thr Lys Glu Lys Pro Val Cys Tyr Arg Glu
                645                 650                 655 ccc cat aat cag gag cgc gtt aca gat ttg cca tct gct gtg act gct    2017
Pro His Asn Gln Glu Arg Val Thr Asp Leu Pro Ser Ala Val Thr Ala
            660                 665                 670 gac caa gaa tcc cac aag gta gag act tta ccg tat gtg cct gaa ccg    2065
Asp Gln Glu Ser His Lys Val Glu Thr Leu Pro Tyr Val Pro Glu Pro
        675                 680                 685 gtt aaa gtg gca att gca gaa aat ctg ttg gat gta att aaa gac acc    2113
Val Lys Val Ala Ile Ala Glu Asn Leu Leu Asp Val Ile Lys Asp Thr
    690                 695                 700 aga agt aag gaa gca act ccc gtg gca gca ggt gag gct ggt gat gag    2161
Arg Ser Lys Glu Ala Thr Pro Val Ala Ala Gly Glu Ala Gly Asp Glu
705                 710                 715                 720 gac gga gca gtg ata gtc tca aag gct gca cat tcg tcc agg ctg aca    2209
Asp Gly Ala Val Ile Val Ser Lys Ala Ala His Ser Ser Arg Leu Thr
                725                 730                 735 aac tct aca ccg aag act gtt aag gaa cca cgt gca gag act gta aat    2257
Asn Ser Thr Pro Lys Thr Val Lys Glu Pro Arg Ala Glu Thr Val Asn
            740                 745                 750 acc agc cag agt gat gac atg gtt tct tct aga act ctc aca aga agg    2305
Thr Ser Gln Ser Asp Asp Met Val Ser Ser Arg Thr Leu Thr Arg Arg
        755                 760                 765 cag cat gcc cta agc ctg aat gtc aca tca gaa caa gag cct tca gca    2353
Gln His Ala Leu Ser Leu Asn Val Thr Ser Glu Gln Glu Pro Ser Ala
    770                 775                 780 gtt gcc act cct aag aag aga act aga aaa att aaa gaa act cct gag    2401
Val Ala Thr Pro Lys Lys Arg Thr Arg Lys Ile Lys Glu Thr Pro Glu
785                 790                 795                 800 tct tct gaa agg acc tgt tct gac cta aaa gta gca cct gag aac caa    2449
Ser Ser Glu Arg Thr Cys Ser Asp Leu Lys Val Ala Pro Glu Asn Gln
                805                 810                 815 ctg aca gct cag aat cct ccc gct cct agg aga aga aag aag aag gac    2497
Leu Thr Ala Gln Asn Pro Pro Ala Pro Arg Arg Arg Lys Lys Lys Asp
            820                 825                 830 gtt agc caa ggc aca ctg cca agt tct ggt gct gtg gag ccg gag ccg    2545
Val Ser Gln Gly Thr Leu Pro Ser Ser Gly Ala Val Glu Pro Glu Pro
        835                 840                 845 gaa cct cag ggt acg ccg gga aga ctg agg ctg aga acg cag cca ccc    2593
Glu Pro Gln Gly Thr Pro Gly Arg Leu Arg Leu Arg Thr Gln Pro Pro
    850                 855                 860 gag cca gca gct gaa gaa act cct tct aga aca aaa gtc agg ctt tca    2641
Glu Pro Ala Ala Glu Glu Thr Pro Ser Arg Thr Lys Val Arg Leu Ser
865                 870                 875                 880
```

```
tct gtt aga aag gga acc cct aga aga ctt aag aag tct gta gaa aat    2689
Ser Val Arg Lys Gly Thr Pro Arg Arg Leu Lys Lys Ser Val Glu Asn
            885                 890                 895 ggg caa agt ata gaa att cta gat gat ctc aaa ggg agt gag gca gca    2737
Gly Gln Ser Ile Glu Ile Leu Asp Asp Leu Lys Gly Ser Glu Ala Ala
        900                 905                 910 agt cat gac ggg act gtc aca gag ctg agg aat gcc aat tta gaa gat    2785
Ser His Asp Gly Thr Val Thr Glu Leu Arg Asn Ala Asn Leu Glu Asp
    915                 920                 925 act cag aat atg gag tat aaa caa gat gaa cac agt gac cag caa ccg    2833
Thr Gln Asn Met Glu Tyr Lys Gln Asp Glu His Ser Asp Gln Gln Pro
930                 935                 940 cct cta aaa cga aag agg gtc aga gag aga gaa gtt agt gtg tca agt    2881
Pro Leu Lys Arg Lys Arg Val Arg Glu Arg Glu Val Ser Val Ser Ser
945                 950                 955                 960 gtg aca gaa gag cca aag ctt gac tca tcc cag ttg cct ctt cag aca    2929
Val Thr Glu Glu Pro Lys Leu Asp Ser Ser Gln Leu Pro Leu Gln Thr
                965                 970                 975 gga ctc gat gta cct gcc acc cct agg aaa cgt ggt aga ccc agg aag    2977
Gly Leu Asp Val Pro Ala Thr Pro Arg Lys Arg Gly Arg Pro Arg Lys
            980                 985                 990 gta gtt ccc tta gaa gct gac ggt ggc aca act ggt aag gaa cag aca    3025
Val Val Pro Leu Glu Ala Asp Gly Gly Thr Thr Gly Lys Glu Gln Thr
        995                 1000                1005 agt cct cag aag aaa gat gtt ccg gtt gtc cgg aga tct aca cgg        3070
Ser Pro Gln Lys Lys Asp Val Pro Val Val Arg Arg Ser Thr Arg
    1010                1015                1020 aac acc cca gct aga aat gtg agt act tta naa aaa tca gtt tta        3115
Asn Thr Pro Ala Arg Asn Val Ser Thr Leu Xaa Lys Ser Val Leu
1025                1030                1035 gtg cca aat aag gaa gct gct cta gtg gtg aca tct aag agg aga        3160
Val Pro Asn Lys Glu Ala Ala Leu Val Val Thr Ser Lys Arg Arg
    1040                1045                1050 cct aca aag aag tct gca gag gaa agc tca aaa gat cca tca gcg        3205
Pro Thr Lys Lys Ser Ala Glu Glu Ser Ser Lys Asp Pro Ser Ala
1055                1060                1065 gca gtc tca gac tgg gcg ggt gga gca gcc cac aca gag tcc gct        3250
Ala Val Ser Asp Trp Ala Gly Gly Ala Ala His Thr Glu Ser Ala
    1070                1075                1080 gac cga agg gac gga ctg ctt gcc gcc gct gct ctc acg cca tct        3295
Asp Arg Arg Asp Gly Leu Leu Ala Ala Ala Ala Leu Thr Pro Ser
1085                1090                1095 gcc cag ggc aca agg act agg tct aga agg acc atg ttg ttg acg        3340
Ala Gln Gly Thr Arg Thr Arg Ser Arg Arg Thr Met Leu Leu Thr
    1100                1105                1110 gac att tct gaa ccc aaa act gag cct tta ttt cct cct cct tca        3385
Asp Ile Ser Glu Pro Lys Thr Glu Pro Leu Phe Pro Pro Pro Ser
1115                1120                1125 gtg aag gtt cca aag aaa aaa tca aaa gct gag aac atg gag gcc        3430
Val Lys Val Pro Lys Lys Lys Ser Lys Ala Glu Asn Met Glu Ala
    1130                1135                1140 gca gcc cag ctg aaa gaa ttg gtg tca gat tta tct tct cag ttt        3475
Ala Ala Gln Leu Lys Glu Leu Val Ser Asp Leu Ser Ser Gln Phe
1145                1150                1155 gtt gtt tcc cct cct gcc ttg aga acc agg cag aaa agt ata tcc        3520
Val Val Ser Pro Pro Ala Leu Arg Thr Arg Gln Lys Ser Ile Ser
    1160                1165                1170 aat act tcc aag ctt cta ggt gaa ctg gag agt gac cct aaa cca        3565
Asn Thr Ser Lys Leu Leu Gly Glu Leu Glu Ser Asp Pro Lys Pro
1175                1180                1185
```

-continued

```
tta gag atc ata gaa caa aaa cca aaa aga agc agg act gtg aag       3610
Leu Glu Ile Ile Glu Gln Lys Pro Lys Arg Ser Arg Thr Val Lys
    1190                1195                1200 aca aga gca agc aga aac aca gga aaa gga agt tct tgg tca cct       3655
Thr Arg Ala Ser Arg Asn Thr Gly Lys Gly Ser Ser Trp Ser Pro
1205                1210                1215 cct cct gta gaa att aag ctg gtt tct ccc ttg gcg agt cca gtg       3700
Pro Pro Val Glu Ile Lys Leu Val Ser Pro Leu Ala Ser Pro Val
        1220                1225                1230 gat gaa ata aag acc ggc aag cca aga aaa act gca gaa ata gca       3745
Asp Glu Ile Lys Thr Gly Lys Pro Arg Lys Thr Ala Glu Ile Ala
1235                1240                1245 gga aaa act ctt gga agg ggc aga aag aag cca tct tct ttt cca       3790
Gly Lys Thr Leu Gly Arg Gly Arg Lys Lys Pro Ser Ser Phe Pro
    1250                1255                1260 aag caa att tta cgc agg aaa atg ctg taattttag cccaagattt         3837
Lys Gln Ile Leu Arg Arg Lys Met Leu
        1265                1270 taacacgcac ctgtttgtaa aagtcaacag tatttgtgtg gattattaaa gtcaccaatt 3897 tggatgaaaa tacttatat aaattgtaca attttgtaag cagtaaatga gtaactccac  3957
atggagtgca gttcttgtag tgcaggcgtt ttatacgact tgatgcgttt atatcaatgt 4017 aaatatgact tatcattggg aggttaaata aactactgta aagtaaaaaa aaaaaaaaaa 4077 aaaaaaaaaa aaaaaaaaaa aaaaaaaaaa aaaaaaa                         4115
```

<210> SEQ ID NO 8
<211> LENGTH: 1272
<212> TYPE: PRT
<213> ORGANISM: Mus musculus
<220> FEATURE:
<221> NAME/KEY: misc_feature
<222> LOCATION: (1034)..(1034)
<223> OTHER INFORMATION: The 'Xaa' at location 1034 stands for Lys, Glu, or Gln.

<400> SEQUENCE: 8

```
Gln Ile Leu Lys Asn Asn Leu Met Ser Asp Arg Asp Pro Arg Leu Arg
1               5                   10                  15

Glu Arg Ser Val Thr Arg Asn Ser Ile Leu Asp Gln Tyr Gly Lys Ile
            20                  25                  30

Leu Pro Arg Val Gln Arg Lys Leu Ala Val Glu Arg Ala Lys Pro Tyr
        35                  40                  45

His Leu Ser Thr Ser Ser Val Phe His Glu Val Ser Arg Pro Lys Pro
    50                  55                  60

Leu Ser Ala Phe Pro Lys Lys Ala Ile Thr Gly Thr Val Leu Thr Arg
65                  70                  75                  80

Ser Thr Phe Ile Ser Asn Val Leu Ser Lys Ile Gly Glu Val Trp Ala
                85                  90                  95

Ser His Glu Pro Arg Asn Gly Val Ser Leu Phe Asn Ser Pro Lys Thr
            100                 105                 110

Glu Gln Pro Ser Pro Val Val His Ser Phe Pro His Pro Glu Leu Pro
        115                 120                 125

Glu Ala Phe Val Gly Thr Pro Ile Ser Asn Thr Ser Gln Arg Ile Ser
    130                 135                 140

Arg Leu Leu Asp Leu Val Val His Pro Val Pro Gln Pro Ser Gln Cys
145                 150                 155                 160

Leu Glu Phe Ile Gln Gln Ser Pro Thr Arg Ser Pro Leu Cys Leu Leu
                165                 170                 175
```

-continued

```
Ser Ser Ser Leu Pro Leu Ser Ser Gln Phe Lys Arg Pro His Gln Asn
            180                 185                 190

Thr Ser Arg Pro Ser Glu Leu Leu Leu Glu Thr Pro Leu Ile Val
        195                 200                 205

Lys Lys Ala Lys Ser Leu Ala Leu Ser Ala Thr Ser Ser Gly Phe Ala
210                 215                 220

Glu Phe Thr Pro Pro Ser Ile Leu Arg Ser Gly Phe Arg Thr Thr Pro
225                 230                 235                 240

Leu Ala Ser Pro Ser Leu Ser Pro Gly Arg Ser Leu Thr Pro Pro Phe
                245                 250                 255

Arg Val Lys Glu Thr Arg Ile Ser Phe Met Glu Gly Met Asn Thr
            260                 265                 270

His Trp Thr Asp Arg Ala Thr Asp Asp Arg Asn Thr Lys Ala Phe Val
        275                 280                 285

Ser Thr Ser Phe His Lys Cys Gly Leu Pro Ala Glu Thr Glu Trp Met
        290                 295                 300

Lys Thr Ser Asp Lys Asn Thr Tyr Phe Pro Leu Asp Val Pro Ala Lys
305                 310                 315                 320

Gly Pro Gln Lys Val Ala Glu Ser Leu Ala Thr His Ser Gly Arg
            325                 330                 335

Leu Glu Lys Leu Asp Val Ser Lys Glu Asp Ser Thr Ala Ser Thr Arg
            340                 345                 350

Ser Asp Gln Thr Ser Leu Glu Tyr His Asp Ala Pro Ser Pro Glu Asp
            355                 360                 365

Leu Glu Gly Ala Val Phe Val Ser Pro Lys Pro Ala Ser Ser Ser Thr
    370                 375                 380

Glu Leu Thr Thr Asn Ser Thr Leu Gln Thr Glu Arg Asp Asn Asp Lys
385                 390                 395                 400

Asp Ala Phe Lys Ser Glu Gly Thr Pro Ser Pro Val Lys Lys Gln Ile
            405                 410                 415

Gly Thr Gly Asp Ala Ala Val Glu Ala Phe Ser Glu Leu Ser Arg Leu
            420                 425                 430

Asp Pro Val Glu Arg Ala Glu Ala Ser Phe Gly Val Ser Ser Val Cys
            435                 440                 445

Glu Gly Glu Thr Ser Thr Ser Asn Ser Lys Thr Ser Val Leu Asp Gly
            450                 455                 460

Ile Val Pro Ile Glu Ser Arg Thr Ser Ile Leu Thr Ala Asp His Lys
465                 470                 475                 480

Glu Ser Val Ala Asn Thr Val Ala Asp Val Glu Ser Ser Gly Ser Thr
                485                 490                 495

Ser Ser Lys Cys Pro Val Thr Ser Glu Arg Ser Leu Gly Gln Lys Leu
            500                 505                 510

Thr Leu Asn Leu Lys Glu Asp Glu Ile Glu Ala His Val Pro Lys Glu
            515                 520                 525

Asn Val Gly Leu Pro Glu Glu Ser Pro Arg Ile Ser Ala Ala Pro Ser
            530                 535                 540

Asp Thr His Glu Ile His Leu Ile Gly Cys Glu Asn Leu Glu Val Gln
545                 550                 555                 560

Asn Ser Glu Glu Glu Ala Lys Asn Leu Ser Phe Asp Glu Leu Tyr Pro
                565                 570                 575

Leu Gly Ala Glu Lys Leu Glu Tyr Asn Leu Ser Thr Ile Glu Gln Gln
            580                 585                 590

Phe Cys Asp Leu Pro Asp Asp Lys Asp Ser Ala Glu Cys Asp Ala Ala
```

```
                595                 600                 605
    Glu Val Asp Gly Glu Leu Phe Val Ala Gln Ser Asn Phe Thr Leu Ile
        610                 615                 620

Leu Glu Gly Glu Glu Gly Glu Ala Glu Ala Ser Asp Ser Ala Ala Pro
    625                 630                 635                 640

Asn Met Leu Pro Lys Ser Thr Lys Glu Lys Pro Val Cys Tyr Arg Glu
                    645                 650                 655

Pro His Asn Gln Glu Arg Val Thr Asp Leu Pro Ser Ala Val Thr Ala
                660                 665                 670

Asp Gln Glu Ser His Lys Val Glu Thr Leu Pro Tyr Val Pro Glu Pro
            675                 680                 685

Val Lys Val Ala Ile Ala Glu Asn Leu Leu Asp Val Ile Lys Asp Thr
    690                 695                 700

Arg Ser Lys Glu Ala Thr Pro Val Ala Gly Glu Ala Gly Asp Glu
    705                 710                 715                 720

Asp Gly Ala Val Ile Val Ser Lys Ala Ala His Ser Ser Arg Leu Thr
                    725                 730                 735

Asn Ser Thr Pro Lys Thr Val Lys Glu Pro Arg Ala Glu Thr Val Asn
                740                 745                 750

Thr Ser Gln Ser Asp Asp Met Val Ser Ser Arg Thr Leu Thr Arg Arg
            755                 760                 765

Gln His Ala Leu Ser Leu Asn Val Thr Ser Glu Gln Glu Pro Ser Ala
        770                 775                 780

Val Ala Thr Pro Lys Lys Arg Thr Arg Lys Ile Lys Glu Thr Pro Glu
    785                 790                 795                 800

Ser Ser Glu Arg Thr Cys Ser Asp Leu Lys Val Ala Pro Glu Asn Gln
                    805                 810                 815

Leu Thr Ala Gln Asn Pro Pro Ala Pro Arg Arg Arg Lys Lys Lys Asp
                820                 825                 830

Val Ser Gln Gly Thr Leu Pro Ser Ser Gly Ala Val Glu Pro Glu Pro
            835                 840                 845

Glu Pro Gln Gly Thr Pro Gly Arg Leu Arg Leu Arg Thr Gln Pro Pro
    850                 855                 860

Glu Pro Ala Ala Glu Glu Thr Pro Ser Arg Thr Lys Val Arg Leu Ser
    865                 870                 875                 880

Ser Val Arg Lys Gly Thr Pro Arg Arg Leu Lys Lys Ser Val Glu Asn
                    885                 890                 895

Gly Gln Ser Ile Glu Ile Leu Asp Asp Leu Lys Gly Ser Glu Ala Ala
                900                 905                 910

Ser His Asp Gly Thr Val Thr Glu Leu Arg Asn Ala Asn Leu Glu Asp
            915                 920                 925

Thr Gln Asn Met Glu Tyr Lys Gln Asp Glu His Ser Asp Gln Gln Pro
    930                 935                 940

Pro Leu Lys Arg Lys Arg Val Arg Glu Arg Val Ser Val Ser Ser
    945                 950                 955                 960

Val Thr Glu Glu Pro Lys Leu Asp Ser Ser Gln Leu Pro Leu Gln Thr
                    965                 970                 975

Gly Leu Asp Val Pro Ala Thr Pro Arg Lys Arg Gly Arg Pro Arg Lys
                980                 985                 990

Val Val Pro Leu Glu Ala Asp Gly  Gly Thr Thr Gly Lys  Glu Gln Thr
            995                 1000                 1005

Ser Pro Gln Lys Lys Asp Val  Pro Val Val Arg Arg  Ser Thr Arg
        1010                 1015                 1020
```

-continued

```
Asn  Thr  Pro  Ala  Arg  Asn  Val  Ser  Thr  Leu  Xaa  Lys  Ser  Val  Leu
     1025                1030                1035

Val  Pro  Asn  Lys  Glu  Ala  Ala  Leu  Val  Val  Thr  Ser  Lys  Arg  Arg
     1040                1045                1050

Pro  Thr  Lys  Lys  Ser  Ala  Glu  Glu  Ser  Ser  Lys  Asp  Pro  Ser  Ala
     1055                1060                1065

Ala  Val  Ser  Asp  Trp  Ala  Gly  Gly  Ala  Ala  His  Thr  Glu  Ser  Ala
     1070                1075                1080

Asp  Arg  Arg  Asp  Gly  Leu  Leu  Ala  Ala  Ala  Ala  Leu  Thr  Pro  Ser
     1085                1090                1095

Ala  Gln  Gly  Thr  Arg  Thr  Arg  Ser  Arg  Arg  Thr  Met  Leu  Leu  Thr
     1100                1105                1110

Asp  Ile  Ser  Glu  Pro  Lys  Thr  Glu  Pro  Leu  Phe  Pro  Pro  Pro  Ser
     1115                1120                1125

Val  Lys  Val  Pro  Lys  Lys  Lys  Ser  Lys  Ala  Glu  Asn  Met  Glu  Ala
     1130                1135                1140

Ala  Ala  Gln  Leu  Lys  Glu  Leu  Val  Ser  Asp  Leu  Ser  Ser  Gln  Phe
     1145                1150                1155

Val  Val  Ser  Pro  Pro  Ala  Leu  Arg  Thr  Arg  Gln  Lys  Ser  Ile  Ser
     1160                1165                1170

Asn  Thr  Ser  Lys  Leu  Leu  Gly  Glu  Leu  Glu  Ser  Asp  Pro  Lys  Pro
     1175                1180                1185

Leu  Glu  Ile  Ile  Glu  Gln  Lys  Pro  Lys  Arg  Ser  Arg  Thr  Val  Lys
     1190                1195                1200

Thr  Arg  Ala  Ser  Arg  Asn  Thr  Gly  Lys  Gly  Ser  Ser  Trp  Ser  Pro
     1205                1210                1215

Pro  Pro  Val  Glu  Ile  Lys  Leu  Val  Ser  Pro  Leu  Ala  Ser  Pro  Val
     1220                1225                1230

Asp  Glu  Ile  Lys  Thr  Gly  Lys  Pro  Arg  Lys  Thr  Ala  Glu  Ile  Ala
     1235                1240                1245

Gly  Lys  Thr  Leu  Gly  Arg  Gly  Arg  Lys  Lys  Pro  Ser  Ser  Phe  Pro
     1250                1255                1260

Lys  Gln  Ile  Leu  Arg  Arg  Lys  Met  Leu
     1265                1270
```

<210> SEQ ID NO 9
<211> LENGTH: 24
<212> TYPE: DNA
<213> ORGANISM: Artificial
<220> FEATURE:
<223> OTHER INFORMATION: Description of Artificial Sequence:Artificially
      Synthesized Primer Sequence

<400> SEQUENCE: 9
cacccgtgaa gaaacaaata ggca                                            24

<210> SEQ ID NO 10
<211> LENGTH: 24
<212> TYPE: DNA
<213> ORGANISM: Artificial
<220> FEATURE:
<223> OTHER INFORMATION: Description of Artificial Sequence:Artificially
      Synthesized Primer Sequence

<400> SEQUENCE: 10
cctttggtac atgagcttct attt                                            24

<210> SEQ ID NO 11
<211> LENGTH: 7034

```
<212> TYPE: DNA
<213> ORGANISM: Mus musculus
<220> FEATURE:
<221> NAME/KEY: CDS
<222> LOCATION: (8)..(6736)

<400> SEQUENCE: 11 tggcagt atg caa gac ttg aca gct caa gtg act agt gat ctc ctg cat         49
        Met Gln Asp Leu Thr Ala Gln Val Thr Ser Asp Leu Leu His
        1               5                   10 ttc cca gaa gtg act att gaa gct ctt gga gaa gat gag ata aca tta         97
Phe Pro Glu Val Thr Ile Glu Ala Leu Gly Glu Asp Glu Ile Thr Leu
15                  20                  25                  30 gag tcc gtg ctt cgt gga aag ttt gct gca ggg aaa aat gga cta gca        145
Glu Ser Val Leu Arg Gly Lys Phe Ala Ala Gly Lys Asn Gly Leu Ala
                35                  40                  45 tgc tta gct tgt ggt cca caa ctt gaa gtt gta aac tcc tta aca gga        193
Cys Leu Ala Cys Gly Pro Gln Leu Glu Val Val Asn Ser Leu Thr Gly
    50                  55                  60 gag cgg tta tct gca tat aga ttc agt gga gta aat gaa cag cct cct        241
Glu Arg Leu Ser Ala Tyr Arg Phe Ser Gly Val Asn Glu Gln Pro Pro
65                  70                  75 gta gtc ctt gca gtg aaa gaa ttc tct tgg cat aag agg act gga ttg        289
Val Val Leu Ala Val Lys Glu Phe Ser Trp His Lys Arg Thr Gly Leu
80                  85                  90 tta ata gga ttg gaa gaa gca gat ggg agt gtt ctt tgt ctt tat gac        337
Leu Ile Gly Leu Glu Glu Ala Asp Gly Ser Val Leu Cys Leu Tyr Asp
95                  100                 105                 110 ctt ggt ata tca aga gtg gtc aaa gca gtt gtt ctt cct gga agg gta        385
Leu Gly Ile Ser Arg Val Val Lys Ala Val Val Leu Pro Gly Arg Val
                115                 120                 125 aca gct atc gag cct ata att aac cat gga gga gcc agt gcg agt acc        433
Thr Ala Ile Glu Pro Ile Ile Asn His Gly Gly Ala Ser Ala Ser Thr
    130                 135                 140 cag cat tta cat cca agt ctc cgg tgg ctt ttt ggc gtg gcc gct gtg        481
Gln His Leu His Pro Ser Leu Arg Trp Leu Phe Gly Val Ala Ala Val
145                 150                 155 gtg act gat gtt gga cag atc ctt ctt att gac ctg tgt ttg gat gac        529
Val Thr Asp Val Gly Gln Ile Leu Leu Ile Asp Leu Cys Leu Asp Asp
160                 165                 170 ttg tcc tgc agt cag aat gaa gtt gag gca tca gac ctt gaa gtt atc        577
Leu Ser Cys Ser Gln Asn Glu Val Glu Ala Ser Asp Leu Glu Val Ile
175                 180                 185                 190 act ggt atc cca gct gaa gta cca cac atc aga gag aga gtg atg aga        625
Thr Gly Ile Pro Ala Glu Val Pro His Ile Arg Glu Arg Val Met Arg
                195                 200                 205 gag ggg cgc cac ctg tgc ttc cag tta gta agc cca ttg gga gta gcc        673
Glu Gly Arg His Leu Cys Phe Gln Leu Val Ser Pro Leu Gly Val Ala
    210                 215                 220 att tct act ctg agt tac atc aac agg aca aat cag ctt gct gtg ggt        721
Ile Ser Thr Leu Ser Tyr Ile Asn Arg Thr Asn Gln Leu Ala Val Gly
225                 230                 235 ttt tct gat ggc tac tta gca ctt tgg aac atg aaa agc atg aaa aga        769
Phe Ser Asp Gly Tyr Leu Ala Leu Trp Asn Met Lys Ser Met Lys Arg
240                 245                 250 gaa tac tat aca cag ttg gaa ggt gga agg gtt cct gtc cat gca gtt        817
Glu Tyr Tyr Thr Gln Leu Glu Gly Gly Arg Val Pro Val His Ala Val
255                 260                 265                 270 gcc ttt caa gag cct gag aat gat cct cgt aac tgc tgt tat tta tgg        865
Ala Phe Gln Glu Pro Glu Asn Asp Pro Arg Asn Cys Cys Tyr Leu Trp
                275                 280                 285
```

-continued

| | |
|---|---|
| gct gtt cag tcc aca caa gat agt gaa ggg gat gtt ttg agt ttg cat<br>Ala Val Gln Ser Thr Gln Asp Ser Glu Gly Asp Val Leu Ser Leu His<br>290                            295                        300 | 913 |
| ctg ctt cag ctg gct ttt ggt gat aga aaa tgt ttg gca tca ggg caa<br>Leu Leu Gln Leu Ala Phe Gly Asp Arg Lys Cys Leu Ala Ser Gly Gln<br>305                            310                        315 | 961 |
| att tta tat gag gga tta gaa tac tgc gaa gaa aga tat aca ctg gat<br>Ile Leu Tyr Glu Gly Leu Glu Tyr Cys Glu Glu Arg Tyr Thr Leu Asp<br>320                            325                        330 | 1009 |
| cta gca ggt ggc acg ttc ccc tta agg gga caa act agt aat acc aaa<br>Leu Ala Gly Gly Thr Phe Pro Leu Arg Gly Gln Thr Ser Asn Thr Lys<br>335                            340                        345                        350 | 1057 |
| ttg ttg gga tgc cag agt ata gag aga ttt cca tct cat gga gac aga<br>Leu Leu Gly Cys Gln Ser Ile Glu Arg Phe Pro Ser His Gly Asp Arg<br>                        355                        360                        365 | 1105 |
| gaa gaa agt atg aga gaa gct ctg tct ccc gat acc agc gtt tct gtc<br>Glu Glu Ser Met Arg Glu Ala Leu Ser Pro Asp Thr Ser Val Ser Val<br>                      370                        375                        380 | 1153 |
| ttt acc tgg caa gtg aat ata tat gga cag gga aag cct tct gtg tat<br>Phe Thr Trp Gln Val Asn Ile Tyr Gly Gln Gly Lys Pro Ser Val Tyr<br>                      385                        390                        395 | 1201 |
| tta ggg cta ttt gac ata aat cgt tgg tat cat gca caa atg ccc gat<br>Leu Gly Leu Phe Asp Ile Asn Arg Trp Tyr His Ala Gln Met Pro Asp<br>400                            405                        410 | 1249 |
| tct tta aga tca gga gaa tct ctg cat aat tgc tct tat ttt gcg ttg<br>Ser Leu Arg Ser Gly Glu Ser Leu His Asn Cys Ser Tyr Phe Ala Leu<br>415                            420                        425                        430 | 1297 |
| tgg tca ttg gat tcg gtt gta agt agg act tct cca cat cac atc ttg<br>Trp Ser Leu Asp Ser Val Val Ser Arg Thr Ser Pro His His Ile Leu<br>                      435                        440                        445 | 1345 |
| gac ata cta gta cat gag agg agt tta aac cga ggg gtt cct cct tcc<br>Asp Ile Leu Val His Glu Arg Ser Leu Asn Arg Gly Val Pro Pro Ser<br>                        450                        455                        460 | 1393 |
| tac cca cct cca gag caa ttt ttt aac cca agt act ttt aat ttt gat<br>Tyr Pro Pro Pro Glu Gln Phe Phe Asn Pro Ser Thr Phe Asn Phe Asp<br>                      465                        470                        475 | 1441 |
| gcc act tgt ttg tta gac tct gga gtt atc cat gta act tgt gct gga<br>Ala Thr Cys Leu Leu Asp Ser Gly Val Ile His Val Thr Cys Ala Gly<br>480                            485                        490 | 1489 |
| ttt cag aag gag act ttg aca ttt tta aag aaa tca gga cca act ctt<br>Phe Gln Lys Glu Thr Leu Thr Phe Leu Lys Lys Ser Gly Pro Thr Leu<br>495                            500                        505                        510 | 1537 |
| aat gaa gtc att cct gat agt tat aat cga tgt ctt gtt gct ggt ctc<br>Asn Glu Val Ile Pro Asp Ser Tyr Asn Arg Cys Leu Val Ala Gly Leu<br>                      515                        520                        525 | 1585 |
| ctc tca cca aga ctt att gat att cag cct tcc agt tta agt caa gaa<br>Leu Ser Pro Arg Leu Ile Asp Ile Gln Pro Ser Ser Leu Ser Gln Glu<br>                      530                        535                        540 | 1633 |
| gaa caa tta gaa gct ata ttg tca gca gca att cag aca agt tcc ttg<br>Glu Gln Leu Glu Ala Ile Leu Ser Ala Ala Ile Gln Thr Ser Ser Leu<br>                        545                        550                        555 | 1681 |
| gga ctt ttg act ggt tac atc aga aca tgg ata ata gaa gaa caa cca<br>Gly Leu Leu Thr Gly Tyr Ile Arg Thr Trp Ile Ile Glu Glu Gln Pro<br>560                            565                        570 | 1729 |
| aat tct gct gct aat cta cga ttt gtt ctt gag tgg aca tgg aat aaa<br>Asn Ser Ala Ala Asn Leu Arg Phe Val Leu Glu Trp Thr Trp Asn Lys<br>575                            580                        585                        590 | 1777 |
| gtg gtt ctc aca aaa gaa gag ttt gat agg ctt tgt gtg ccg ctg ttt<br>Val Val Leu Thr Lys Glu Glu Phe Asp Arg Leu Cys Val Pro Leu Phe<br>                        595                        600                        605 | 1825 |

```
gac ggt tcg tgt cgt ttt att gac cca cag act att cag tct atc cag   1873
Asp Gly Ser Cys Arg Phe Ile Asp Pro Gln Thr Ile Gln Ser Ile Gln
            610                 615                 620 cag tgc cat tta ctg ctt agc aac ctt agt aca gtc tta agc tgt ttt   1921
Gln Cys His Leu Leu Leu Ser Asn Leu Ser Thr Val Leu Ser Cys Phe
625                 630                 635 gca atg gag gcc cag ggt atc act gag aga gga ctg gtg gac ttg agc   1969
Ala Met Glu Ala Gln Gly Ile Thr Glu Arg Gly Leu Val Asp Leu Ser
            640                 645                 650 aac aag cac atg gtc acc cag ctt ctc tgt cag tac gca cac atg gtt   2017
Asn Lys His Met Val Thr Gln Leu Leu Cys Gln Tyr Ala His Met Val
655                 660                 665                 670 ctg tgg ttc tgc cac tcg ggg ctt ctg ccc gaa ggc tta gat gat gct   2065
Leu Trp Phe Cys His Ser Gly Leu Leu Pro Glu Gly Leu Asp Asp Ala
            675                 680                 685 ctg cac ctg tca aga cta cgc tac aac tac cct gta att cag aac tac   2113
Leu His Leu Ser Arg Leu Arg Tyr Asn Tyr Pro Val Ile Gln Asn Tyr
                690                 695                 700 tat aca agt cgt cgg cag aag tct gag cgc tca ccc aga ggg aag tgg   2161
Tyr Thr Ser Arg Arg Gln Lys Ser Glu Arg Ser Pro Arg Gly Lys Trp
            705                 710                 715 aac cac gac tgc ttg atg att gat gga tta gtc tct caa cta gga gat   2209
Asn His Asp Cys Leu Met Ile Asp Gly Leu Val Ser Gln Leu Gly Asp
720                 725                 730 gaa gtt gag aag ttg tgg aag cgg gac gaa ggt ggc aca gga aga tac   2257
Glu Val Glu Lys Leu Trp Lys Arg Asp Glu Gly Gly Thr Gly Arg Tyr
735                 740                 745                 750 cct cct gct agc atc cac gca tta ctt gat ata tat tta tta gac aac   2305
Pro Pro Ala Ser Ile His Ala Leu Leu Asp Ile Tyr Leu Leu Asp Asn
            755                 760                 765 att acc gaa gca agc aaa cat gct att acc att tat ttg ctg ctt gat   2353
Ile Thr Glu Ala Ser Lys His Ala Ile Thr Ile Tyr Leu Leu Leu Asp
                770                 775                 780 att atg tat tcc ttt cca aat aaa acg gat acc ccc att gaa tct ttc   2401
Ile Met Tyr Ser Phe Pro Asn Lys Thr Asp Thr Pro Ile Glu Ser Phe
            785                 790                 795 ccc act gcc ttt gct att tct tgg ggc caa gtt aag cta gtt caa gga   2449
Pro Thr Ala Phe Ala Ile Ser Trp Gly Gln Val Lys Leu Val Gln Gly
800                 805                 810 ttt tgg cta cta gat cat aat gac tat gag aat ggt tta gac ctt ctg   2497
Phe Trp Leu Leu Asp His Asn Asp Tyr Glu Asn Gly Leu Asp Leu Leu
815                 820                 825                 830 ttt cac cca gtt act gca aag cct gca tcg tgg caa cat tca aag ata   2545
Phe His Pro Val Thr Ala Lys Pro Ala Ser Trp Gln His Ser Lys Ile
            835                 840                 845 att gaa gct ttt atg agt cag gga gag cac aaa cag gct ctc cgg tat   2593
Ile Glu Ala Phe Met Ser Gln Gly Glu His Lys Gln Ala Leu Arg Tyr
                850                 855                 860 ctt cag aca atg aag cca aca gtg tcc agt agc aat gaa gtt atc ctt   2641
Leu Gln Thr Met Lys Pro Thr Val Ser Ser Ser Asn Glu Val Ile Leu
            865                 870                 875 cac ctc act gtt cta ctt ttt aat aga tgc atg gtt gag gcc tgg aac   2689
His Leu Thr Val Leu Leu Phe Asn Arg Cys Met Val Glu Ala Trp Asn
880                 885                 890 tta ctg cga cag aat tca aac aga gta aat ata gag gaa tta tta aag   2737
Leu Leu Arg Gln Asn Ser Asn Arg Val Asn Ile Glu Glu Leu Leu Lys
895                 900                 905                 910 cac gct tat gaa gtt tgt cag gag atg ggc tta atg gag gat tta ctg   2785
His Ala Tyr Glu Val Cys Gln Glu Met Gly Leu Met Glu Asp Leu Leu
            915                 920                 925
```

```
aag ctg cca ttt aca aac act gag cag gaa tgc tta gtg aaa ttt tta       2833
Lys Leu Pro Phe Thr Asn Thr Glu Gln Glu Cys Leu Val Lys Phe Leu
        930                 935                 940 cag tcc agt acc agt gtt gag aat cat gaa ttc ctt cta gtt cac cat       2881
Gln Ser Ser Thr Ser Val Glu Asn His Glu Phe Leu Leu Val His His
            945                 950                 955 tta cag cgt gcc aat tat att tct gcc ttg aaa cta aac cag att ctg       2929
Leu Gln Arg Ala Asn Tyr Ile Ser Ala Leu Lys Leu Asn Gln Ile Leu
        960                 965                 970 aag aat aat ctc atg agt gat cgt gac cct cga ttg cgg gaa aga tcg       2977
Lys Asn Asn Leu Met Ser Asp Arg Asp Pro Arg Leu Arg Glu Arg Ser
975                 980                 985                 990 gtg act cga aat tct ata tta gac cag tat ggg aaa atc cta cct aga       3025
Val Thr Arg Asn Ser Ile Leu Asp Gln Tyr Gly Lys Ile Leu Pro Arg
            995                 1000                1005 gtc cag aga aag tta gct gtt gag cga gct aag cct tac cac ctg           3070
Val Gln Arg Lys Leu Ala Val Glu Arg Ala Lys Pro Tyr His Leu
                1010                1015                1020 tcg aca tcc tca gtt ttt cat gaa gtt tct aga ccc aaa ccg tta           3115
Ser Thr Ser Ser Val Phe His Glu Val Ser Arg Pro Lys Pro Leu
                1025                1030                1035 tcg gca ttt cca aag aaa gct ata act gga aca gtg tta acc cga           3160
Ser Ala Phe Pro Lys Lys Ala Ile Thr Gly Thr Val Leu Thr Arg
                1040                1045                1050 tct acg ttc atc agc aat gtt tta tct aaa att gga gag gtg tgg           3205
Ser Thr Phe Ile Ser Asn Val Leu Ser Lys Ile Gly Glu Val Trp
                1055                1060                1065 gca agt cat gag cct aga aat ggc gtc tca ctt ttt aac agt cct           3250
Ala Ser His Glu Pro Arg Asn Gly Val Ser Leu Phe Asn Ser Pro
                1070                1075                1080 aaa aca gaa cag cca tct cct gta gta cac tct ttc cca cac cca           3295
Lys Thr Glu Gln Pro Ser Pro Val Val His Ser Phe Pro His Pro
                1085                1090                1095 gag ctt cct gag gcg ttt gtt gga act cca att tca aat aca tcc           3340
Glu Leu Pro Glu Ala Phe Val Gly Thr Pro Ile Ser Asn Thr Ser
                1100                1105                1110 cag aga att tct aga tta ctg gat ttg gtt gtc cat cct gta ccc           3385
Gln Arg Ile Ser Arg Leu Leu Asp Leu Val Val His Pro Val Pro
                1115                1120                1125 cag cct tct cag tgt ttg gag ttt att caa caa agt ccc aca aga           3430
Gln Pro Ser Gln Cys Leu Glu Phe Ile Gln Gln Ser Pro Thr Arg
                1130                1135                1140 tct cct ttg tgt ctg ctg tcc agt tcg tta cca tta agt tca cag           3475
Ser Pro Leu Cys Leu Leu Ser Ser Ser Leu Pro Leu Ser Ser Gln
                1145                1150                1155 ttt aaa agg cca cat cag aat acc tcc agg cct tca gag ttg ctt           3520
Phe Lys Arg Pro His Gln Asn Thr Ser Arg Pro Ser Glu Leu Leu
                1160                1165                1170 tta ctt gag act cct ctc ata gtt aag aaa gct aaa tct ttg gct           3565
Leu Leu Glu Thr Pro Leu Ile Val Lys Lys Ala Lys Ser Leu Ala
                1175                1180                1185 ctg tca gcc acg tct tct gga ttt gcc gag ttt act cct cca tcc           3610
Leu Ser Ala Thr Ser Ser Gly Phe Ala Glu Phe Thr Pro Pro Ser
                1190                1195                1200 atc ctt agg tct ggt ttt cga aca aca cct tta gca tct ccc tct           3655
Ile Leu Arg Ser Gly Phe Arg Thr Thr Pro Leu Ala Ser Pro Ser
                1205                1210                1215 ttg tca cct gga aga tct ctc act ccg cct ttc aga gtt aaa gaa           3700
Leu Ser Pro Gly Arg Ser Leu Thr Pro Pro Phe Arg Val Lys Glu
                1220                1225                1230
```

```
aca agg att tca ttc atg gaa gaa ggc atg aat aca cac tgg act       3745
Thr Arg Ile Ser Phe Met Glu Glu Gly Met Asn Thr His Trp Thr
        1235             1240                 1245 gat aga gct aca gat gac cga aat aca aaa gcg ttt gtt agc aca       3790
Asp Arg Ala Thr Asp Asp Arg Asn Thr Lys Ala Phe Val Ser Thr
        1250             1255                 1260 tct ttc cat aaa tgt gga ctt cca gca gaa act gag tgg atg aag       3835
Ser Phe His Lys Cys Gly Leu Pro Ala Glu Thr Glu Trp Met Lys
        1265             1270                 1275 acc agt gat aag aat aca tat ttt cct ctg gat gtc cct gca aag       3880
Thr Ser Asp Lys Asn Thr Tyr Phe Pro Leu Asp Val Pro Ala Lys
        1280             1285                 1290 ggc cct cag aaa gtg gtg gca gag tca ctg gct acc cat tca gga       3925
Gly Pro Gln Lys Val Val Ala Glu Ser Leu Ala Thr His Ser Gly
        1295             1300                 1305 agg ctg gag aaa ctg gat gtg agc aaa gaa gac agc aca gct tcc       3970
Arg Leu Glu Lys Leu Asp Val Ser Lys Glu Asp Ser Thr Ala Ser
        1310             1315                 1320 acc agg tca gac cag acc tcc tta gag tat cat gac gca cca tca       4015
Thr Arg Ser Asp Gln Thr Ser Leu Glu Tyr His Asp Ala Pro Ser
        1325             1330                 1335 cca gaa gac ttg gaa ggt gct gtt ttt gtg tct ccc aag cca gca       4060
Pro Glu Asp Leu Glu Gly Ala Val Phe Val Ser Pro Lys Pro Ala
        1340             1345                 1350 tct tcc tcc act gaa cta act act aat tca act cta caa aca gag       4105
Ser Ser Ser Thr Glu Leu Thr Thr Asn Ser Thr Leu Gln Thr Glu
        1355             1360                 1365 agg gat aat gat aaa gat gcg ttt aag tca gaa ggt act cct tca       4150
Arg Asp Asn Asp Lys Asp Ala Phe Lys Ser Glu Gly Thr Pro Ser
        1370             1375                 1380 ccc gtg aag aaa caa ata ggc acg gga gac gct gca gtg gaa gca       4195
Pro Val Lys Lys Gln Ile Gly Thr Gly Asp Ala Ala Val Glu Ala
        1385             1390                 1395 ttt tca gaa ctg agt cgc tta gac cct gtt gaa aga gct gaa gct       4240
Phe Ser Glu Leu Ser Arg Leu Asp Pro Val Glu Arg Ala Glu Ala
        1400             1405                 1410 tct ttt ggt gtg tcg tca gtc tgt gaa ggg gaa acc tcc act tca       4285
Ser Phe Gly Val Ser Ser Val Cys Glu Gly Glu Thr Ser Thr Ser
        1415             1420                 1425 aac tcc aag acg tca gtt ctg gat gga atc gtg cct att gag agc       4330
Asn Ser Lys Thr Ser Val Leu Asp Gly Ile Val Pro Ile Glu Ser
        1430             1435                 1440 cga acc tcc ata ctt aca gca gac cac aaa gag tct gtg gcc aac       4375
Arg Thr Ser Ile Leu Thr Ala Asp His Lys Glu Ser Val Ala Asn
        1445             1450                 1455 acg gtt gca gat gtt gaa agc tct ggg tcc acc agc tcc aag tgc       4420
Thr Val Ala Asp Val Glu Ser Ser Gly Ser Thr Ser Ser Lys Cys
        1460             1465                 1470 ccg gtt acc tct gaa cgc agc ctc ggc caa aaa cta aca tta aac       4465
Pro Val Thr Ser Glu Arg Ser Leu Gly Gln Lys Leu Thr Leu Asn
        1475             1480                 1485 tta aaa gaa gat gaa ata gaa gct cat gta cca aag gag aac gtt       4510
Leu Lys Glu Asp Glu Ile Glu Ala His Val Pro Lys Glu Asn Val
        1490             1495                 1500 ggt tta cca gaa gaa agc cct cga att tct gct gct cct tct gat       4555
Gly Leu Pro Glu Glu Ser Pro Arg Ile Ser Ala Ala Pro Ser Asp
        1505             1510                 1515 act cac gag att cat cta att gga tgt gaa aat ctt gaa gtt caa       4600
Thr His Glu Ile His Leu Ile Gly Cys Glu Asn Leu Glu Val Gln
        1520             1525                 1530
```

```
aat tca gaa gag gag gcc aag aat ctt tca ttt gat gag ttg tat    4645
Asn Ser Glu Glu Glu Ala Lys Asn Leu Ser Phe Asp Glu Leu Tyr
        1535                1540                1545 ccc tta ggg gca gag aaa ctt gag tat aat ctc agt act att gag    4690
Pro Leu Gly Ala Glu Lys Leu Glu Tyr Asn Leu Ser Thr Ile Glu
        1550                1555                1560 cag cag ttt tgt gac ttg cct gat gac aaa gac tct gct gaa tgt    4735
Gln Gln Phe Cys Asp Leu Pro Asp Asp Lys Asp Ser Ala Glu Cys
        1565                1570                1575 gat gct gct gaa gta gac ggg gaa ctt ttt gtg gcc cag agc aac    4780
Asp Ala Ala Glu Val Asp Gly Glu Leu Phe Val Ala Gln Ser Asn
        1580                1585                1590 ttt acc ctg att tta gaa ggt gaa gaa gga gaa gct gag gca agc    4825
Phe Thr Leu Ile Leu Glu Gly Glu Glu Gly Glu Ala Glu Ala Ser
        1595                1600                1605 gac tct gca gca cct aat atg tta ccg aaa tcg acc aag gaa aaa    4870
Asp Ser Ala Ala Pro Asn Met Leu Pro Lys Ser Thr Lys Glu Lys
        1610                1615                1620 cct gtg tgc tac agg gaa ccc cat aat cag gag cgc gtt aca gat    4915
Pro Val Cys Tyr Arg Glu Pro His Asn Gln Glu Arg Val Thr Asp
        1625                1630                1635 ttg cca tct gct gtg act gct gac caa gaa tcc cac aag gta gag    4960
Leu Pro Ser Ala Val Thr Ala Asp Gln Glu Ser His Lys Val Glu
        1640                1645                1650 act tta ccg tat gtg cct gaa ccg gtt aaa gtg gca att gca gaa    5005
Thr Leu Pro Tyr Val Pro Glu Pro Val Lys Val Ala Ile Ala Glu
        1655                1660                1665 aat ctg ttg gat gta att aaa gac acc aga agt aag gaa gca act    5050
Asn Leu Leu Asp Val Ile Lys Asp Thr Arg Ser Lys Glu Ala Thr
        1670                1675                1680 ccc gtg gca gca ggt gag gct ggt gat gag gac gga gca gtg ata    5095
Pro Val Ala Ala Gly Glu Ala Gly Asp Glu Asp Gly Ala Val Ile
        1685                1690                1695 gtc tca aag gct gca cat tcg tcc agg ctg aca aac tct aca ccg    5140
Val Ser Lys Ala Ala His Ser Ser Arg Leu Thr Asn Ser Thr Pro
        1700                1705                1710 aag act gtt aag gaa cca cgt gca gag act gta aat acc agc cag    5185
Lys Thr Val Lys Glu Pro Arg Ala Glu Thr Val Asn Thr Ser Gln
        1715                1720                1725 agt gat gac atg gtt tct tct aga act ctc aca aga agg cag cat    5230
Ser Asp Asp Met Val Ser Ser Arg Thr Leu Thr Arg Arg Gln His
        1730                1735                1740 gcc cta agc ctg aat gtc aca tca gaa caa gag cct tca gca gtt    5275
Ala Leu Ser Leu Asn Val Thr Ser Glu Gln Glu Pro Ser Ala Val
        1745                1750                1755 gcc act cct aag aag aga act aga aaa att aaa gaa act cct gag    5320
Ala Thr Pro Lys Lys Arg Thr Arg Lys Ile Lys Glu Thr Pro Glu
        1760                1765                1770 tct tct gaa agg acc tgt tct gac cta aaa gta gca cct gag aac    5365
Ser Ser Glu Arg Thr Cys Ser Asp Leu Lys Val Ala Pro Glu Asn
        1775                1780                1785 caa ctg aca gct cag aat cct ccc gct cct agg aga aga aag aag    5410
Gln Leu Thr Ala Gln Asn Pro Pro Ala Pro Arg Arg Arg Lys Lys
        1790                1795                1800 aag gac gtt agc caa ggc aca ctg cca agt tct ggt gct gtg gag    5455
Lys Asp Val Ser Gln Gly Thr Leu Pro Ser Ser Gly Ala Val Glu
        1805                1810                1815 ccg gag ccg gaa cct cag ggt acg ccg gga aga ctg agg ctg aga    5500
Pro Glu Pro Glu Pro Gln Gly Thr Pro Gly Arg Leu Arg Leu Arg
        1820                1825                1830
```

```
acg cag cca ccc gag cca gca gct gaa gaa act cct tct aga aca      5545
Thr Gln Pro Pro Glu Pro Ala Ala Glu Glu Thr Pro Ser Arg Thr
        1835            1840            1845 aaa gtc agg ctt tca tct gtt aga aag gga acc cct aga aga ctt      5590
Lys Val Arg Leu Ser Ser Val Arg Lys Gly Thr Pro Arg Arg Leu
1850            1855            1860 aag aag tct gta gaa aat ggg caa agt ata gaa att cta gat gat      5635
Lys Lys Ser Val Glu Asn Gly Gln Ser Ile Glu Ile Leu Asp Asp
        1865            1870            1875 ctc aaa ggg agt gag gca gca agt cat gac ggg act gtc aca gag      5680
Leu Lys Gly Ser Glu Ala Ala Ser His Asp Gly Thr Val Thr Glu
1880            1885            1890 ctg agg aat gcc aat tta gaa gat act cag aat atg gag tat aaa      5725
Leu Arg Asn Ala Asn Leu Glu Asp Thr Gln Asn Met Glu Tyr Lys
        1895            1900            1905 caa gat gaa cac agt gac cag caa ccg cct cta aaa cga aag agg      5770
Gln Asp Glu His Ser Asp Gln Gln Pro Pro Leu Lys Arg Lys Arg
1910            1915            1920 gtc aga gag aga gaa gtt agt gtg tca agt gtg aca gaa gag cca      5815
Val Arg Glu Arg Glu Val Ser Val Ser Ser Val Thr Glu Glu Pro
        1925            1930            1935 aag ctt gac tca tcc cag ttg cct ctt cag aca gga ctc gat gta      5860
Lys Leu Asp Ser Ser Gln Leu Pro Leu Gln Thr Gly Leu Asp Val
1940            1945            1950 cct gcc acc cct agg aaa cgt ggt aga ccc agg aag gta gtt ccc      5905
Pro Ala Thr Pro Arg Lys Arg Gly Arg Pro Arg Lys Val Val Pro
        1955            1960            1965 tta gaa gct gac ggt ggc aca act ggt aag gaa cag aca agt cct      5950
Leu Glu Ala Asp Gly Gly Thr Thr Gly Lys Glu Gln Thr Ser Pro
1970            1975            1980 cag aag aaa gat gtt ccg gtt gtc cgg aga tct aca cgg aac acc      5995
Gln Lys Lys Asp Val Pro Val Val Arg Arg Ser Thr Arg Asn Thr
        1985            1990            1995 cca gct aga aat gtg agt act tta aaa aaa tca gtt tta gtg cca      6040
Pro Ala Arg Asn Val Ser Thr Leu Lys Lys Ser Val Leu Val Pro
2000            2005            2010 aat aag gaa gct gct cta gtg gtg aca tct aag agg aga cct aca      6085
Asn Lys Glu Ala Ala Leu Val Val Thr Ser Lys Arg Arg Pro Thr
        2015            2020            2025 aag aag tct gca gag gaa agc tca aaa gat cca tca gcg gca gtc      6130
Lys Lys Ser Ala Glu Glu Ser Ser Lys Asp Pro Ser Ala Ala Val
2030            2035            2040 tca gac tgg gcg ggt gga gca gcc cac aca gag tcc gct gac cga      6175
Ser Asp Trp Ala Gly Gly Ala Ala His Thr Glu Ser Ala Asp Arg
        2045            2050            2055 agg gac gga ctg ctt gcc gcc gct gct ctc acg cca tct gcc cag      6220
Arg Asp Gly Leu Leu Ala Ala Ala Ala Leu Thr Pro Ser Ala Gln
2060            2065            2070 ggc aca agg act agg tct aga agg acc atg ttg ttg acg gac att      6265
Gly Thr Arg Thr Arg Ser Arg Arg Thr Met Leu Leu Thr Asp Ile
        2075            2080            2085 tct gaa ccc aaa act gag cct tta ttt cct cct cct tca gtg aag      6310
Ser Glu Pro Lys Thr Glu Pro Leu Phe Pro Pro Pro Ser Val Lys
2090            2095            2100 gtt cca aag aaa aaa tca aaa gct gag aac atg gag gcc gca gcc      6355
Val Pro Lys Lys Lys Ser Lys Ala Glu Asn Met Glu Ala Ala Ala
        2105            2110            2115 cag ctg aaa gaa ttg gtg tca gat tta tct tct cag ttt gtt gtt      6400
Gln Leu Lys Glu Leu Val Ser Asp Leu Ser Ser Gln Phe Val Val
2120            2125            2130
```

```
tcc cct cct gcc ttg aga acc agg cag aaa agt ata tcc aat act       6445
Ser Pro Pro Ala Leu Arg Thr Arg Gln Lys Ser Ile Ser Asn Thr
            2135                2140                2145 tcc aag ctt cta ggt gaa ctg gag agt gac cct aaa cca tta gag       6490
Ser Lys Leu Leu Gly Glu Leu Glu Ser Asp Pro Lys Pro Leu Glu
            2150                2155                2160 atc ata gaa caa aaa cca aaa aga agc agg act gtg aag aca aga       6535
Ile Ile Glu Gln Lys Pro Lys Arg Ser Arg Thr Val Lys Thr Arg
            2165                2170                2175 gca agc aga aac aca gga aaa gga agt tct tgg tca cct cct cct       6580
Ala Ser Arg Asn Thr Gly Lys Gly Ser Ser Trp Ser Pro Pro Pro
            2180                2185                2190 gta gaa att aag ctg gtt tct ccc ttg gcg agt cca gtg gat gaa       6625
Val Glu Ile Lys Leu Val Ser Pro Leu Ala Ser Pro Val Asp Glu
            2195                2200                2205 ata aag acc ggc aag cca aga aaa act gca gaa ata gca gga aaa       6670
Ile Lys Thr Gly Lys Pro Arg Lys Thr Ala Glu Ile Ala Gly Lys
            2210                2215                2220 act ctt gga agg ggc aga aag aag cca tct tct ttt cca aag caa       6715
Thr Leu Gly Arg Gly Arg Lys Lys Pro Ser Ser Phe Pro Lys Gln
            2225                2230                2235 att tta cgc agg aaa atg ctg taattttag cccaagattt taacacgcac       6766
Ile Leu Arg Arg Lys Met Leu
            2240 ctgtttgtaa aagtcaacag tatttgtgtg gattattaaa gtcaccaatt tggatgaaaa  6826 tactttatat aaattgtaca attttgtaag cagtaaatga gtaactccac atggagtgca  6886 gttcttgtag tgcaggcgtt ttatacgact tgatgcgttt atatcaatgt aaatatgact  6946 tatcattggg aggttaaata aactactgta aagtaaaaaa aaaaaaaaaa aaaaaaaaaa  7006 aaaaaaaaaa aaaaaaaaaa aaaaaaaa                                     7034

<210> SEQ ID NO 12
<211> LENGTH: 2243
<212> TYPE: PRT
<213> ORGANISM: Mus musculus

<400> SEQUENCE: 12

Met Gln Asp Leu Thr Ala Gln Val Thr Ser Asp Leu Leu His Phe Pro
1               5                   10                  15

Glu Val Thr Ile Glu Ala Leu Gly Glu Asp Ile Thr Leu Glu Ser
            20                  25                  30

Val Leu Arg Gly Lys Phe Ala Ala Gly Lys Asn Gly Leu Ala Cys Leu
        35                  40                  45

Ala Cys Gly Pro Gln Leu Glu Val Val Asn Ser Leu Thr Gly Glu Arg
    50                  55                  60

Leu Ser Ala Tyr Arg Phe Ser Gly Val Asn Glu Gln Pro Pro Val Val
65                  70                  75                  80

Leu Ala Val Lys Glu Phe Ser Trp His Lys Arg Thr Gly Leu Leu Ile
                85                  90                  95

Gly Leu Glu Glu Ala Asp Gly Ser Val Leu Cys Leu Tyr Asp Leu Gly
            100                 105                 110

Ile Ser Arg Val Val Lys Ala Val Val Leu Pro Gly Arg Val Thr Ala
        115                 120                 125

Ile Glu Pro Ile Ile Asn His Gly Gly Ala Ser Ala Ser Thr Gln His
    130                 135                 140

Leu His Pro Ser Leu Arg Trp Leu Phe Gly Val Ala Ala Val Val Thr
145                 150                 155                 160
```

-continued

```
Asp Val Gly Gln Ile Leu Leu Ile Asp Leu Cys Leu Asp Leu Ser
            165                 170                 175

Cys Ser Gln Asn Glu Val Glu Ala Ser Asp Leu Glu Val Ile Thr Gly
            180                 185                 190

Ile Pro Ala Glu Val Pro His Ile Arg Glu Arg Val Met Arg Glu Gly
        195                 200                 205

Arg His Leu Cys Phe Gln Leu Val Ser Pro Leu Gly Val Ala Ile Ser
    210                 215                 220

Thr Leu Ser Tyr Ile Asn Arg Thr Asn Gln Leu Ala Val Gly Phe Ser
225                 230                 235                 240

Asp Gly Tyr Leu Ala Leu Trp Asn Met Lys Ser Met Lys Arg Glu Tyr
                245                 250                 255

Tyr Thr Gln Leu Glu Gly Gly Arg Val Pro Val His Ala Val Ala Phe
            260                 265                 270

Gln Glu Pro Glu Asn Asp Pro Arg Asn Cys Cys Tyr Leu Trp Ala Val
        275                 280                 285

Gln Ser Thr Gln Asp Ser Glu Gly Asp Val Leu Ser Leu His Leu Leu
    290                 295                 300

Gln Leu Ala Phe Gly Asp Arg Lys Cys Leu Ala Ser Gly Gln Ile Leu
305                 310                 315                 320

Tyr Glu Gly Leu Glu Tyr Cys Glu Glu Arg Tyr Thr Leu Asp Leu Ala
                325                 330                 335

Gly Gly Thr Phe Pro Leu Arg Gly Gln Thr Ser Asn Thr Lys Leu Leu
            340                 345                 350

Gly Cys Gln Ser Ile Glu Arg Phe Pro Ser His Gly Asp Arg Glu Glu
        355                 360                 365

Ser Met Arg Glu Ala Leu Ser Pro Asp Thr Ser Val Ser Val Phe Thr
    370                 375                 380

Trp Gln Val Asn Ile Tyr Gly Gln Gly Lys Pro Ser Val Tyr Leu Gly
385                 390                 395                 400

Leu Phe Asp Ile Asn Arg Trp Tyr His Ala Gln Met Pro Asp Ser Leu
                405                 410                 415

Arg Ser Gly Glu Ser Leu His Asn Cys Ser Tyr Phe Ala Leu Trp Ser
            420                 425                 430

Leu Asp Ser Val Val Ser Arg Thr Ser Pro His His Ile Leu Asp Ile
        435                 440                 445

Leu Val His Glu Arg Ser Leu Asn Arg Gly Val Pro Pro Ser Tyr Pro
    450                 455                 460

Pro Pro Glu Gln Phe Phe Asn Pro Ser Thr Phe Asn Phe Asp Ala Thr
465                 470                 475                 480

Cys Leu Leu Asp Ser Gly Val Ile His Val Thr Cys Ala Gly Phe Gln
                485                 490                 495

Lys Glu Thr Leu Thr Phe Leu Lys Lys Ser Gly Pro Thr Leu Asn Glu
            500                 505                 510

Val Ile Pro Asp Ser Tyr Asn Arg Cys Leu Val Ala Gly Leu Leu Ser
        515                 520                 525

Pro Arg Leu Ile Asp Ile Gln Pro Ser Ser Leu Ser Gln Glu Glu Gln
    530                 535                 540

Leu Glu Ala Ile Leu Ser Ala Ala Ile Gln Thr Ser Ser Leu Gly Leu
545                 550                 555                 560

Leu Thr Gly Tyr Ile Arg Thr Trp Ile Glu Glu Gln Pro Asn Ser
                565                 570                 575

Ala Ala Asn Leu Arg Phe Val Leu Glu Trp Thr Trp Asn Lys Val Val
            580                 585                 590
```

```
Leu Thr Lys Glu Glu Phe Asp Arg Leu Cys Val Pro Leu Phe Asp Gly
            595                 600                 605

Ser Cys Arg Phe Ile Asp Pro Gln Thr Ile Gln Ser Ile Gln Gln Cys
610                 615                 620

His Leu Leu Leu Ser Asn Leu Ser Thr Val Leu Ser Cys Phe Ala Met
625                 630                 635                 640

Glu Ala Gln Gly Ile Thr Glu Arg Gly Leu Val Asp Leu Ser Asn Lys
                645                 650                 655

His Met Val Thr Gln Leu Leu Cys Gln Tyr Ala His Met Val Leu Trp
            660                 665                 670

Phe Cys His Ser Gly Leu Leu Pro Glu Gly Leu Asp Asp Ala Leu His
            675                 680                 685

Leu Ser Arg Leu Arg Tyr Asn Tyr Pro Val Ile Gln Asn Tyr Tyr Thr
            690                 695                 700

Ser Arg Arg Gln Lys Ser Glu Arg Ser Pro Arg Gly Lys Trp Asn His
705                 710                 715                 720

Asp Cys Leu Met Ile Asp Gly Leu Val Ser Gln Leu Gly Asp Glu Val
                725                 730                 735

Glu Lys Leu Trp Lys Arg Asp Glu Gly Gly Thr Gly Arg Tyr Pro Pro
            740                 745                 750

Ala Ser Ile His Ala Leu Leu Asp Ile Tyr Leu Leu Asp Asn Ile Thr
            755                 760                 765

Glu Ala Ser Lys His Ala Ile Thr Ile Tyr Leu Leu Leu Asp Ile Met
770                 775                 780

Tyr Ser Phe Pro Asn Lys Thr Asp Thr Pro Ile Glu Ser Phe Pro Thr
785                 790                 795                 800

Ala Phe Ala Ile Ser Trp Gly Gln Val Lys Leu Val Gln Gly Phe Trp
                805                 810                 815

Leu Leu Asp His Asn Asp Tyr Glu Asn Gly Leu Asp Leu Leu Phe His
            820                 825                 830

Pro Val Thr Ala Lys Pro Ala Ser Trp Gln His Ser Lys Ile Ile Glu
            835                 840                 845

Ala Phe Met Ser Gln Gly Glu His Lys Gln Ala Leu Arg Tyr Leu Gln
850                 855                 860

Thr Met Lys Pro Thr Val Ser Ser Asn Glu Val Ile Leu His Leu
865                 870                 875                 880

Thr Val Leu Leu Phe Asn Arg Cys Met Val Glu Ala Trp Asn Leu Leu
                885                 890                 895

Arg Gln Asn Ser Asn Arg Val Asn Ile Glu Glu Leu Leu Lys His Ala
            900                 905                 910

Tyr Glu Val Cys Gln Glu Met Gly Leu Met Glu Asp Leu Leu Lys Leu
            915                 920                 925

Pro Phe Thr Asn Thr Glu Gln Glu Cys Leu Val Lys Phe Leu Gln Ser
            930                 935                 940

Ser Thr Ser Val Glu Asn His Glu Phe Leu Leu Val His His Leu Gln
945                 950                 955                 960

Arg Ala Asn Tyr Ile Ser Ala Leu Lys Leu Asn Gln Ile Leu Lys Asn
                965                 970                 975

Asn Leu Met Ser Asp Arg Asp Pro Arg Leu Arg Glu Arg Ser Val Thr
            980                 985                 990

Arg Asn Ser Ile Leu Asp Gln Tyr  Gly Lys Ile Leu Pro  Arg Val Gln
            995                 1000                1005

Arg Lys  Leu Ala Val Glu Arg  Ala Lys Pro Tyr His  Leu Ser Thr
```

```
                1010                1015                1020

Ser Ser Val Phe His Glu Val Ser Arg Pro Lys Pro Leu Ser Ala
    1025                1030                1035

Phe Pro Lys Lys Ala Ile Thr Gly Thr Val Leu Thr Arg Ser Thr
    1040                1045                1050

Phe Ile Ser Asn Val Leu Ser Lys Ile Gly Glu Val Trp Ala Ser
    1055                1060                1065

His Glu Pro Arg Asn Gly Val Ser Leu Phe Asn Ser Pro Lys Thr
    1070                1075                1080

Glu Gln Pro Ser Pro Val Val His Ser Phe Pro His Pro Glu Leu
    1085                1090                1095

Pro Glu Ala Phe Val Gly Thr Pro Ile Ser Asn Thr Ser Gln Arg
    1100                1105                1110

Ile Ser Arg Leu Leu Asp Leu Val Val His Pro Val Pro Gln Pro
    1115                1120                1125

Ser Gln Cys Leu Glu Phe Ile Gln Gln Ser Pro Thr Arg Ser Pro
    1130                1135                1140

Leu Cys Leu Leu Ser Ser Ser Leu Pro Leu Ser Ser Gln Phe Lys
    1145                1150                1155

Arg Pro His Gln Asn Thr Ser Arg Pro Ser Glu Leu Leu Leu Leu
    1160                1165                1170

Glu Thr Pro Leu Ile Val Lys Lys Ala Lys Ser Leu Ala Leu Ser
    1175                1180                1185

Ala Thr Ser Ser Gly Phe Ala Glu Phe Thr Pro Pro Ser Ile Leu
    1190                1195                1200

Arg Ser Gly Phe Arg Thr Thr Pro Leu Ala Ser Pro Ser Leu Ser
    1205                1210                1215

Pro Gly Arg Ser Leu Thr Pro Pro Phe Arg Val Lys Glu Thr Arg
    1220                1225                1230

Ile Ser Phe Met Glu Glu Gly Met Asn Thr His Trp Thr Asp Arg
    1235                1240                1245

Ala Thr Asp Asp Arg Asn Thr Lys Ala Phe Val Ser Thr Ser Phe
    1250                1255                1260

His Lys Cys Gly Leu Pro Ala Glu Thr Glu Trp Met Lys Thr Ser
    1265                1270                1275

Asp Lys Asn Thr Tyr Phe Pro Leu Asp Val Pro Ala Lys Gly Pro
    1280                1285                1290

Gln Lys Val Val Ala Glu Ser Leu Ala Thr His Ser Gly Arg Leu
    1295                1300                1305

Glu Lys Leu Asp Val Ser Lys Glu Asp Ser Thr Ala Ser Thr Arg
    1310                1315                1320

Ser Asp Gln Thr Ser Leu Glu Tyr His Asp Ala Pro Ser Pro Glu
    1325                1330                1335

Asp Leu Glu Gly Ala Val Phe Val Ser Pro Lys Pro Ala Ser Ser
    1340                1345                1350

Ser Thr Glu Leu Thr Thr Asn Ser Thr Leu Gln Thr Glu Arg Asp
    1355                1360                1365

Asn Asp Lys Asp Ala Phe Lys Ser Glu Gly Thr Pro Ser Pro Val
    1370                1375                1380

Lys Lys Gln Ile Gly Thr Gly Asp Ala Ala Val Glu Ala Phe Ser
    1385                1390                1395

Glu Leu Ser Arg Leu Asp Pro Val Glu Arg Ala Glu Ala Ser Phe
    1400                1405                1410
```

-continued

Gly Val Ser Ser Val Cys Glu Gly Glu Thr Ser Thr Ser Asn Ser
1415                1420                1425

Lys Thr Ser Val Leu Asp Gly Ile Val Pro Ile Glu Ser Arg Thr
1430                1435                1440

Ser Ile Leu Thr Ala Asp His Lys Glu Ser Val Ala Asn Thr Val
1445                1450                1455

Ala Asp Val Glu Ser Ser Gly Ser Thr Ser Ser Lys Cys Pro Val
1460                1465                1470

Thr Ser Glu Arg Ser Leu Gly Gln Lys Leu Thr Leu Asn Leu Lys
1475                1480                1485

Glu Asp Glu Ile Glu Ala His Val Pro Lys Glu Asn Val Gly Leu
1490                1495                1500

Pro Glu Glu Ser Pro Arg Ile Ser Ala Ala Pro Ser Asp Thr His
1505                1510                1515

Glu Ile His Leu Ile Gly Cys Glu Asn Leu Glu Val Gln Asn Ser
1520                1525                1530

Glu Glu Glu Ala Lys Asn Leu Ser Phe Asp Glu Leu Tyr Pro Leu
1535                1540                1545

Gly Ala Glu Lys Leu Glu Tyr Asn Leu Ser Thr Ile Glu Gln Gln
1550                1555                1560

Phe Cys Asp Leu Pro Asp Asp Lys Asp Ser Ala Glu Cys Asp Ala
1565                1570                1575

Ala Glu Val Asp Gly Glu Leu Phe Val Ala Gln Ser Asn Phe Thr
1580                1585                1590

Leu Ile Leu Glu Gly Glu Gly Glu Ala Glu Ala Ser Asp Ser
1595                1600                1605

Ala Ala Pro Asn Met Leu Pro Lys Ser Thr Lys Glu Lys Pro Val
1610                1615                1620

Cys Tyr Arg Glu Pro His Asn Gln Glu Arg Val Thr Asp Leu Pro
1625                1630                1635

Ser Ala Val Thr Ala Asp Gln Glu Ser His Lys Val Glu Thr Leu
1640                1645                1650

Pro Tyr Val Pro Glu Pro Val Lys Val Ala Ile Ala Glu Asn Leu
1655                1660                1665

Leu Asp Val Ile Lys Asp Thr Arg Ser Lys Glu Ala Thr Pro Val
1670                1675                1680

Ala Ala Gly Glu Ala Gly Asp Glu Asp Gly Ala Val Ile Val Ser
1685                1690                1695

Lys Ala Ala His Ser Ser Arg Leu Thr Asn Ser Thr Pro Lys Thr
1700                1705                1710

Val Lys Glu Pro Arg Ala Glu Thr Val Asn Thr Ser Gln Ser Asp
1715                1720                1725

Asp Met Val Ser Ser Arg Thr Leu Thr Arg Arg Gln His Ala Leu
1730                1735                1740

Ser Leu Asn Val Thr Ser Glu Gln Glu Pro Ser Ala Val Ala Thr
1745                1750                1755

Pro Lys Lys Arg Thr Arg Lys Ile Lys Glu Thr Pro Glu Ser Ser
1760                1765                1770

Glu Arg Thr Cys Ser Asp Leu Lys Val Ala Pro Glu Asn Gln Leu
1775                1780                1785

Thr Ala Gln Asn Pro Pro Ala Pro Arg Arg Arg Lys Lys Lys Asp
1790                1795                1800

Val Ser Gln Gly Thr Leu Pro Ser Ser Gly Ala Val Glu Pro Glu
1805                1810                1815

-continued

Pro Glu Pro Gln Gly Thr Pro Gly Arg Leu Arg Leu Arg Thr Gln
    1820            1825                1830

Pro Pro Glu Pro Ala Ala Glu Glu Thr Pro Ser Arg Thr Lys Val
    1835            1840                1845

Arg Leu Ser Ser Val Arg Lys Gly Thr Pro Arg Arg Leu Lys Lys
    1850            1855                1860

Ser Val Glu Asn Gly Gln Ser Ile Glu Ile Leu Asp Asp Leu Lys
    1865            1870                1875

Gly Ser Glu Ala Ala Ser His Asp Gly Thr Val Thr Glu Leu Arg
    1880            1885                1890

Asn Ala Asn Leu Glu Asp Thr Gln Asn Met Glu Tyr Lys Gln Asp
    1895            1900                1905

Glu His Ser Asp Gln Gln Pro Pro Leu Lys Arg Lys Arg Val Arg
    1910            1915                1920

Glu Arg Glu Val Ser Val Ser Ser Val Thr Glu Glu Pro Lys Leu
    1925            1930                1935

Asp Ser Ser Gln Leu Pro Leu Gln Thr Gly Leu Asp Val Pro Ala
    1940            1945                1950

Thr Pro Arg Lys Arg Gly Arg Pro Arg Lys Val Val Pro Leu Glu
    1955            1960                1965

Ala Asp Gly Gly Thr Thr Gly Lys Glu Gln Thr Ser Pro Gln Lys
    1970            1975                1980

Lys Asp Val Pro Val Val Arg Arg Ser Thr Arg Asn Thr Pro Ala
    1985            1990                1995

Arg Asn Val Ser Thr Leu Lys Lys Ser Val Leu Val Pro Asn Lys
    2000            2005                2010

Glu Ala Ala Leu Val Val Thr Ser Lys Arg Arg Pro Thr Lys Lys
    2015            2020                2025

Ser Ala Glu Glu Ser Ser Lys Asp Pro Ser Ala Ala Val Ser Asp
    2030            2035                2040

Trp Ala Gly Gly Ala Ala His Thr Glu Ser Ala Asp Arg Arg Asp
    2045            2050                2055

Gly Leu Leu Ala Ala Ala Ala Leu Thr Pro Ser Ala Gln Gly Thr
    2060            2065                2070

Arg Thr Arg Ser Arg Arg Thr Met Leu Leu Thr Asp Ile Ser Glu
    2075            2080                2085

Pro Lys Thr Glu Pro Leu Phe Pro Pro Pro Ser Val Lys Val Pro
    2090            2095                2100

Lys Lys Lys Ser Lys Ala Glu Asn Met Glu Ala Ala Ala Gln Leu
    2105            2110                2115

Lys Glu Leu Val Ser Asp Leu Ser Ser Gln Phe Val Val Ser Pro
    2120            2125                2130

Pro Ala Leu Arg Thr Arg Gln Lys Ser Ile Ser Asn Thr Ser Lys
    2135            2140                2145

Leu Leu Gly Glu Leu Glu Ser Asp Pro Lys Pro Leu Glu Ile Ile
    2150            2155                2160

Glu Gln Lys Pro Lys Arg Ser Arg Thr Val Lys Thr Arg Ala Ser
    2165            2170                2175

Arg Asn Thr Gly Lys Gly Ser Ser Trp Ser Pro Pro Val Glu
    2180            2185                2190

Ile Lys Leu Val Ser Pro Leu Ala Ser Pro Val Asp Glu Ile Lys
    2195            2200                2205

Thr Gly Lys Pro Arg Lys Thr Ala Glu Ile Ala Gly Lys Thr Leu

```
                    2210                 2215                  2220
Gly Arg  Gly Arg Lys Lys Pro  Ser Ser Phe Pro Lys  Gln Ile Leu
    2225                 2230                      2235

Arg Arg  Lys Met Leu
    2240

<210> SEQ ID NO 13
<211> LENGTH: 7215
<212> TYPE: DNA
<213> ORGANISM: Homo sapiens
<220> FEATURE:
<221> NAME/KEY: CDS
<222> LOCATION: (125)..(6922)

<400> SEQUENCE: 13
tgcggctcga gggggccagc gctgacggtg gcgggtacgg caggctcgcg ggcgccgggc      60
ttcgttacat aatctcggac cggaggagcg gtggcacatg gcggcggaac ggcgctgtgg     120 aagt atg cga gac tta aga gct caa gtg act agt ggt ctc ctg cca ttt     169
     Met Arg Asp Leu Arg Ala Gln Val Thr Ser Gly Leu Leu Pro Phe
     1               5                   10                  15 cca gaa gtg act ctt caa gcc ctt gga gaa gac gaa ata aca tta gaa     217
Pro Glu Val Thr Leu Gln Ala Leu Gly Glu Asp Glu Ile Thr Leu Glu
                20                  25                  30 tct gtg ctt cgt gga aag ttt gct gcg ggg aaa aat gga ctt gct tgc     265
Ser Val Leu Arg Gly Lys Phe Ala Ala Gly Lys Asn Gly Leu Ala Cys
            35                  40                  45 ttg gct tgt ggt cca caa ctt gag gta gta aac tct ata aca gga gag     313
Leu Ala Cys Gly Pro Gln Leu Glu Val Val Asn Ser Ile Thr Gly Glu
        50                  55                  60 cga ttg tct gct tac aga ttc agt gga gtc aat gaa cag cct cct gta     361
Arg Leu Ser Ala Tyr Arg Phe Ser Gly Val Asn Glu Gln Pro Pro Val
    65                  70                  75 gtt tta gct gtg aaa gaa ttc tct tgg cag aag aga act gga tta tta     409
Val Leu Ala Val Lys Glu Phe Ser Trp Gln Lys Arg Thr Gly Leu Leu
80                  85                  90                  95 ata gga ttg gaa gaa aca gaa ggg agt gtt ctc tgt ctt tat gac ctt     457
Ile Gly Leu Glu Glu Thr Glu Gly Ser Val Leu Cys Leu Tyr Asp Leu
                100                 105                 110 gga ata tca aaa gta gtt aaa gca gtt gtt ctt cct gga agg gta aca     505
Gly Ile Ser Lys Val Val Lys Ala Val Val Leu Pro Gly Arg Val Thr
            115                 120                 125 gct att gaa cct ata att aat cat gga gga gcc agt gca agc act cag     553
Ala Ile Glu Pro Ile Ile Asn His Gly Gly Ala Ser Ala Ser Thr Gln
        130                 135                 140 cat tta cat cca agt ctg cga tgg ctt ttt gga gtg gca gct gtg gtc     601
His Leu His Pro Ser Leu Arg Trp Leu Phe Gly Val Ala Ala Val Val
    145                 150                 155 act gat gtt gga cag atc ctt ctt att gac cta tgt ttg gat gac ttg     649
Thr Asp Val Gly Gln Ile Leu Leu Ile Asp Leu Cys Leu Asp Asp Leu
160                 165                 170                 175 tca tgc aat caa aat gaa gtt gaa gca tca gat ctt gaa gtt cta act     697
Ser Cys Asn Gln Asn Glu Val Glu Ala Ser Asp Leu Glu Val Leu Thr
                180                 185                 190 ggt atc cca gct gaa gta cca cac att aga gaa agt gtg atg aga gaa     745
Gly Ile Pro Ala Glu Val Pro His Ile Arg Glu Ser Val Met Arg Glu
            195                 200                 205 ggg cgc cat ctg tgt ttc cag tta gta agt cca aca gga aca gcc gtt     793
Gly Arg His Leu Cys Phe Gln Leu Val Ser Pro Thr Gly Thr Ala Val
        210                 215                 220 tca act ctt agt tac ata agc agg aca aat cag ctt gct gca ggt ttt     841
```

-continued

```
                Ser Thr Leu Ser Tyr Ile Ser Arg Thr Asn Gln Leu Ala Ala Gly Phe
                    225                 230                 235 tct gat ggc tat cta gca ctt tgg aac atg aaa agc atg aaa aga gaa        889
Ser Asp Gly Tyr Leu Ala Leu Trp Asn Met Lys Ser Met Lys Arg Glu
240                 245                 250                 255 tat tac ata caa ttg gaa agt gga caa gtt cct gta tat gct gtc act        937
Tyr Tyr Ile Gln Leu Glu Ser Gly Gln Val Pro Val Tyr Ala Val Thr
                260                 265                 270 ttt caa gaa cct gag aat gat cgt cgg aat tgc tgc tac ttg tgg gct        985
Phe Gln Glu Pro Glu Asn Asp Arg Arg Asn Cys Cys Tyr Leu Trp Ala
            275                 280                 285 gtt cag tct aca caa gat agt gaa ggg gat gtt ttg agt ttg cat ctg        1033
Val Gln Ser Thr Gln Asp Ser Glu Gly Asp Val Leu Ser Leu His Leu
        290                 295                 300 ctg cag ctg gcc ttt ggt aat aga aag tgt ttg gca tca gga caa atc        1081
Leu Gln Leu Ala Phe Gly Asn Arg Lys Cys Leu Ala Ser Gly Gln Ile
    305                 310                 315 tta tat gag ggg tta gaa tac tgt gaa gaa aga tac acc ctg gac ctg        1129
Leu Tyr Glu Gly Leu Glu Tyr Cys Glu Glu Arg Tyr Thr Leu Asp Leu
320                 325                 330                 335 aca ggt ggc atg ttc cct ttg agg gga cag acg agt aat acc aaa ttg        1177
Thr Gly Gly Met Phe Pro Leu Arg Gly Gln Thr Ser Asn Thr Lys Leu
                340                 345                 350 ttg gga tgc cag agt ata gag aaa ttt cga tct cat ggt gac agg gag        1225
Leu Gly Cys Gln Ser Ile Glu Lys Phe Arg Ser His Gly Asp Arg Glu
            355                 360                 365 gaa ggc gtg aat gaa gct cta tcg cct gac act agt gtt tca gtc ttt        1273
Glu Gly Val Asn Glu Ala Leu Ser Pro Asp Thr Ser Val Ser Val Phe
        370                 375                 380 acc tgg cag gtg aat ata tat gga cag gga aag cct tct gta tat ttg        1321
Thr Trp Gln Val Asn Ile Tyr Gly Gln Gly Lys Pro Ser Val Tyr Leu
    385                 390                 395 ggg ctt ttt gat ata aat cgt tgg tat cat gca caa atg cca gat tcg        1369
Gly Leu Phe Asp Ile Asn Arg Trp Tyr His Ala Gln Met Pro Asp Ser
400                 405                 410                 415 tta agg tca gga gaa tat cta cat aat tgc tct tat ttt gca ctg tgg        1417
Leu Arg Ser Gly Glu Tyr Leu His Asn Cys Ser Tyr Phe Ala Leu Trp
                420                 425                 430 tca ttg gag tct gtt gta agt agg act tct cca cat ggc atc ttg gat        1465
Ser Leu Glu Ser Val Val Ser Arg Thr Ser Pro His Gly Ile Leu Asp
            435                 440                 445 ata tta gta cat gag aga agt tta aat aga gga gtc cct cct tca tat        1513
Ile Leu Val His Glu Arg Ser Leu Asn Arg Gly Val Pro Pro Ser Tyr
        450                 455                 460 cca cct ccc gag cag ttt ttt aat cca agc act tat aat ttt gat gcc        1561
Pro Pro Pro Glu Gln Phe Phe Asn Pro Ser Thr Tyr Asn Phe Asp Ala
    465                 470                 475 act tgt ttg tta aac tcg gga gtt gtt cat tta act tgt act ggc ttt        1609
Thr Cys Leu Leu Asn Ser Gly Val Val His Leu Thr Cys Thr Gly Phe
480                 485                 490                 495 cag aag gag act ttg act ttt tta aag aaa tca ggt cca tca ctc aat        1657
Gln Lys Glu Thr Leu Thr Phe Leu Lys Lys Ser Gly Pro Ser Leu Asn
                500                 505                 510 gaa ctc att cct gat ggt tat aat cga tgt ctt gta gct ggc ctt ctt        1705
Glu Leu Ile Pro Asp Gly Tyr Asn Arg Cys Leu Val Ala Gly Leu Leu
            515                 520                 525 tcc cca aga ttt gtt gat gtt cag cct tcc agt tta agc caa gaa gaa        1753
Ser Pro Arg Phe Val Asp Val Gln Pro Ser Ser Leu Ser Gln Glu Glu
        530                 535                 540 cag tta gaa gct ata ttg tca gca gca att cag act agt tcc ctg gga        1801
Gln Leu Glu Ala Ile Leu Ser Ala Ala Ile Gln Thr Ser Ser Leu Gly
```

-continued

```
                Gln Leu Glu Ala Ile Leu Ser Ala Ala Ile Gln Thr Ser Ser Leu Gly
                545                 550                 555 ctt ttg act ggt tat atc cga aga tgg ata aca gaa gaa caa cca aat       1849
Leu Leu Thr Gly Tyr Ile Arg Arg Trp Ile Thr Glu Glu Gln Pro Asn
560                 565                 570                 575 tct gcc act aat ttg cgc ttt gtt ctt gaa tgg acg tgg aat aaa gtg       1897
Ser Ala Thr Asn Leu Arg Phe Val Leu Glu Trp Thr Trp Asn Lys Val
                580                 585                 590 gtt ctc aca aaa gag gaa ttt gac aga cta tgt gtg cca tta ttt gat       1945
Val Leu Thr Lys Glu Glu Phe Asp Arg Leu Cys Val Pro Leu Phe Asp
            595                 600                 605 ggt tcg tgt cat ttc atg gat cca caa act ata cag tct atc cag caa       1993
Gly Ser Cys His Phe Met Asp Pro Gln Thr Ile Gln Ser Ile Gln Gln
        610                 615                 620 tgc tat ttg ctt ctt agc aat ctt aat ata gtc ttg agc tgt ttt gca       2041
Cys Tyr Leu Leu Leu Ser Asn Leu Asn Ile Val Leu Ser Cys Phe Ala
    625                 630                 635 tca gaa gcc cga gag atc gct gag aga gga ctg ata gac tta agc aat       2089
Ser Glu Ala Arg Glu Ile Ala Glu Arg Gly Leu Ile Asp Leu Ser Asn
640                 645                 650                 655 aag ttt gtg gtt tcc cac ctc atc tgt cag tat gca caa gtg gtt ctt       2137
Lys Phe Val Val Ser His Leu Ile Cys Gln Tyr Ala Gln Val Val Leu
                660                 665                 670 tgg ttc tct cat tct ggg ctt tta cca gaa ggc ata gat gat tct gtg       2185
Trp Phe Ser His Ser Gly Leu Leu Pro Glu Gly Ile Asp Asp Ser Val
            675                 680                 685 cag ttg tca agg tta tgc tac aac tac cct gta att cag aac tac tac       2233
Gln Leu Ser Arg Leu Cys Tyr Asn Tyr Pro Val Ile Gln Asn Tyr Tyr
        690                 695                 700 acc agt cgt cga cag aag ttt gag cgt tta tca aga ggg aag tgg aat       2281
Thr Ser Arg Arg Gln Lys Phe Glu Arg Leu Ser Arg Gly Lys Trp Asn
705                 710                 715 ccc gat tgc ttg atg att gat gga ctg gtt tct cag tta gga gag cga       2329
Pro Asp Cys Leu Met Ile Asp Gly Leu Val Ser Gln Leu Gly Glu Arg
720                 725                 730                 735 att gag aag ttg tgg aaa cga gat gaa gga ggc aca gga aaa tat cct       2377
Ile Glu Lys Leu Trp Lys Arg Asp Glu Gly Gly Thr Gly Lys Tyr Pro
                740                 745                 750 cct gct agt ctg cat gca gta ctt gat atg tac cta tta gac ggc gtt       2425
Pro Ala Ser Leu His Ala Val Leu Asp Met Tyr Leu Leu Asp Gly Val
            755                 760                 765 act gaa gca gcc aaa cac tct att acc att tat ttg cta ctt gat att       2473
Thr Glu Ala Ala Lys His Ser Ile Thr Ile Tyr Leu Leu Leu Asp Ile
        770                 775                 780 atg tat tcc ttt ccc aac aaa aca gac act ccc att gaa tct ttc cca       2521
Met Tyr Ser Phe Pro Asn Lys Thr Asp Thr Pro Ile Glu Ser Phe Pro
    785                 790                 795 act gta ttt gcc att tct tgg ggc caa gtt aaa ctt att cag ggg ttt       2569
Thr Val Phe Ala Ile Ser Trp Gly Gln Val Lys Leu Ile Gln Gly Phe
800                 805                 810                 815 tgg ttg ata gat cat aat gac tat gag agt ggt ttg gat ctt ttg ttt       2617
Trp Leu Ile Asp His Asn Asp Tyr Glu Ser Gly Leu Asp Leu Leu Phe
                820                 825                 830 cat cca gct act gca aaa cct ttg tca tgg caa cat tca aag att att       2665
His Pro Ala Thr Ala Lys Pro Leu Ser Trp Gln His Ser Lys Ile Ile
            835                 840                 845 cag gca ttc atg agt cag ggc gag cac aga caa gcc ctc aga tat att       2713
Gln Ala Phe Met Ser Gln Gly Glu His Arg Gln Ala Leu Arg Tyr Ile
        850                 855                 860 cag aca atg aag cca aca gtg tcc agt ggt aac gat gtt atc ctt cac       2761
```

```
                Gln Thr Met Lys Pro Thr Val Ser Ser Gly Asn Asp Val Ile Leu His
                    865                 870                 875 ctc act gtt ttg ctt ttt aat agg tgt atg gtt gaa gcc tgg aat ttt        2809
Leu Thr Val Leu Leu Phe Asn Arg Cys Met Val Glu Ala Trp Asn Phe
880                 885                 890                 895 ttg cgg caa cat tgc aat agg ttg aat ata gag gag tta ctg aag cac        2857
Leu Arg Gln His Cys Asn Arg Leu Asn Ile Glu Glu Leu Leu Lys His
                900                 905                 910 atg tat gaa gtc tgt cag gaa atg ggc ttg atg gaa gat tta ctg aag        2905
Met Tyr Glu Val Cys Gln Glu Met Gly Leu Met Glu Asp Leu Leu Lys
                915                 920                 925 tta cca ttt aca gac act gag cag gaa tgt tta gtg aaa ttt ttg cag        2953
Leu Pro Phe Thr Asp Thr Glu Gln Glu Cys Leu Val Lys Phe Leu Gln
            930                 935                 940 tcc agt gcc agc gtt cag aat cat gaa ttc ctt tta gtg cac cat ttg        3001
Ser Ser Ala Ser Val Gln Asn His Glu Phe Leu Leu Val His His Leu
945                 950                 955 cag cgt gcc aat tat gtg cct gcc ttg aag ctg aac caa act ctg aag        3049
Gln Arg Ala Asn Tyr Val Pro Ala Leu Lys Leu Asn Gln Thr Leu Lys
960                 965                 970                 975 att aat gtt atg aat gat cgt gat cct cgt ttg cgg gag aga tca ctg        3097
Ile Asn Val Met Asn Asp Arg Asp Pro Arg Leu Arg Glu Arg Ser Leu
                980                 985                 990 gct cga aat tct ata tta gac cag tat gga aaa atc ctt cct aga gtc        3145
Ala Arg Asn Ser Ile Leu Asp Gln Tyr Gly Lys Ile Leu Pro Arg Val
                995                 1000                1005 cat cga aaa tta gcc att gaa cga gct aag cct tat cat ctg tca            3190
His Arg Lys Leu Ala Ile Glu Arg Ala Lys Pro Tyr His Leu Ser
        1010                1015                1020 aca tca tca gtt ttt cga tta gtt tct aga ccc aaa cca tta tca            3235
Thr Ser Ser Val Phe Arg Leu Val Ser Arg Pro Lys Pro Leu Ser
        1025                1030                1035 gca gtt cca aag caa gtt gta aca gga act gtg ttg aca aga tct            3280
Ala Val Pro Lys Gln Val Val Thr Gly Thr Val Leu Thr Arg Ser
        1040                1045                1050 gtt ttc atc aac aat gtg tta tct aaa att gga gaa gtt tgg gca            3325
Val Phe Ile Asn Asn Val Leu Ser Lys Ile Gly Glu Val Trp Ala
        1055                1060                1065 agc aaa gaa cct ata aat agc acc aca cct ttc aat agt tct aaa            3370
Ser Lys Glu Pro Ile Asn Ser Thr Thr Pro Phe Asn Ser Ser Lys
        1070                1075                1080 ata gaa gaa cca tct cct ata gtg tat tcg ctc cca gct cca gag            3415
Ile Glu Glu Pro Ser Pro Ile Val Tyr Ser Leu Pro Ala Pro Glu
        1085                1090                1095 ctg cct gag gca ttt ttt gga aca cca att tca aaa gca tca caa            3460
Leu Pro Glu Ala Phe Phe Gly Thr Pro Ile Ser Lys Ala Ser Gln
        1100                1105                1110 aaa att tct aga ctg cta gat ttg gtt gtt cag cct gtc ccc cgg            3505
Lys Ile Ser Arg Leu Leu Asp Leu Val Val Gln Pro Val Pro Arg
        1115                1120                1125 cct tct cag tgt tcg gag ttt att cag caa agc tcc atg aaa tct            3550
Pro Ser Gln Cys Ser Glu Phe Ile Gln Gln Ser Ser Met Lys Ser
        1130                1135                1140 cct ttg tac cta gta tcc cgt tca ctg ccc tca agt tcg caa tta            3595
Pro Leu Tyr Leu Val Ser Arg Ser Leu Pro Ser Ser Ser Gln Leu
        1145                1150                1155 aaa gga tcg cct cag gcc atc tcc agg gct tca gaa tta cat ttg            3640
Lys Gly Ser Pro Gln Ala Ile Ser Arg Ala Ser Glu Leu His Leu
        1160                1165                1170 ctt gaa act cct ctt gta gtt aag aaa gct aaa agt ttg gcc atg            3685
```

```
                    Leu Glu Thr Pro Leu Val Val Lys Lys Ala Lys Ser Leu Ala Met
                        1175            1180                1185 tca gtt act act tct gga ttt tct gag ttc act cct cag tcc atc          3730
Ser Val Thr Thr Ser Gly Phe Ser Glu Phe Thr Pro Gln Ser Ile
        1190            1195                1200 ctg agg tct act cct cga tca aca cct tta gca tct ccc tct cca          3775
Leu Arg Ser Thr Pro Arg Ser Thr Pro Leu Ala Ser Pro Ser Pro
        1205            1210                1215 tca cct gga agg tct cct caa cga ctt aaa gaa act aga att tca          3820
Ser Pro Gly Arg Ser Pro Gln Arg Leu Lys Glu Thr Arg Ile Ser
        1220            1225                1230 ttt gtg gaa gaa gat gtc cac cca aaa tgg att cct ggg gct gca          3865
Phe Val Glu Glu Asp Val His Pro Lys Trp Ile Pro Gly Ala Ala
        1235            1240                1245 gat gat agc aaa tta gaa gta ttt act aca cct aaa aaa tgt gca          3910
Asp Asp Ser Lys Leu Glu Val Phe Thr Thr Pro Lys Lys Cys Ala
        1250            1255                1260 gtt cca gtg gaa act gaa tgg ccg aag agc aaa gat agg acc aca          3955
Val Pro Val Glu Thr Glu Trp Pro Lys Ser Lys Asp Arg Thr Thr
        1265            1270                1275 tct ttt ttc ctg aac agc cct gaa aag gag cat caa gaa atg gat          4000
Ser Phe Phe Leu Asn Ser Pro Glu Lys Glu His Gln Glu Met Asp
        1280            1285                1290 gag ggg tca caa agt tta gag aaa ctg gat gtg agc aaa gga aac          4045
Glu Gly Ser Gln Ser Leu Glu Lys Leu Asp Val Ser Lys Gly Asn
        1295            1300                1305 agc agt gtt tca atc aca tcc gat gag act acc tta gag tat cag          4090
Ser Ser Val Ser Ile Thr Ser Asp Glu Thr Thr Leu Glu Tyr Gln
        1310            1315                1320 gat gca ccg tca ccg gaa gac ctt gaa gag act gtt ttc acg gcc          4135
Asp Ala Pro Ser Pro Glu Asp Leu Glu Glu Thr Val Phe Thr Ala
        1325            1330                1335 tct aag ccc aaa agc tct tcc act gca cta act act aat gta act          4180
Ser Lys Pro Lys Ser Ser Ser Thr Ala Leu Thr Thr Asn Val Thr
        1340            1345                1350 gaa caa act gaa aag gat gga gat aaa gat gta ttt gca tca gaa          4225
Glu Gln Thr Glu Lys Asp Gly Asp Lys Asp Val Phe Ala Ser Glu
        1355            1360                1365 gta act cct tca gac cta cag aaa caa atg ggc aat tta gaa gat          4270
Val Thr Pro Ser Asp Leu Gln Lys Gln Met Gly Asn Leu Glu Asp
        1370            1375                1380 gca gaa aca aag gat ctc tta gtt gca gca gag gca ttt tca gaa          4315
Ala Glu Thr Lys Asp Leu Leu Val Ala Ala Glu Ala Phe Ser Glu
        1385            1390                1395 ttg aat cac tta agc ccg gtt caa gga act gaa gct tct ctt tgt          4360
Leu Asn His Leu Ser Pro Val Gln Gly Thr Glu Ala Ser Leu Cys
        1400            1405                1410 gca cca tca gtc tat gaa ggg aaa atc ttc acc cag aag tcc aag          4405
Ala Pro Ser Val Tyr Glu Gly Lys Ile Phe Thr Gln Lys Ser Lys
        1415            1420                1425 gta cca gtg ttg gac gaa gga tta aca tct gtt gaa acc tac acc          4450
Val Pro Val Leu Asp Glu Gly Leu Thr Ser Val Glu Thr Tyr Thr
        1430            1435                1440 cct gca att aga gca aat gac aat aaa tct atg gct gat gtc ctt          4495
Pro Ala Ile Arg Ala Asn Asp Asn Lys Ser Met Ala Asp Val Leu
        1445            1450                1455 ggt gat ggt gga aac tcc tcg ctc act atc tct gaa ggt cct att          4540
Gly Asp Gly Gly Asn Ser Ser Leu Thr Ile Ser Glu Gly Pro Ile
        1460            1465                1470 gtc tct gag cgc agg ctt aac cag gaa gta gcg ctg aac tta aaa          4585
```

```
               Val Ser Glu Arg Arg Leu Asn Gln Glu Val Ala Leu Asn Leu Lys
                   1475                1480                1485 gaa gat cat gaa gta gaa gtt ggt gta cta aaa gaa agt gtt gac          4630
Glu Asp His Glu Val Glu Val Gly Val Leu Lys Glu Ser Val Asp
        1490                1495                1500 tta cca gaa gaa aag ctt cca att tct gac agc cct cct gat act          4675
Leu Pro Glu Glu Lys Leu Pro Ile Ser Asp Ser Pro Pro Asp Thr
        1505                1510                1515 caa gaa att cat gtg att gaa caa gaa aag ctt gaa gct caa gat          4720
Gln Glu Ile His Val Ile Glu Gln Glu Lys Leu Glu Ala Gln Asp
        1520                1525                1530 tca gga gaa gag gct agg aat ctt tca ttt aat gag tta tat ccc          4765
Ser Gly Glu Glu Ala Arg Asn Leu Ser Phe Asn Glu Leu Tyr Pro
        1535                1540                1545 tct gga aca ctt aag ctt cag tac aat ttt gat act att gac caa          4810
Ser Gly Thr Leu Lys Leu Gln Tyr Asn Phe Asp Thr Ile Asp Gln
        1550                1555                1560 cag ttt tgt gac tta gct gat aac aaa gac act gct gaa tgt gac          4855
Gln Phe Cys Asp Leu Ala Asp Asn Lys Asp Thr Ala Glu Cys Asp
        1565                1570                1575 att gct gaa gta gat ggg gaa ctt ttt gtg gct caa agc aac ttt          4900
Ile Ala Glu Val Asp Gly Glu Leu Phe Val Ala Gln Ser Asn Phe
        1580                1585                1590 acc ttg ata ttg gaa ggt gaa gaa gga gaa gtt gag cca ggt gat          4945
Thr Leu Ile Leu Glu Gly Glu Glu Gly Glu Val Glu Pro Gly Asp
        1595                1600                1605 ttt gca tca tct gat gtg tta cct aaa gca gct aac aca gca act          4990
Phe Ala Ser Ser Asp Val Leu Pro Lys Ala Ala Asn Thr Ala Thr
        1610                1615                1620 gaa gaa aaa ctt gta tgc agt ggg gaa aat gat aat cat gga caa          5035
Glu Glu Lys Leu Val Cys Ser Gly Glu Asn Asp Asn His Gly Gln
        1625                1630                1635 att gca aat ttg cca tct gcc gta act agt gac caa aag tcc caa          5080
Ile Ala Asn Leu Pro Ser Ala Val Thr Ser Asp Gln Lys Ser Gln
        1640                1645                1650 aaa gta gac act tta cca tat gtg cct gaa cct att aaa gta gca          5125
Lys Val Asp Thr Leu Pro Tyr Val Pro Glu Pro Ile Lys Val Ala
        1655                1660                1665 att gca gaa aat tta cta gat gta att aaa gac aca aga agt aaa          5170
Ile Ala Glu Asn Leu Leu Asp Val Ile Lys Asp Thr Arg Ser Lys
        1670                1675                1680 gaa att act tca gat aca atg gaa cag tcc att cat gaa aca ata          5215
Glu Ile Thr Ser Asp Thr Met Glu Gln Ser Ile His Glu Thr Ile
        1685                1690                1695 cct tta gtg agc caa aac ata atg tgt ccc act aaa ttg gtc aaa          5260
Pro Leu Val Ser Gln Asn Ile Met Cys Pro Thr Lys Leu Val Lys
        1700                1705                1710 tct gca ttt aag act gct cag gaa aca agc aca atg act atg aat          5305
Ser Ala Phe Lys Thr Ala Gln Glu Thr Ser Thr Met Thr Met Asn
        1715                1720                1725 gtc agc cag gtt gat gac gtg gtt tcc tcc aaa act cgt acg aga          5350
Val Ser Gln Val Asp Asp Val Val Ser Ser Lys Thr Arg Thr Arg
        1730                1735                1740 ggt caa cgt atc caa aac gtg aat gtc aaa tca gca caa cag gaa          5395
Gly Gln Arg Ile Gln Asn Val Asn Val Lys Ser Ala Gln Gln Glu
        1745                1750                1755 gca tca gca gat gtt gct act cct aag atg cca ggg cag tca gtc          5440
Ala Ser Ala Asp Val Ala Thr Pro Lys Met Pro Gly Gln Ser Val
        1760                1765                1770 agg aag aaa act agg aag gca aaa gaa att tct gaa gct tct gaa          5485
```

```
                Arg Lys Lys Thr Arg Lys Ala Lys Glu Ile Ser Glu Ala Ser Glu
                    1775            1780            1785 aac atc tat tct gat gtc aga gga cta ttt cag aac cag caa ata        5530
Asn Ile Tyr Ser Asp Val Arg Gly Leu Phe Gln Asn Gln Gln Ile
        1790            1795            1800 cct caa aat tct gtt acg cct agg aga gga agg aga aag aaa gaa        5575
Pro Gln Asn Ser Val Thr Pro Arg Arg Gly Arg Arg Lys Lys Glu
        1805            1810            1815 gtt aat cag gac ata cta gaa aac acc agt tct gtg gaa caa gaa        5620
Val Asn Gln Asp Ile Leu Glu Asn Thr Ser Ser Val Glu Gln Glu
        1820            1825            1830 tta cag atc act aca ggt agg gaa tca aaa aga tta aaa tca tct        5665
Leu Gln Ile Thr Thr Gly Arg Glu Ser Lys Arg Leu Lys Ser Ser
        1835            1840            1845 cag ctg ttg gaa cca gca gtt gaa gaa act act aaa aaa gaa gtt        5710
Gln Leu Leu Glu Pro Ala Val Glu Glu Thr Thr Lys Lys Glu Val
        1850            1855            1860 aag gtt tca tct gtt aca aaa agg act cct aga aga att aaa aga        5755
Lys Val Ser Ser Val Thr Lys Arg Thr Pro Arg Arg Ile Lys Arg
        1865            1870            1875 tct gta gaa aat cag gaa agt gtt gaa att ata aat gat cta aaa        5800
Ser Val Glu Asn Gln Glu Ser Val Glu Ile Ile Asn Asp Leu Lys
        1880            1885            1890 gtt agt acg gta aca agt cct agc aga atg atc aga aaa ttg aga        5845
Val Ser Thr Val Thr Ser Pro Ser Arg Met Ile Arg Lys Leu Arg
        1895            1900            1905 agt act aat tta gat gct tct gaa aat aca gga aat aag caa gat        5890
Ser Thr Asn Leu Asp Ala Ser Glu Asn Thr Gly Asn Lys Gln Asp
        1910            1915            1920 gat aaa tcc agt gac aag cag ctg cgt att aaa cat gtt aga agg        5935
Asp Lys Ser Ser Asp Lys Gln Leu Arg Ile Lys His Val Arg Arg
        1925            1930            1935 gtc aga ggg aga gaa gtt agt cca tca gat gtg aga gaa gac tcc        5980
Val Arg Gly Arg Glu Val Ser Pro Ser Asp Val Arg Glu Asp Ser
        1940            1945            1950 aac ctt gag tca tct cag ttg act gtt caa gca gaa ttt gat atg        6025
Asn Leu Glu Ser Ser Gln Leu Thr Val Gln Ala Glu Phe Asp Met
        1955            1960            1965 tct gcc ata cct aga aaa cgt ggt aga cca aga aaa atc aat cca        6070
Ser Ala Ile Pro Arg Lys Arg Gly Arg Pro Arg Lys Ile Asn Pro
        1970            1975            1980 tct gaa gat gta gga tct aag gct gtt aag gaa gag aga agc ccc        6115
Ser Glu Asp Val Gly Ser Lys Ala Val Lys Glu Glu Arg Ser Pro
        1985            1990            1995 aag aag aaa gaa gct ccc agc att aga agg aga tct aca aga aat        6160
Lys Lys Lys Glu Ala Pro Ser Ile Arg Arg Arg Ser Thr Arg Asn
        2000            2005            2010 acc cca gct aaa agt gaa aat gtt gat gtt gga aaa cca gct tta        6205
Thr Pro Ala Lys Ser Glu Asn Val Asp Val Gly Lys Pro Ala Leu
        2015            2020            2025 gga aaa tcc att tta gtg cca aac gag gaa ctt tcg atg gtg atg        6250
Gly Lys Ser Ile Leu Val Pro Asn Glu Glu Leu Ser Met Val Met
        2030            2035            2040 agc tct aag aaa aaa ctt aca aaa aag act gaa agt caa agc caa        6295
Ser Ser Lys Lys Lys Leu Thr Lys Lys Thr Glu Ser Gln Ser Gln
        2045            2050            2055 aaa cgt tca ttg cac tca gta tca gaa gaa cgc aca gat gaa atg        6340
Lys Arg Ser Leu His Ser Val Ser Glu Glu Arg Thr Asp Glu Met
        2060            2065            2070 aca cat aaa gaa aca aat gag cag gaa gaa aga ttg ctc gcc aca        6385
```

|  |  |  |  |  |  |  |  |  |  |  |  |  |  |  |
|---|---|---|---|---|---|---|---|---|---|---|---|---|---|---|
| Thr | His | Lys<br>2075 | Glu | Thr | Asn<br>2080 | Glu | Gln | Glu | Glu | Arg<br>2085 | Leu | Leu | Ala | Thr |

```
gct tcc ttc act aaa tca tcc cgc agc agc agg act cgg tct agc         6430
Ala Ser Phe Thr Lys Ser Ser Arg Ser Ser Arg Thr Arg Ser Ser
        2090                2095                2100 aag gcc atc ttg ttg ccg gac ctt tct gaa cca aac aat gag cct         6475
Lys Ala Ile Leu Leu Pro Asp Leu Ser Glu Pro Asn Asn Glu Pro
        2105                2110                2115 tta ttt tct cca gcg tca gaa gtt cca agg aaa gca aaa gct aaa         6520
Leu Phe Ser Pro Ala Ser Glu Val Pro Arg Lys Ala Lys Ala Lys
        2120                2125                2130 aaa ata gag gtt cct gca cag ctg aaa gaa tta gtt tcg gat tta         6565
Lys Ile Glu Val Pro Ala Gln Leu Lys Glu Leu Val Ser Asp Leu
        2135                2140                2145 tct tct cag ttt gtc atc tca cct cct gct tta agg agc aga caa         6610
Ser Ser Gln Phe Val Ile Ser Pro Pro Ala Leu Arg Ser Arg Gln
        2150                2155                2160 aaa aac aca tcc aat aag aac aag ctt gaa gat gaa ctg aaa gat         6655
Lys Asn Thr Ser Asn Lys Asn Lys Leu Glu Asp Glu Leu Lys Asp
        2165                2170                2175 gat gca caa tca gta gaa act ctg gga aag cca aaa gcg aaa cga         6700
Asp Ala Gln Ser Val Glu Thr Leu Gly Lys Pro Lys Ala Lys Arg
        2180                2185                2190 atc agg acg tca aaa aca aaa caa gca agc aaa aac aca gaa aaa         6745
Ile Arg Thr Ser Lys Thr Lys Gln Ala Ser Lys Asn Thr Glu Lys
        2195                2200                2205 gaa agt gct tgg tca ctt cct ccc ata gaa att cgg ctg att tcc         6790
Glu Ser Ala Trp Ser Leu Pro Pro Ile Glu Ile Arg Leu Ile Ser
        2210                2215                2220 ccc ttg gct agc cca gct gac gga gtc aag agc aaa cca aga aaa         6835
Pro Leu Ala Ser Pro Ala Asp Gly Val Lys Ser Lys Pro Arg Lys
        2225                2230                2235 act aca gaa gtg aca gga aca ggt ctt gga agg aac aga aag aaa         6880
Thr Thr Glu Val Thr Gly Thr Gly Leu Gly Arg Asn Arg Lys Lys
        2240                2245                2250 ctg tct tcc tat cca aag caa att tta cgc aga aaa atg ctg             6922
Leu Ser Ser Tyr Pro Lys Gln Ile Leu Arg Arg Lys Met Leu
        2255                2260                2265 taatttcttg ggaagatttt aatgtacacc tatttgtaaa gtcatcagaa tagtgtggat   6982
tattaaatat ctagtttgga agaaaataat ttatataaat tattgtaaat ttttatgtaa   7042
acagaaggtc ttcaataagt aaagtaactc catatggagt gattgtttca gtccaggcaa   7102
tttttctatt ttatattaag acttcataca tttatatatg taaatatggc ttattaatgg   7162
aatgttaaat aaaatgtata cttctcaaaa aaaaaaaaa aaaaaaaaaa aaa           7215

<210> SEQ ID NO 14
<211> LENGTH: 2266
<212> TYPE: PRT
<213> ORGANISM: Homo sapiens

<400> SEQUENCE: 14

Met Arg Asp Leu Arg Ala Gln Val Thr Ser Gly Leu Leu Pro Phe Pro
1               5                   10                  15

Glu Val Thr Leu Gln Ala Leu Gly Glu Asp Glu Ile Thr Leu Glu Ser
                20                  25                  30

Val Leu Arg Gly Lys Phe Ala Ala Gly Lys Asn Gly Leu Ala Cys Leu
        35                  40                  45

Ala Cys Gly Pro Gln Leu Glu Val Val Asn Ser Ile Thr Gly Glu Arg
    50                  55                  60
```

```
Leu Ser Ala Tyr Arg Phe Ser Gly Val Asn Glu Gln Pro Val Val
 65                  70                  75                  80

Leu Ala Val Lys Glu Phe Ser Trp Gln Lys Arg Thr Gly Leu Leu Ile
                     85                  90                  95

Gly Leu Glu Glu Thr Glu Gly Ser Val Leu Cys Leu Tyr Asp Leu Gly
                100                 105                 110

Ile Ser Lys Val Val Lys Ala Val Leu Pro Gly Arg Val Thr Ala
            115                 120                 125

Ile Glu Pro Ile Ile Asn His Gly Gly Ala Ser Ala Ser Thr Gln His
        130                 135                 140

Leu His Pro Ser Leu Arg Trp Leu Phe Gly Val Ala Ala Val Val Thr
145                 150                 155                 160

Asp Val Gly Gln Ile Leu Leu Ile Asp Leu Cys Leu Asp Asp Leu Ser
                165                 170                 175

Cys Asn Gln Asn Glu Val Glu Ala Ser Asp Leu Glu Val Leu Thr Gly
                180                 185                 190

Ile Pro Ala Glu Val Pro His Ile Arg Glu Ser Val Met Arg Glu Gly
            195                 200                 205

Arg His Leu Cys Phe Gln Leu Val Ser Pro Thr Gly Thr Ala Val Ser
        210                 215                 220

Thr Leu Ser Tyr Ile Ser Arg Thr Asn Gln Leu Ala Ala Gly Phe Ser
225                 230                 235                 240

Asp Gly Tyr Leu Ala Leu Trp Asn Met Lys Ser Met Lys Arg Glu Tyr
                245                 250                 255

Tyr Ile Gln Leu Glu Ser Gly Gln Val Pro Val Tyr Ala Val Thr Phe
                260                 265                 270

Gln Glu Pro Glu Asn Asp Arg Arg Asn Cys Cys Tyr Leu Trp Ala Val
            275                 280                 285

Gln Ser Thr Gln Asp Ser Glu Gly Asp Val Leu Ser Leu His Leu Leu
        290                 295                 300

Gln Leu Ala Phe Gly Asn Arg Lys Cys Leu Ala Ser Gly Gln Ile Leu
305                 310                 315                 320

Tyr Glu Gly Leu Glu Tyr Cys Glu Glu Arg Tyr Thr Leu Asp Leu Thr
                325                 330                 335

Gly Gly Met Phe Pro Leu Arg Gly Gln Thr Ser Asn Thr Lys Leu Leu
                340                 345                 350

Gly Cys Gln Ser Ile Glu Lys Phe Arg Ser His Gly Asp Arg Glu Glu
            355                 360                 365

Gly Val Asn Glu Ala Leu Ser Pro Asp Thr Ser Val Ser Val Phe Thr
        370                 375                 380

Trp Gln Val Asn Ile Tyr Gly Gln Gly Lys Pro Ser Val Tyr Leu Gly
385                 390                 395                 400

Leu Phe Asp Ile Asn Arg Trp Tyr His Ala Gln Met Pro Asp Ser Leu
                405                 410                 415

Arg Ser Gly Glu Tyr Leu His Asn Cys Ser Tyr Phe Ala Leu Trp Ser
                420                 425                 430

Leu Glu Ser Val Val Ser Arg Thr Ser Pro His Gly Ile Leu Asp Ile
            435                 440                 445

Leu Val His Glu Arg Ser Leu Asn Arg Gly Val Pro Pro Ser Tyr Pro
        450                 455                 460

Pro Pro Glu Gln Phe Phe Asn Pro Ser Thr Tyr Asn Phe Asp Ala Thr
465                 470                 475                 480

Cys Leu Leu Asn Ser Gly Val Val His Leu Thr Cys Thr Gly Phe Gln
```

```
                        485                 490                 495
Lys Glu Thr Leu Thr Phe Leu Lys Lys Ser Gly Pro Ser Leu Asn Glu
                    500                 505                 510

Leu Ile Pro Asp Gly Tyr Asn Arg Cys Leu Val Ala Gly Leu Leu Ser
                515                 520                 525

Pro Arg Phe Val Asp Val Gln Pro Ser Ser Leu Ser Gln Glu Glu Gln
            530                 535                 540

Leu Glu Ala Ile Leu Ser Ala Ala Ile Gln Thr Ser Ser Leu Gly Leu
545                 550                 555                 560

Leu Thr Gly Tyr Ile Arg Arg Trp Ile Thr Glu Glu Gln Pro Asn Ser
                565                 570                 575

Ala Thr Asn Leu Arg Phe Val Leu Glu Trp Thr Trp Asn Lys Val Val
                580                 585                 590

Leu Thr Lys Glu Glu Phe Asp Arg Leu Cys Val Pro Leu Phe Asp Gly
                595                 600                 605

Ser Cys His Phe Met Asp Pro Gln Thr Ile Gln Ser Ile Gln Gln Cys
            610                 615                 620

Tyr Leu Leu Leu Ser Asn Leu Asn Ile Val Leu Ser Cys Phe Ala Ser
625                 630                 635                 640

Glu Ala Arg Glu Ile Ala Glu Arg Gly Leu Ile Asp Leu Ser Asn Lys
                645                 650                 655

Phe Val Val Ser His Leu Ile Cys Gln Tyr Ala Gln Val Leu Leu Trp
                660                 665                 670

Phe Ser His Ser Gly Leu Leu Pro Glu Gly Ile Asp Asp Ser Val Gln
            675                 680                 685

Leu Ser Arg Leu Cys Tyr Asn Tyr Pro Val Ile Gln Asn Tyr Tyr Thr
            690                 695                 700

Ser Arg Arg Gln Lys Phe Glu Arg Leu Ser Arg Gly Lys Trp Asn Pro
705                 710                 715                 720

Asp Cys Leu Met Ile Asp Gly Leu Val Ser Gln Leu Gly Glu Arg Ile
                725                 730                 735

Glu Lys Leu Trp Lys Arg Asp Glu Gly Gly Thr Gly Lys Tyr Pro Pro
                740                 745                 750

Ala Ser Leu His Ala Val Leu Asp Met Tyr Leu Leu Asp Gly Val Thr
            755                 760                 765

Glu Ala Ala Lys His Ser Ile Thr Ile Tyr Leu Leu Leu Asp Ile Met
770                 775                 780

Tyr Ser Phe Pro Asn Lys Thr Asp Thr Pro Ile Glu Ser Phe Pro Thr
785                 790                 795                 800

Val Phe Ala Ile Ser Trp Gly Gln Val Lys Leu Ile Gln Gly Phe Trp
                805                 810                 815

Leu Ile Asp His Asn Asp Tyr Glu Ser Gly Leu Asp Leu Leu Phe His
                820                 825                 830

Pro Ala Thr Ala Lys Pro Leu Ser Trp Gln His Ser Lys Ile Ile Gln
            835                 840                 845

Ala Phe Met Ser Gln Gly Glu His Arg Gln Ala Leu Arg Tyr Ile Gln
            850                 855                 860

Thr Met Lys Pro Thr Val Ser Ser Gly Asn Asp Val Ile Leu His Leu
865                 870                 875                 880

Thr Val Leu Leu Phe Asn Arg Cys Met Val Glu Ala Trp Asn Phe Leu
                885                 890                 895

Arg Gln His Cys Asn Arg Leu Asn Ile Glu Glu Leu Leu Lys His Met
                900                 905                 910
```

-continued

```
Tyr Glu Val Cys Gln Glu Met Gly Leu Met Glu Asp Leu Leu Lys Leu
        915                 920                 925

Pro Phe Thr Asp Thr Glu Gln Glu Cys Leu Val Lys Phe Leu Gln Ser
    930                 935                 940

Ser Ala Ser Val Gln Asn His Glu Phe Leu Leu Val His His Leu Gln
945                 950                 955                 960

Arg Ala Asn Tyr Val Pro Ala Leu Lys Leu Asn Gln Thr Leu Lys Ile
                965                 970                 975

Asn Val Met Asn Asp Arg Asp Pro Arg Leu Arg Glu Arg Ser Leu Ala
                980                 985                 990

Arg Asn Ser Ile Leu Asp Gln Tyr Gly Lys Ile Leu Pro Arg Val His
                995                 1000                1005

Arg Lys Leu Ala Ile Glu Arg Ala Lys Pro Tyr His Leu Ser Thr
    1010                1015                1020

Ser Ser Val Phe Arg Leu Val Ser Arg Pro Lys Pro Leu Ser Ala
    1025                1030                1035

Val Pro Lys Gln Val Val Thr Gly Thr Val Leu Thr Arg Ser Val
    1040                1045                1050

Phe Ile Asn Asn Val Leu Ser Lys Ile Gly Glu Val Trp Ala Ser
    1055                1060                1065

Lys Glu Pro Ile Asn Ser Thr Thr Pro Phe Asn Ser Ser Lys Ile
    1070                1075                1080

Glu Glu Pro Ser Pro Ile Val Tyr Ser Leu Pro Ala Pro Glu Leu
    1085                1090                1095

Pro Glu Ala Phe Phe Gly Thr Pro Ile Ser Lys Ala Ser Gln Lys
    1100                1105                1110

Ile Ser Arg Leu Leu Asp Leu Val Val Gln Pro Val Pro Arg Pro
    1115                1120                1125

Ser Gln Cys Ser Glu Phe Ile Gln Gln Ser Ser Met Lys Ser Pro
    1130                1135                1140

Leu Tyr Leu Val Ser Arg Ser Leu Pro Ser Ser Ser Gln Leu Lys
    1145                1150                1155

Gly Ser Pro Gln Ala Ile Ser Arg Ala Ser Glu Leu His Leu Leu
    1160                1165                1170

Glu Thr Pro Leu Val Val Lys Lys Ala Lys Ser Leu Ala Met Ser
    1175                1180                1185

Val Thr Thr Ser Gly Phe Ser Glu Phe Thr Pro Gln Ser Ile Leu
    1190                1195                1200

Arg Ser Thr Pro Arg Ser Thr Pro Leu Ala Ser Pro Ser Pro Ser
    1205                1210                1215

Pro Gly Arg Ser Pro Gln Arg Leu Lys Glu Thr Arg Ile Ser Phe
    1220                1225                1230

Val Glu Glu Asp Val His Pro Lys Trp Ile Pro Gly Ala Ala Asp
    1235                1240                1245

Asp Ser Lys Leu Glu Val Phe Thr Thr Pro Lys Lys Cys Ala Val
    1250                1255                1260

Pro Val Glu Thr Glu Trp Pro Lys Ser Lys Asp Arg Thr Thr Ser
    1265                1270                1275

Phe Phe Leu Asn Ser Pro Glu Lys Glu His Gln Glu Met Asp Glu
    1280                1285                1290

Gly Ser Gln Ser Leu Glu Lys Leu Asp Val Ser Lys Gly Asn Ser
    1295                1300                1305

Ser Val Ser Ile Thr Ser Asp Glu Thr Thr Leu Glu Tyr Gln Asp
    1310                1315                1320
```

```
Ala Pro Ser Pro Glu Asp Leu Glu Glu Thr Val Phe Thr Ala Ser
    1325             1330                 1335

Lys Pro Lys Ser Ser Thr Ala Leu Thr Thr Asn Val Thr Glu
    1340             1345                 1350

Gln Thr Glu Lys Asp Gly Asp Lys Asp Val Phe Ala Ser Glu Val
    1355             1360                 1365

Thr Pro Ser Asp Leu Gln Lys Gln Met Gly Asn Leu Glu Asp Ala
    1370             1375                 1380

Glu Thr Lys Asp Leu Leu Val Ala Ala Glu Ala Phe Ser Glu Leu
    1385             1390                 1395

Asn His Leu Ser Pro Val Gln Gly Thr Glu Ala Ser Leu Cys Ala
    1400             1405                 1410

Pro Ser Val Tyr Glu Gly Lys Ile Phe Thr Gln Lys Ser Lys Val
    1415             1420                 1425

Pro Val Leu Asp Glu Gly Leu Thr Ser Val Glu Thr Tyr Thr Pro
    1430             1435                 1440

Ala Ile Arg Ala Asn Asp Asn Lys Ser Met Ala Asp Val Leu Gly
    1445             1450                 1455

Asp Gly Gly Asn Ser Ser Leu Thr Ile Ser Glu Gly Pro Ile Val
    1460             1465                 1470

Ser Glu Arg Arg Leu Asn Gln Glu Val Ala Leu Asn Leu Lys Glu
    1475             1480                 1485

Asp His Glu Val Glu Val Gly Val Leu Lys Glu Ser Val Asp Leu
    1490             1495                 1500

Pro Glu Glu Lys Leu Pro Ile Ser Asp Ser Pro Asp Thr Gln
    1505             1510                 1515

Glu Ile His Val Ile Glu Gln Glu Lys Leu Glu Ala Gln Asp Ser
    1520             1525                 1530

Gly Glu Glu Ala Arg Asn Leu Ser Phe Asn Glu Leu Tyr Pro Ser
    1535             1540                 1545

Gly Thr Leu Lys Leu Gln Tyr Asn Phe Asp Thr Ile Asp Gln Gln
    1550             1555                 1560

Phe Cys Asp Leu Ala Asp Asn Lys Asp Thr Ala Glu Cys Asp Ile
    1565             1570                 1575

Ala Glu Val Asp Gly Glu Leu Phe Val Ala Gln Ser Asn Phe Thr
    1580             1585                 1590

Leu Ile Leu Glu Gly Glu Glu Gly Glu Val Glu Pro Gly Asp Phe
    1595             1600                 1605

Ala Ser Ser Asp Val Leu Pro Lys Ala Ala Asn Thr Ala Thr Glu
    1610             1615                 1620

Glu Lys Leu Val Cys Ser Gly Glu Asn Asp Asn His Gly Gln Ile
    1625             1630                 1635

Ala Asn Leu Pro Ser Ala Val Thr Ser Asp Gln Lys Ser Gln Lys
    1640             1645                 1650

Val Asp Thr Leu Pro Tyr Val Pro Glu Pro Ile Lys Val Ala Ile
    1655             1660                 1665

Ala Glu Asn Leu Leu Asp Val Ile Lys Asp Thr Arg Ser Lys Glu
    1670             1675                 1680

Ile Thr Ser Asp Thr Met Glu Gln Ser Ile His Glu Thr Ile Pro
    1685             1690                 1695

Leu Val Ser Gln Asn Ile Met Cys Pro Thr Lys Leu Val Lys Ser
    1700             1705                 1710

Ala Phe Lys Thr Ala Gln Glu Thr Ser Thr Met Thr Met Asn Val
```

```
              1715                1720                1725

Ser Gln Val Asp Val Val Ser Ser Lys Thr Arg Thr Arg Gly
    1730                1735                1740

Gln Arg Ile Gln Asn Val Asn Val Lys Ser Ala Gln Gln Glu Ala
    1745                1750                1755

Ser Ala Asp Val Ala Thr Pro Lys Met Pro Gly Gln Ser Val Arg
    1760                1765                1770

Lys Lys Thr Arg Lys Ala Lys Glu Ile Ser Glu Ala Ser Glu Asn
    1775                1780                1785

Ile Tyr Ser Asp Val Arg Gly Leu Phe Gln Asn Gln Gln Ile Pro
    1790                1795                1800

Gln Asn Ser Val Thr Pro Arg Arg Gly Arg Arg Lys Lys Glu Val
    1805                1810                1815

Asn Gln Asp Ile Leu Glu Asn Thr Ser Ser Val Glu Gln Glu Leu
    1820                1825                1830

Gln Ile Thr Thr Gly Arg Glu Ser Lys Arg Leu Lys Ser Ser Gln
    1835                1840                1845

Leu Leu Glu Pro Ala Val Glu Glu Thr Thr Lys Lys Glu Val Lys
    1850                1855                1860

Val Ser Ser Val Thr Lys Arg Thr Pro Arg Arg Ile Lys Arg Ser
    1865                1870                1875

Val Glu Asn Gln Glu Ser Val Glu Ile Ile Asn Asp Leu Lys Val
    1880                1885                1890

Ser Thr Val Thr Ser Pro Ser Arg Met Ile Arg Lys Leu Arg Ser
    1895                1900                1905

Thr Asn Leu Asp Ala Ser Glu Asn Thr Gly Asn Lys Gln Asp Asp
    1910                1915                1920

Lys Ser Ser Asp Lys Gln Leu Arg Ile Lys His Val Arg Arg Val
    1925                1930                1935

Arg Gly Arg Glu Val Ser Pro Ser Asp Val Arg Glu Asp Ser Asn
    1940                1945                1950

Leu Glu Ser Ser Gln Leu Thr Val Gln Ala Glu Phe Asp Met Ser
    1955                1960                1965

Ala Ile Pro Arg Lys Arg Gly Arg Pro Arg Lys Ile Asn Pro Ser
    1970                1975                1980

Glu Asp Val Gly Ser Lys Ala Val Lys Glu Glu Arg Ser Pro Lys
    1985                1990                1995

Lys Lys Glu Ala Pro Ser Ile Arg Arg Arg Ser Thr Arg Asn Thr
    2000                2005                2010

Pro Ala Lys Ser Glu Asn Val Asp Val Gly Lys Pro Ala Leu Gly
    2015                2020                2025

Lys Ser Ile Leu Val Pro Asn Glu Glu Leu Ser Met Val Met Ser
    2030                2035                2040

Ser Lys Lys Lys Leu Thr Lys Lys Thr Glu Ser Gln Ser Gln Lys
    2045                2050                2055

Arg Ser Leu His Ser Val Ser Glu Glu Arg Thr Asp Glu Met Thr
    2060                2065                2070

His Lys Glu Thr Asn Glu Gln Glu Glu Arg Leu Leu Ala Thr Ala
    2075                2080                2085

Ser Phe Thr Lys Ser Ser Arg Ser Ser Arg Thr Arg Ser Ser Lys
    2090                2095                2100

Ala Ile Leu Leu Pro Asp Leu Ser Glu Pro Asn Asn Glu Pro Leu
    2105                2110                2115
```

```
Phe Ser Pro Ala Ser Glu Val Pro Arg Lys Ala Lys Ala Lys Lys
2120                2125                2130

Ile Glu Val Pro Ala Gln Leu Lys Glu Leu Val Ser Asp Leu Ser
2135                2140                2145

Ser Gln Phe Val Ile Ser Pro Ala Leu Arg Ser Arg Gln Lys
2150                2155                2160

Asn Thr Ser Asn Lys Asn Lys Leu Glu Asp Glu Leu Lys Asp Asp
2165                2170                2175

Ala Gln Ser Val Glu Thr Leu Gly Lys Pro Lys Ala Lys Arg Ile
2180                2185                2190

Arg Thr Ser Lys Thr Lys Gln Ala Ser Lys Asn Thr Glu Lys Glu
2195                2200                2205

Ser Ala Trp Ser Leu Pro Pro Ile Glu Ile Arg Leu Ile Ser Pro
2210                2215                2220

Leu Ala Ser Pro Ala Asp Gly Val Lys Ser Lys Pro Arg Lys Thr
2225                2230                2235

Thr Glu Val Thr Gly Thr Gly Leu Gly Arg Asn Arg Lys Lys Leu
2240                2245                2250

Ser Ser Tyr Pro Lys Gln Ile Leu Arg Arg Lys Met Leu
2255                2260                2265

<210> SEQ ID NO 15
<211> LENGTH: 7215
<212> TYPE: DNA
<213> ORGANISM: Homo sapiens
<220> FEATURE:
<221> NAME/KEY: CDS
<222> LOCATION: (98)..(6922)

<400> SEQUENCE: 15
tgcggctcga gggggccagc gctgacggtg gcgggtacgg caggctcgcg ggcgccgggc    60
ttcgttacat aatctcggac cggaggagcg gtggcac atg gcg gcg gaa cgg cgc   115
                                        Met Ala Ala Glu Arg Arg
                                         1               5 tgt gga agt atg cga gac tta aga gct caa gtg act agt ggt ctc ctg   163
Cys Gly Ser Met Arg Asp Leu Arg Ala Gln Val Thr Ser Gly Leu Leu
             10                  15                  20 cca ttt cca gaa gtg act ctt caa gcc ctt gga gaa gac gaa ata aca   211
Pro Phe Pro Glu Val Thr Leu Gln Ala Leu Gly Glu Asp Glu Ile Thr
         25                  30                  35 tta gaa tct gtg ctt cgt gga aag ttt gct gcg ggg aaa aat gga ctt   259
Leu Glu Ser Val Leu Arg Gly Lys Phe Ala Ala Gly Lys Asn Gly Leu
 40                  45                  50 gct tgc ttg gct tgt ggt cca caa ctt gag gta gta aac tct ata aca   307
Ala Cys Leu Ala Cys Gly Pro Gln Leu Glu Val Val Asn Ser Ile Thr
 55                  60                  65                  70 gga gag cga ttg tct gct tac aga ttc agt gga gtc aat gaa cag cct   355
Gly Glu Arg Leu Ser Ala Tyr Arg Phe Ser Gly Val Asn Glu Gln Pro
             75                  80                  85 cct gta gtt tta gct gtg aaa gaa ttc tct tgg cag aag aga act gga   403
Pro Val Val Leu Ala Val Lys Glu Phe Ser Trp Gln Lys Arg Thr Gly
         90                  95                 100 tta tta ata gga ttg gaa gaa aca gaa ggg agt gtt ctc tgt ctt tat   451
Leu Leu Ile Gly Leu Glu Glu Thr Glu Gly Ser Val Leu Cys Leu Tyr
    105                 110                 115 gac ctt gga ata tca aaa gta gtt aaa gca gtt gtt ctt cct gga agg   499
Asp Leu Gly Ile Ser Lys Val Val Lys Ala Val Val Leu Pro Gly Arg
120                 125                 130 gta aca gct att gaa cct ata att aat cat gga gga gcc agt gca agc   547
```

```
Val Thr Ala Ile Glu Pro Ile Ile Asn His Gly Gly Ala Ser Ala Ser
135                 140                 145                 150 act cag cat tta cat cca agt ctg cga tgg ctt ttt gga gtg gca gct      595
Thr Gln His Leu His Pro Ser Leu Arg Trp Leu Phe Gly Val Ala Ala
                155                 160                 165 gtg gtc act gat gtt gga cag atc ctt ctt att gac cta tgt ttg gat      643
Val Val Thr Asp Val Gly Gln Ile Leu Leu Ile Asp Leu Cys Leu Asp
                170                 175                 180 gac ttg tca tgc aat caa aat gaa gtt gaa gca tca gat ctt gaa gtt      691
Asp Leu Ser Cys Asn Gln Asn Glu Val Glu Ala Ser Asp Leu Glu Val
                185                 190                 195 cta act ggt atc cca gct gaa gta cca cac att aga gaa agt gtg atg      739
Leu Thr Gly Ile Pro Ala Glu Val Pro His Ile Arg Glu Ser Val Met
        200                 205                 210 aga gaa ggg cgc cat ctg tgt ttc cag tta gta agt cca aca gga aca      787
Arg Glu Gly Arg His Leu Cys Phe Gln Leu Val Ser Pro Thr Gly Thr
215                 220                 225                 230 gcc gtt tca act ctt agt tac ata agc agg aca aat cag ctt gct gca      835
Ala Val Ser Thr Leu Ser Tyr Ile Ser Arg Thr Asn Gln Leu Ala Ala
                235                 240                 245 ggt ttt tct gat ggc tat cta gca ctt tgg aac atg aaa agc atg aaa      883
Gly Phe Ser Asp Gly Tyr Leu Ala Leu Trp Asn Met Lys Ser Met Lys
                250                 255                 260 aga gaa tat tac ata caa ttg gaa agt gga caa gtt cct gta tat gct      931
Arg Glu Tyr Tyr Ile Gln Leu Glu Ser Gly Gln Val Pro Val Tyr Ala
                265                 270                 275 gtc act ttt caa gaa cct gag aat gat cgt cgg aat tgc tgc tac ttg      979
Val Thr Phe Gln Glu Pro Glu Asn Asp Arg Arg Asn Cys Cys Tyr Leu
        280                 285                 290 tgg gct gtt cag tct aca caa gat agt gaa ggg gat gtt ttg agt ttg     1027
Trp Ala Val Gln Ser Thr Gln Asp Ser Glu Gly Asp Val Leu Ser Leu
295                 300                 305                 310 cat ctg ctg cag ctg gcc ttt ggt aat aga aag tgt ttg gca tca gga     1075
His Leu Leu Gln Leu Ala Phe Gly Asn Arg Lys Cys Leu Ala Ser Gly
                315                 320                 325 caa atc tta tat gag ggg tta gaa tac tgt gaa gaa aga tac acc ctg     1123
Gln Ile Leu Tyr Glu Gly Leu Glu Tyr Cys Glu Glu Arg Tyr Thr Leu
                330                 335                 340 gac ctg aca ggt ggc atg ttc cct ttg agg gga cag acg agt aat acc     1171
Asp Leu Thr Gly Gly Met Phe Pro Leu Arg Gly Gln Thr Ser Asn Thr
                345                 350                 355 aaa ttg ttg gga tgc cag agt ata gag aaa ttt cga tct cat ggt gac     1219
Lys Leu Leu Gly Cys Gln Ser Ile Glu Lys Phe Arg Ser His Gly Asp
        360                 365                 370 agg gag gaa ggc gtg aat gaa gct cta tcg cct gac act agt gtt tca     1267
Arg Glu Glu Gly Val Asn Glu Ala Leu Ser Pro Asp Thr Ser Val Ser
375                 380                 385                 390 gtc ttt acc tgg cag gtg aat ata tat gga cag gga aag cct tct gta     1315
Val Phe Thr Trp Gln Val Asn Ile Tyr Gly Gln Gly Lys Pro Ser Val
                395                 400                 405 tat ttg ggg ctt ttt gat ata aat cgt tgg tat cat gca caa atg cca     1363
Tyr Leu Gly Leu Phe Asp Ile Asn Arg Trp Tyr His Ala Gln Met Pro
                410                 415                 420 gat tcg tta agg tca gga gaa tat cta cat aat tgc tct tat ttt gca     1411
Asp Ser Leu Arg Ser Gly Glu Tyr Leu His Asn Cys Ser Tyr Phe Ala
                425                 430                 435 ctg tgg tca ttg gag tct gtt gta agt agg act tct cca cat ggc atc     1459
Leu Trp Ser Leu Glu Ser Val Val Ser Arg Thr Ser Pro His Gly Ile
                440                 445                 450 ttg gat ata tta gta cat gag aga agt tta aat aga gga gtc cct cct     1507
```

```
Leu Asp Ile Leu Val His Glu Arg Ser Leu Asn Arg Gly Val Pro Pro
455                 460                 465                 470 tca tat cca cct ccc gag cag ttt ttt aat cca agc act tat aat ttt        1555
Ser Tyr Pro Pro Pro Glu Gln Phe Phe Asn Pro Ser Thr Tyr Asn Phe
                475                 480                 485 gat gcc act tgt ttg tta aac tcg gga gtt gtt cat tta act tgt act        1603
Asp Ala Thr Cys Leu Leu Asn Ser Gly Val Val His Leu Thr Cys Thr
                490                 495                 500 ggc ttt cag aag gag act ttg act ttt tta aag aaa tca ggt cca tca        1651
Gly Phe Gln Lys Glu Thr Leu Thr Phe Leu Lys Lys Ser Gly Pro Ser
                505                 510                 515 ctc aat gaa ctc att cct gat ggt tat aat cga tgt ctt gta gct ggc        1699
Leu Asn Glu Leu Ile Pro Asp Gly Tyr Asn Arg Cys Leu Val Ala Gly
            520                 525                 530 ctt ctt tcc cca aga ttt gtt gat gtt cag cct tcc agt tta agc caa        1747
Leu Leu Ser Pro Arg Phe Val Asp Val Gln Pro Ser Ser Leu Ser Gln
535                 540                 545                 550 gaa gaa cag tta gaa gct ata ttg tca gca gca att cag act agt tcc        1795
Glu Glu Gln Leu Glu Ala Ile Leu Ser Ala Ala Ile Gln Thr Ser Ser
                555                 560                 565 ctg gga ctt ttg act ggt tat atc cga aga tgg ata aca gaa gaa caa        1843
Leu Gly Leu Leu Thr Gly Tyr Ile Arg Arg Trp Ile Thr Glu Glu Gln
            570                 575                 580 cca aat tct gcc act aat ttg cgc ttt gtt ctt gaa tgg acg tgg aat        1891
Pro Asn Ser Ala Thr Asn Leu Arg Phe Val Leu Glu Trp Thr Trp Asn
            585                 590                 595 aaa gtg gtt ctc aca aaa gag gaa ttt gac aga cta tgt gtg cca tta        1939
Lys Val Val Leu Thr Lys Glu Glu Phe Asp Arg Leu Cys Val Pro Leu
600                 605                 610 ttt gat ggt tcg tgt cat ttc atg gat cca caa act ata cag tct atc        1987
Phe Asp Gly Ser Cys His Phe Met Asp Pro Gln Thr Ile Gln Ser Ile
615                 620                 625                 630 cag caa tgc tat ttg ctt ctt agc aat ctt aat ata gtc ttg agc tgt        2035
Gln Gln Cys Tyr Leu Leu Leu Ser Asn Leu Asn Ile Val Leu Ser Cys
                635                 640                 645 ttt gca tca gaa gcc cga gag atc gct gag aga gga ctg ata gac tta        2083
Phe Ala Ser Glu Ala Arg Glu Ile Ala Glu Arg Gly Leu Ile Asp Leu
                650                 655                 660 agc aat aag ttt gtg gtt tcc cac ctc atc tgt cag tat gca caa gtg        2131
Ser Asn Lys Phe Val Val Ser His Leu Ile Cys Gln Tyr Ala Gln Val
            665                 670                 675 gtt ctt tgg ttc tct cat tct ggg ctt tta cca gaa ggc ata gat gat        2179
Val Leu Trp Phe Ser His Ser Gly Leu Leu Pro Glu Gly Ile Asp Asp
            680                 685                 690 tct gtg cag ttg tca agg tta tgc tac aac tac cct gta att cag aac        2227
Ser Val Gln Leu Ser Arg Leu Cys Tyr Asn Tyr Pro Val Ile Gln Asn
695                 700                 705                 710 tac tac acc agt cgt cga cag aag ttt gag cgt tta tca aga ggg aag        2275
Tyr Tyr Thr Ser Arg Arg Gln Lys Phe Glu Arg Leu Ser Arg Gly Lys
                715                 720                 725 tgg aat ccc gat tgc ttg atg att gat gga ctg gtt tct cag tta gga        2323
Trp Asn Pro Asp Cys Leu Met Ile Asp Gly Leu Val Ser Gln Leu Gly
                730                 735                 740 gag cga att gag aag ttg tgg aaa cga gat gaa gga ggc aca gga aaa        2371
Glu Arg Ile Glu Lys Leu Trp Lys Arg Asp Glu Gly Gly Thr Gly Lys
            745                 750                 755 tat cct cct gct agt ctg cat gca gta ctt gat atg tac cta tta gac        2419
Tyr Pro Pro Ala Ser Leu His Ala Val Leu Asp Met Tyr Leu Leu Asp
            760                 765                 770 ggc gtt act gaa gca gcc aaa cac tct att acc att tat ttg cta ctt        2467
```

-continued

| | | |
|---|---|---|
| Gly Val Thr Glu Ala Ala Lys His Ser Ile Thr Ile Tyr Leu Leu Leu<br>775                          780                        785                         790 | |

```
gat att atg tat tcc ttt ccc aac aaa aca gac act ccc att gaa tct     2515
Asp Ile Met Tyr Ser Phe Pro Asn Lys Thr Asp Thr Pro Ile Glu Ser
                    795                 800                 805 ttc cca act gta ttt gcc att tct tgg ggc caa gtt aaa ctt att cag     2563
Phe Pro Thr Val Phe Ala Ile Ser Trp Gly Gln Val Lys Leu Ile Gln
                810                 815                 820 ggg ttt tgg ttg ata gat cat aat gac tat gag agt ggt ttg gat ctt     2611
Gly Phe Trp Leu Ile Asp His Asn Asp Tyr Glu Ser Gly Leu Asp Leu
            825                 830                 835 ttg ttt cat cca gct act gca aaa cct ttg tca tgg caa cat tca aag     2659
Leu Phe His Pro Ala Thr Ala Lys Pro Leu Ser Trp Gln His Ser Lys
        840                 845                 850 att att cag gca ttc atg agt cag ggc gag cac aga caa gcc ctc aga     2707
Ile Ile Gln Ala Phe Met Ser Gln Gly Glu His Arg Gln Ala Leu Arg
    855                 860                 865                 870 tat att cag aca atg aag cca aca gtg tcc agt ggt aac gat gtt atc     2755
Tyr Ile Gln Thr Met Lys Pro Thr Val Ser Ser Gly Asn Asp Val Ile
                875                 880                 885 ctt cac ctc act gtt ttg ctt ttt aat agg tgt atg gtt gaa gcc tgg     2803
Leu His Leu Thr Val Leu Leu Phe Asn Arg Cys Met Val Glu Ala Trp
            890                 895                 900 aat ttt ttg cgg caa cat tgc aat agg ttg aat ata gag gag tta ctg     2851
Asn Phe Leu Arg Gln His Cys Asn Arg Leu Asn Ile Glu Glu Leu Leu
        905                 910                 915 aag cac atg tat gaa gtc tgt cag gaa atg ggc ttg atg gaa gat tta     2899
Lys His Met Tyr Glu Val Cys Gln Glu Met Gly Leu Met Glu Asp Leu
    920                 925                 930 ctg aag tta cca ttt aca gac act gag cag gaa tgt tta gtg aaa ttt     2947
Leu Lys Leu Pro Phe Thr Asp Thr Glu Gln Glu Cys Leu Val Lys Phe
935                 940                 945                 950 ttg cag tcc agt gcc agc gtt cag aat cat gaa ttc ctt tta gtg cac     2995
Leu Gln Ser Ser Ala Ser Val Gln Asn His Glu Phe Leu Leu Val His
                955                 960                 965 cat ttg cag cgt gcc aat tat gtg cct gcc ttg aag ctg aac caa act     3043
His Leu Gln Arg Ala Asn Tyr Val Pro Ala Leu Lys Leu Asn Gln Thr
            970                 975                 980 ctg aag att aat gtt atg aat gat cgt gat cct cgt ttg cgg gag aga     3091
Leu Lys Ile Asn Val Met Asn Asp Arg Asp Pro Arg Leu Arg Glu Arg
        985                 990                 995 tca ctg gct cga aat tct ata  tta gac cag tat gga  aaa atc ctt       3136
Ser Leu Ala Arg Asn Ser Ile Leu Asp Gln Tyr Gly Lys Ile Leu
    1000                1005                    1010 cct aga gtc cat cga aaa tta  gcc att gaa cga gct  aag cct tat       3181
Pro Arg Val His Arg Lys Leu Ala Ile Glu Arg Ala Lys Pro Tyr
1015                    1020                    1025 cat ctg tca aca tca tca gtt  ttt cga tta gtt tct  aga ccc aaa       3226
His Leu Ser Thr Ser Ser Val Phe Arg Leu Val Ser Arg Pro Lys
    1030                1035                    1040 cca tta tca gca gtt cca aag  caa gtt gta aca gga  act gtg ttg       3271
Pro Leu Ser Ala Val Pro Lys Gln Val Val Thr Gly Thr Val Leu
    1045                1050                    1055 aca aga tct gtt ttc atc aac  aat gtt tta tct aaa  att gga gaa       3316
Thr Arg Ser Val Phe Ile Asn Asn Val Leu Ser Lys Ile Gly Glu
    1060                1065                    1070 gtt tgg gca agc aaa gaa cct  ata aat agc acc aca  cct ttc aat       3361
Val Trp Ala Ser Lys Glu Pro Ile Asn Ser Thr Thr Pro Phe Asn
    1075                1080                    1085 agt tct aaa ata gaa gaa cca  tct cct ata gtg tat  tcg ctc cca       3406
```

```
Ser Ser Lys Ile Glu Glu Pro Ser Pro Ile Val Tyr Ser Leu Pro
    1090            1095                1100 gct cca gag ctg cct gag gca ttt ttt gga aca cca att tca aaa       3451
Ala Pro Glu Leu Pro Glu Ala Phe Phe Gly Thr Pro Ile Ser Lys
1105            1110                1115 gca tca caa aaa att tct aga ctg cta gat ttg gtt gtt cag cct       3496
Ala Ser Gln Lys Ile Ser Arg Leu Leu Asp Leu Val Val Gln Pro
    1120            1125                1130 gtc ccc cgg cct tct cag tgt tcg gag ttt att cag caa agc tcc       3541
Val Pro Arg Pro Ser Gln Cys Ser Glu Phe Ile Gln Gln Ser Ser
1135            1140                1145 atg aaa tct cct ttg tac cta gta tcc cgt tca ctg ccc tca agt       3586
Met Lys Ser Pro Leu Tyr Leu Val Ser Arg Ser Leu Pro Ser Ser
    1150            1155                1160 tcg caa tta aaa gga tcg cct cag gcc atc tcc agg gct tca gaa       3631
Ser Gln Leu Lys Gly Ser Pro Gln Ala Ile Ser Arg Ala Ser Glu
1165            1170                1175 tta cat ttg ctt gaa act cct ctt gta gtt aag aaa gct aaa agt       3676
Leu His Leu Leu Glu Thr Pro Leu Val Val Lys Lys Ala Lys Ser
    1180            1185                1190 ttg gcc atg tca gtt act act tct gga ttt tct gag ttc act cct       3721
Leu Ala Met Ser Val Thr Thr Ser Gly Phe Ser Glu Phe Thr Pro
1195            1200                1205 cag tcc atc ctg agg tct act cct cga tca aca cct tta gca tct       3766
Gln Ser Ile Leu Arg Ser Thr Pro Arg Ser Thr Pro Leu Ala Ser
    1210            1215                1220 ccc tct cca tca cct gga agg tct cct caa cga ctt aaa gaa act       3811
Pro Ser Pro Ser Pro Gly Arg Ser Pro Gln Arg Leu Lys Glu Thr
1225            1230                1235 aga att tca ttt gtg gaa gaa gat gtc cac cca aaa tgg att cct       3856
Arg Ile Ser Phe Val Glu Glu Asp Val His Pro Lys Trp Ile Pro
    1240            1245                1250 ggg gct gca gat gat agc aaa tta gaa gta ttt act aca cct aaa       3901
Gly Ala Ala Asp Asp Ser Lys Leu Glu Val Phe Thr Thr Pro Lys
1255            1260                1265 aaa tgt gca gtt cca gtg gaa act gaa tgg ccg aag agc aaa gat       3946
Lys Cys Ala Val Pro Val Glu Thr Glu Trp Pro Lys Ser Lys Asp
    1270            1275                1280 agg acc aca tct ttt ttc ctg aac agc cct gaa aag gag cat caa       3991
Arg Thr Thr Ser Phe Phe Leu Asn Ser Pro Glu Lys Glu His Gln
1285            1290                1295 gaa atg gat gag ggg tca caa agt tta gag aaa ctg gat gtg agc       4036
Glu Met Asp Glu Gly Ser Gln Ser Leu Glu Lys Leu Asp Val Ser
    1300            1305                1310 aaa gga aac agc agt gtt tca atc aca tcc gat gag act acc tta       4081
Lys Gly Asn Ser Ser Val Ser Ile Thr Ser Asp Glu Thr Thr Leu
1315            1320                1325 gag tat cag gat gca ccg tcc ccg gaa gac ctt gaa gag act gtt       4126
Glu Tyr Gln Asp Ala Pro Ser Pro Glu Asp Leu Glu Glu Thr Val
    1330            1335                1340 ttc acg gcc tct aag ccc aaa agc tct tcc act gca cta act act       4171
Phe Thr Ala Ser Lys Pro Lys Ser Ser Ser Thr Ala Leu Thr Thr
1345            1350                1355 aat gta act gaa caa act gaa aag gat gga gat aaa gat gta ttt       4216
Asn Val Thr Glu Gln Thr Glu Lys Asp Gly Asp Lys Asp Val Phe
    1360            1365                1370 gca tca gaa gta act cct tca gac cta cag aaa caa atg ggc aat       4261
Ala Ser Glu Val Thr Pro Ser Asp Leu Gln Lys Gln Met Gly Asn
1375            1380                1385 tta gaa gat gca gaa aca aag gat ctc tta gtt gca gca gag gca       4306
```

```
                     Leu Glu Asp Ala Glu Thr Lys Asp Leu Leu Val Ala Ala Glu Ala
                         1390                1395                1400 ttt tca gaa ttg aat cac tta agc ccg gtt caa gga act gaa gct           4351
Phe Ser Glu Leu Asn His Leu Ser Pro Val Gln Gly Thr Glu Ala
    1405                1410                1415 tct ctt tgt gca cca tca gtc tat gaa ggg aaa atc ttc acc cag           4396
Ser Leu Cys Ala Pro Ser Val Tyr Glu Gly Lys Ile Phe Thr Gln
    1420                1425                1430 aag tcc aag gta cca gtg ttg gac gaa gga tta aca tct gtt gaa           4441
Lys Ser Lys Val Pro Val Leu Asp Glu Gly Leu Thr Ser Val Glu
    1435                1440                1445 acc tac acc cct gca att aga gca aat gac aat aaa tct atg gct           4486
Thr Tyr Thr Pro Ala Ile Arg Ala Asn Asp Asn Lys Ser Met Ala
    1450                1455                1460 gat gtc ctt ggt gat ggt gga aac tcc tcg ctc act atc tct gaa           4531
Asp Val Leu Gly Asp Gly Gly Asn Ser Ser Leu Thr Ile Ser Glu
    1465                1470                1475 ggt cct att gtc tct gag cgc agg ctt aac cag gaa gta gcg ctg           4576
Gly Pro Ile Val Ser Glu Arg Arg Leu Asn Gln Glu Val Ala Leu
    1480                1485                1490 aac tta aaa gaa gat cat gaa gta gaa gtt ggt gta cta aaa gaa           4621
Asn Leu Lys Glu Asp His Glu Val Glu Val Gly Val Leu Lys Glu
    1495                1500                1505 agt gtt gac tta cca gaa gaa aag ctt cca att tct gac agc cct           4666
Ser Val Asp Leu Pro Glu Glu Lys Leu Pro Ile Ser Asp Ser Pro
    1510                1515                1520 cct gat act caa gaa att cat gtg att gaa caa gaa aag ctt gaa           4711
Pro Asp Thr Gln Glu Ile His Val Ile Glu Gln Glu Lys Leu Glu
    1525                1530                1535 gct caa gat tca gga gaa gag gct agg aat ctt tca ttt aat gag           4756
Ala Gln Asp Ser Gly Glu Glu Ala Arg Asn Leu Ser Phe Asn Glu
    1540                1545                1550 tta tat ccc tct gga aca ctt aag ctt cag tac aat ttt gat act           4801
Leu Tyr Pro Ser Gly Thr Leu Lys Leu Gln Tyr Asn Phe Asp Thr
    1555                1560                1565 att gac caa cag ttt tgt gac tta gct gat aac aaa gac act gct           4846
Ile Asp Gln Gln Phe Cys Asp Leu Ala Asp Asn Lys Asp Thr Ala
    1570                1575                1580 gaa tgt gac att gct gaa gta gat ggg gaa ctt ttt gtg gct caa           4891
Glu Cys Asp Ile Ala Glu Val Asp Gly Glu Leu Phe Val Ala Gln
    1585                1590                1595 agc aac ttt acc ttg ata ttg gaa ggt gaa gaa gga gaa gtt gag           4936
Ser Asn Phe Thr Leu Ile Leu Glu Gly Glu Glu Gly Glu Val Glu
    1600                1605                1610 cca ggt gat ttt gca tca tct gat gtg tta cct aaa gca gct aac           4981
Pro Gly Asp Phe Ala Ser Ser Asp Val Leu Pro Lys Ala Ala Asn
    1615                1620                1625 aca gca act gaa gaa aaa ctt gta tgc agt ggg gaa aat gat aat           5026
Thr Ala Thr Glu Glu Lys Leu Val Cys Ser Gly Glu Asn Asp Asn
    1630                1635                1640 cat gga caa att gca aat ttg cca tct gcc gta act agt gac caa           5071
His Gly Gln Ile Ala Asn Leu Pro Ser Ala Val Thr Ser Asp Gln
    1645                1650                1655 aag tcc caa aaa gta gac act tta cca tat gtg cct gaa cct att           5116
Lys Ser Gln Lys Val Asp Thr Leu Pro Tyr Val Pro Glu Pro Ile
    1660                1665                1670 aaa gta gca att gca gaa aat tta cta gat gta att aaa gac aca           5161
Lys Val Ala Ile Ala Glu Asn Leu Leu Asp Val Ile Lys Asp Thr
    1675                1680                1685 aga agt aaa gaa att act tca gat aca atg gaa cag tcc att cat           5206
```

|     |     |     |     |     |     |     |     |     |     |     |     |     |
|---|---|---|---|---|---|---|---|---|---|---|---|---|
| Arg | Ser | Lys | Glu | Ile | Thr | Ser | Asp | Thr | Met | Glu | Gln | Ser Ile His |
|     | 1690 |     |     |     | 1695 |     |     |     | 1700 |     |     |     |

| gaa | aca | ata | cct | tta | gtg | agc | caa | aac | ata | atg | tgt | ccc | act | aaa | 5251 |
|---|---|---|---|---|---|---|---|---|---|---|---|---|---|---|---|
| Glu | Thr | Ile | Pro | Leu | Val | Ser | Gln | Asn | Ile | Met | Cys | Pro | Thr | Lys |  |
|  | 1705 |  |  |  | 1710 |  |  |  | 1715 |  |  |  |  |  |  |

| ttg | gtc | aaa | tct | gca | ttt | aag | act | gct | cag | gaa | aca | agc | aca | atg | 5296 |
|---|---|---|---|---|---|---|---|---|---|---|---|---|---|---|---|
| Leu | Val | Lys | Ser | Ala | Phe | Lys | Thr | Ala | Gln | Glu | Thr | Ser | Thr | Met |  |
|  | 1720 |  |  |  | 1725 |  |  |  | 1730 |  |  |  |  |  |  |

| act | atg | aat | gtc | agc | cag | gtt | gat | gac | gtg | gtt | tcc | tcc | aaa | act | 5341 |
|---|---|---|---|---|---|---|---|---|---|---|---|---|---|---|---|
| Thr | Met | Asn | Val | Ser | Gln | Val | Asp | Asp | Val | Val | Ser | Ser | Lys | Thr |  |
|  | 1735 |  |  |  | 1740 |  |  |  | 1745 |  |  |  |  |  |  |

| cgt | acg | aga | ggt | caa | cgt | atc | caa | aac | gtg | aat | gtc | aaa | tca | gca | 5386 |
|---|---|---|---|---|---|---|---|---|---|---|---|---|---|---|---|
| Arg | Thr | Arg | Gly | Gln | Arg | Ile | Gln | Asn | Val | Asn | Val | Lys | Ser | Ala |  |
|  | 1750 |  |  |  | 1755 |  |  |  | 1760 |  |  |  |  |  |  |

| caa | cag | gaa | gca | tca | gca | gat | gtt | gct | act | cct | aag | atg | cca | ggg | 5431 |
|---|---|---|---|---|---|---|---|---|---|---|---|---|---|---|---|
| Gln | Gln | Glu | Ala | Ser | Ala | Asp | Val | Ala | Thr | Pro | Lys | Met | Pro | Gly |  |
|  | 1765 |  |  |  | 1770 |  |  |  | 1775 |  |  |  |  |  |  |

| cag | tca | gtc | agg | aag | aaa | act | agg | aag | gca | aaa | gaa | att | tct | gaa | 5476 |
|---|---|---|---|---|---|---|---|---|---|---|---|---|---|---|---|
| Gln | Ser | Val | Arg | Lys | Lys | Thr | Arg | Lys | Ala | Lys | Glu | Ile | Ser | Glu |  |
|  | 1780 |  |  |  | 1785 |  |  |  | 1790 |  |  |  |  |  |  |

| gct | tct | gaa | aac | atc | tat | tct | gat | gtc | aga | gga | cta | ttt | cag | aac | 5521 |
|---|---|---|---|---|---|---|---|---|---|---|---|---|---|---|---|
| Ala | Ser | Glu | Asn | Ile | Tyr | Ser | Asp | Val | Arg | Gly | Leu | Phe | Gln | Asn |  |
|  | 1795 |  |  |  | 1800 |  |  |  | 1805 |  |  |  |  |  |  |

| cag | caa | ata | cct | caa | aat | tct | gtt | acg | cct | agg | aga | gga | agg | aga | 5566 |
|---|---|---|---|---|---|---|---|---|---|---|---|---|---|---|---|
| Gln | Gln | Ile | Pro | Gln | Asn | Ser | Val | Thr | Pro | Arg | Arg | Gly | Arg | Arg |  |
|  | 1810 |  |  |  | 1815 |  |  |  | 1820 |  |  |  |  |  |  |

| aag | aaa | gaa | gtt | aat | cag | gac | ata | cta | gaa | aac | acc | agt | tct | gtg | 5611 |
|---|---|---|---|---|---|---|---|---|---|---|---|---|---|---|---|
| Lys | Lys | Glu | Val | Asn | Gln | Asp | Ile | Leu | Glu | Asn | Thr | Ser | Ser | Val |  |
|  | 1825 |  |  |  | 1830 |  |  |  | 1835 |  |  |  |  |  |  |

| gaa | caa | gaa | tta | cag | atc | act | aca | ggt | agg | gaa | tca | aaa | aga | tta | 5656 |
|---|---|---|---|---|---|---|---|---|---|---|---|---|---|---|---|
| Glu | Gln | Glu | Leu | Gln | Ile | Thr | Thr | Gly | Arg | Glu | Ser | Lys | Arg | Leu |  |
|  | 1840 |  |  |  | 1845 |  |  |  | 1850 |  |  |  |  |  |  |

| aaa | tca | tct | cag | ctg | ttg | gaa | cca | gca | gtt | gaa | gaa | act | act | aaa | 5701 |
|---|---|---|---|---|---|---|---|---|---|---|---|---|---|---|---|
| Lys | Ser | Ser | Gln | Leu | Leu | Glu | Pro | Ala | Val | Glu | Glu | Thr | Thr | Lys |  |
|  | 1855 |  |  |  | 1860 |  |  |  | 1865 |  |  |  |  |  |  |

| aaa | gaa | gtt | aag | gtt | tca | tct | gtt | aca | aaa | agg | act | cct | aga | aga | 5746 |
|---|---|---|---|---|---|---|---|---|---|---|---|---|---|---|---|
| Lys | Glu | Val | Lys | Val | Ser | Ser | Val | Thr | Lys | Arg | Thr | Pro | Arg | Arg |  |
|  | 1870 |  |  |  | 1875 |  |  |  | 1880 |  |  |  |  |  |  |

| att | aaa | aga | tct | gta | gaa | aat | cag | gaa | agt | gtt | gaa | att | ata | aat | 5791 |
|---|---|---|---|---|---|---|---|---|---|---|---|---|---|---|---|
| Ile | Lys | Arg | Ser | Val | Glu | Asn | Gln | Glu | Ser | Val | Glu | Ile | Ile | Asn |  |
|  | 1885 |  |  |  | 1890 |  |  |  | 1895 |  |  |  |  |  |  |

| gat | cta | aaa | gtt | agt | acg | gta | aca | agt | cct | agc | aga | atg | atc | aga | 5836 |
|---|---|---|---|---|---|---|---|---|---|---|---|---|---|---|---|
| Asp | Leu | Lys | Val | Ser | Thr | Val | Thr | Ser | Pro | Ser | Arg | Met | Ile | Arg |  |
|  | 1900 |  |  |  | 1905 |  |  |  | 1910 |  |  |  |  |  |  |

| aaa | ttg | aga | agt | act | aat | tta | gat | gct | tct | gaa | aat | aca | gga | aat | 5881 |
|---|---|---|---|---|---|---|---|---|---|---|---|---|---|---|---|
| Lys | Leu | Arg | Ser | Thr | Asn | Leu | Asp | Ala | Ser | Glu | Asn | Thr | Gly | Asn |  |
|  | 1915 |  |  |  | 1920 |  |  |  | 1925 |  |  |  |  |  |  |

| aag | caa | gat | gat | aaa | tcc | agt | gac | aag | cag | ctg | cgt | att | aaa | cat | 5926 |
|---|---|---|---|---|---|---|---|---|---|---|---|---|---|---|---|
| Lys | Gln | Asp | Asp | Lys | Ser | Ser | Asp | Lys | Gln | Leu | Arg | Ile | Lys | His |  |
|  | 1930 |  |  |  | 1935 |  |  |  | 1940 |  |  |  |  |  |  |

| gtt | aga | agg | gtc | aga | ggg | aga | gaa | gtt | agt | cca | tca | gat | gtg | aga | 5971 |
|---|---|---|---|---|---|---|---|---|---|---|---|---|---|---|---|
| Val | Arg | Arg | Val | Arg | Gly | Arg | Glu | Val | Ser | Pro | Ser | Asp | Val | Arg |  |
|  | 1945 |  |  |  | 1950 |  |  |  | 1955 |  |  |  |  |  |  |

| gaa | gac | tcc | aac | ctt | gag | tca | tct | cag | ttg | act | gtt | caa | gca | gaa | 6016 |
|---|---|---|---|---|---|---|---|---|---|---|---|---|---|---|---|
| Glu | Asp | Ser | Asn | Leu | Glu | Ser | Ser | Gln | Leu | Thr | Val | Gln | Ala | Glu |  |
|  | 1960 |  |  |  | 1965 |  |  |  | 1970 |  |  |  |  |  |  |

| ttt | gat | atg | tct | gcc | ata | cct | aga | aaa | cgt | ggt | aga | cca | aga | aaa | 6061 |
|---|---|---|---|---|---|---|---|---|---|---|---|---|---|---|---|
| Phe | Asp | Met | Ser | Ala | Ile | Pro | Arg | Lys | Arg | Gly | Arg | Pro | Arg | Lys |  |
|  | 1975 |  |  |  | 1980 |  |  |  | 1985 |  |  |  |  |  |  |

| atc | aat | cca | tct | gaa | gat | gta | gga | tct | aag | gct | gtt | aag | gaa | gag | 6106 |
|---|---|---|---|---|---|---|---|---|---|---|---|---|---|---|---|

-continued

| | | |
|---|---|---|
| Ile Asn Pro Ser Glu Asp Val Gly Ser Lys Ala Val Lys Glu Glu<br>    1990                1995                2000 | | |
| aga agc ccc aag aag aaa gaa gct ccc agc att aga agg aga tct<br>Arg Ser Pro Lys Lys Lys Glu Ala Pro Ser Ile Arg Arg Arg Ser<br>    2005                2010                2015 | | 6151 |
| aca aga aat acc cca gct aaa agt gaa aat gtt gat gtt gga aaa<br>Thr Arg Asn Thr Pro Ala Lys Ser Glu Asn Val Asp Val Gly Lys<br>    2020                2025                2030 | | 6196 |
| cca gct tta gga aaa tcc att tta gtg cca aac gag gaa ctt tcg<br>Pro Ala Leu Gly Lys Ser Ile Leu Val Pro Asn Glu Glu Leu Ser<br>    2035                2040                2045 | | 6241 |
| atg gtg atg agc tct aag aaa aaa ctt aca aaa aag act gaa agt<br>Met Val Met Ser Ser Lys Lys Lys Leu Thr Lys Lys Thr Glu Ser<br>    2050                2055                2060 | | 6286 |
| caa agc caa aaa cgt tca ttg cac tca gta tca gaa gaa cgc aca<br>Gln Ser Gln Lys Arg Ser Leu His Ser Val Ser Glu Glu Arg Thr<br>    2065                2070                2075 | | 6331 |
| gat gaa atg aca cat aaa gaa aca aat gag cag gaa gaa aga ttg<br>Asp Glu Met Thr His Lys Glu Thr Asn Glu Gln Glu Glu Arg Leu<br>    2080                2085                2090 | | 6376 |
| ctc gcc aca gct tcc ttc act aaa tca tcc cgc agc agc agg act<br>Leu Ala Thr Ala Ser Phe Thr Lys Ser Ser Arg Ser Ser Arg Thr<br>    2095                2100                2105 | | 6421 |
| cgg tct agc aag gcc atc ttg ttg ccg gac ctt tct gaa cca aac<br>Arg Ser Ser Lys Ala Ile Leu Leu Pro Asp Leu Ser Glu Pro Asn<br>    2110                2115                2120 | | 6466 |
| aat gag cct tta ttt tct cca gcg tca gaa gtt cca agg aaa gca<br>Asn Glu Pro Leu Phe Ser Pro Ala Ser Glu Val Pro Arg Lys Ala<br>    2125                2130                2135 | | 6511 |
| aaa gct aaa aaa ata gag gtt cct gca cag ctg aaa gaa tta gtt<br>Lys Ala Lys Lys Ile Glu Val Pro Ala Gln Leu Lys Glu Leu Val<br>    2140                2145                2150 | | 6556 |
| tcg gat tta tct tct cag ttt gtc atc tca cct cct gct tta agg<br>Ser Asp Leu Ser Ser Gln Phe Val Ile Ser Pro Pro Ala Leu Arg<br>    2155                2160                2165 | | 6601 |
| agc aga caa aaa aac aca tcc aat aag aac aag ctt gaa gat gaa<br>Ser Arg Gln Lys Asn Thr Ser Asn Lys Asn Lys Leu Glu Asp Glu<br>    2170                2175                2180 | | 6646 |
| ctg aaa gat gat gca caa tca gta gaa act ctg gga aag cca aaa<br>Leu Lys Asp Asp Ala Gln Ser Val Glu Thr Leu Gly Lys Pro Lys<br>    2185                2190                2195 | | 6691 |
| gcg aaa cga atc agg acg tca aaa aca aaa caa gca agc aaa aac<br>Ala Lys Arg Ile Arg Thr Ser Lys Thr Lys Gln Ala Ser Lys Asn<br>    2200                2205                2210 | | 6736 |
| aca gaa aaa gaa agt gct tgg tca ctt cct ccc ata gaa att cgg<br>Thr Glu Lys Glu Ser Ala Trp Ser Leu Pro Pro Ile Glu Ile Arg<br>    2215                2220                2225 | | 6781 |
| ctg att tcc ccc ttg gct agc cca gct gac gga gtc aag agc aaa<br>Leu Ile Ser Pro Leu Ala Ser Pro Ala Asp Gly Val Lys Ser Lys<br>    2230                2235                2240 | | 6826 |
| cca aga aaa act aca gaa gtg aca gga aca ggt ctt gga agg aac<br>Pro Arg Lys Thr Thr Glu Val Thr Gly Thr Gly Leu Gly Arg Asn<br>    2245                2250                2255 | | 6871 |
| aga aag aaa ctg tct tcc tat cca aag caa att tta cgc aga aaa<br>Arg Lys Lys Leu Ser Ser Tyr Pro Lys Gln Ile Leu Arg Arg Lys<br>    2260                2265                2270 | | 6916 |
| atg ctg taatttcttg ggaagatttt aatgtacacc tatttgtaaa gtcatcagaa<br>Met Leu<br>    2275 | | 6972 |
| tagtgtggat tattaaatat ctagtttgga agaaaataat ttatataaat tattgtaaat | | 7032 |

```
ttttatgtaa acagaaggtc ttcaataagt aaagtaactc catatggagt gattgtttca    7092
gtccaggcaa tttttctatt ttatattaag acttcataca tttatatatg taaatatggc    7152
ttattaatgg aatgttaaat aaaatgtata cttctcaaaa aaaaaaaaaa aaaaaaaaaa    7212
aaa                                                                  7215
```

<210> SEQ ID NO 16
<211> LENGTH: 9
<212> TYPE: PRT
<213> ORGANISM: Artificial Sequence
<220> FEATURE:
<223> OTHER INFORMATION: Syntheticaly generated peptide

<400> SEQUENCE: 16

Met Ala Ala Glu Arg Arg Cys Gly Ser
1               5

YS68 POLYPEPTIDE INVOLVED IN PRIMITIVE HEMATOPOIESIS

This application is a divisional of U.S. patent application Ser. No. 11/643,069, filed Dec. 20, 2006, which is a continuation of U.S. patent application Ser. No. 10/118,513, filed Apr. 8, 2002 which is a continuation-in-part of International Patent Application PCT/JP00/05756, filed Aug. 25, 2000, which claims priority to Japanese patent application Ser. Nos. 11/288,738, filed Oct. 8, 1999; 11/288,739, filed Oct. 8, 1999; and 2000-123721, filed Apr. 19, 2000. The contents of these prior applications are incorporated by reference herein.

TECHNICAL FIELD

The present invention relates to novel proteins involved in primitive hematopoiesis and genes encoding the proteins. These molecules may be utilized, for example, in the field of drug development.

BACKGROUND

There are two kinds of hematopoiesis: one is the transient primitive hematopoiesis (embryonic hematopoiesis) that functions only during the embryonic stage, and the other is the definitive hematopoiesis (adult hematopoiesis) that contributes to lifelong hematopoiesis. Research by Medvinsky et al. (Medvinsky et al., Cell 86:897-906, 1996; Cumano et al., Cell 86:907-916) revealed that, in contrast to primitive hematopoiesis that develops within the yolk sac on around embryonic day 9, definitive hematopoiesis is initiated within the AGM (Aorta-Gonad-Mesonephros) region on around embryonic day 10. Furthermore, regarding the origin of hematocytes, various studies have suggested that definitive hematopoiesis originates from hemangioblasts, thought to be precursor cells common to hematopoietic cells and vascular endothelium cells.

While the mainly accepted view was that hemangioblasts, which are the origin of definitive hematopoiesis, exist in the AGM region, Yorder et al. argued against the existing theory and demonstrated that hemangioblasts, which may contribute to definitive hematopoiesis, also exist in the yolk sac (Yoder et al., Immunity 7:335-344, 1997). Therefore, it is now generally accepted that the surrounding environment is important for the differentiation of hemangioblasts to hematopoietic cells.

Thus, while the origin of hematopoietic cells and the site of development have been gradually elucidated by phenomenological research, the molecular mechanism of hematopoietic development remains unclear. The isolation of a novel molecule involved with primitive hematopoiesis is thought to be an important step for the development of unprecedented drugs associated with hematological disorders.

SUMMARY

The subject of the present invention is to provide novel proteins involved in primitive hematopoiesis and genes encoding the proteins, as well as production and use of the same.

Although the existence of hemangioblasts has been reported in the mouse AGM (Aorta-Gonad-Mesonephros) region on embryonic day 9 to day 12, Yorder and Nishikawa et al. have reported that hemangioblasts exist in embryonic day 9 yolk sacs, but no longer exist in embryonic day 13 yolk sacs (Yoder et al., Immunity 7:335-344, 1997; Nishikawa et al., Immunity 8:761-769, 1998). The present inventors conducted cloning of genes to identify molecules involved with primitive hematopoiesis by subtracting the cDNA derived from embryonic day 13 mouse yolk sac in which hemangioblasts are assumed to be absent, from the cDNA derived from embryonic day 9 mouse yolk sac in which hemangioblast is suggested to be present. Inventors succeeded in isolating a novel gene that was named "YS68". In addition, a primer was constructed based on the nucleotide sequence of the mouse gene, and, by performing 5'-RACE and 3'-RACE using human fetal liver Marathon-Ready cDNA as a template, the corresponding human gene was successfully isolated.

Determination and comparison of the full-length human (SEQ ID NO: 13) and mouse (SEQ ID NO: 11) cDNA sequences showed a very high sequence homology of 87% in the N-terminal region (human 1-1137 of SEQ ID NO: 13, mouse 1-1137 of SEQ ID NO: 11); whereas the homology in the central region (human 1138-1683 of SEQ ID NO: 13, mouse 1138-1679 of SEQ ID NO: 11) was 57%; and the homology in the C-terminal region (human 1684-2266 of SEQ ID NO: 13, mouse 1680-2243 of SEQ ID NO: 11) was very low at 45%. Many nuclear transport signals were found to exist in the low-homology C-terminal region. On the other hand, two WD repeats that are known to be necessary for interaction with proteins were found to exist in the high-homology N-terminal region.

To investigate the role of "YS68" in hematopoiesis, RT-PCR analysis of the expression pattern of "YS68" in mouse hematopoietic tissue was performed; the results revealed that the expression pattern of "YS68" correlated with the transport of hematopoietic tissues during the embryonic stage. In addition, "YS68" was expressed in CD34-positive undifferentiated hematocytes. Therefore, "YS68" is suggested to have an important function in primitive hematopoiesis.

The "YS68" protein of this invention is useful as a tool for elucidating the mechanism of primitive hematopoiesis, furthermore, its application to drug development for various diseases related to hematopoietic system is anticipated.

This invention relates to novel proteins involved in primitive hematopoiesis and genes encoding the proteins, as well as the production and use of the same. More specifically, this invention provides the following:

(1) a DNA selected from the group of:
  (a) a DNA encoding a protein comprising the amino acid sequence of SEQ ID NO:12 or 14;
  (b) a DNA comprising the coding region of the nucleotide sequence of SEQ ID NO:11 or 13;
  (c) a DNA encoding a protein comprising of the amino acid sequence of SEQ ID NO:12 or 14, in which one or more amino acids are modified by substitution, deletion, insertion and/or addition, wherein said protein is functionally equivalent to the protein consisting of the amino acid sequence of SEQ ID NO:12 or 14; and
  (d) a DNA hybridizing under stringent conditions with a DNA consisting of the nucleotide sequence of SEQ ID NO:11 or 13, and encoding a protein that is functionally equivalent to a protein consisting of the amino acid sequence of SEQ ID NO:12 or 14;

(2) a DNA encoding a partial peptide of a protein consisting of the amino acid sequence of SEQ ID NO:12 or 14;

(3) a protein or a peptide encoded by the DNA of any one of (1) or (2);

(4) a vector into which the DNA of any one of (1) or (2) is inserted;

(5) a host cell retaining the vector of (4);

(6) a method for producing the proteins or peptides of (3); comprising the step of culturing the host cells of (5), and recovering expressed protein from said host cell or the culture supernatant;

(7) a polynucleotide comprising at least 15 nucleotides that are complementary to a DNA consisting of the nucleotide sequence of SEQ ID NO:11 or 13 or to a complementary strand thereof;

(8) a method of screening for a compound that binds to the protein of (3), comprising the steps of:
  (a) contacting a test sample, containing at least one compound, with the protein or partial peptide of (3);
  (b) detecting the binding activity between the compound and the protein or partial peptide thereof; and
  (c) selecting the compound that has the activity to bind to the protein or partial peptide thereof;

(9) a compound binding to the protein of (3);

(10) the compound of (9), which is an antibody; and

(11) a compound binding to the protein of (3), which may be isolated by the method of (8).

The present invention provides novel proteins involved in primitive hematopoiesis and DNA encoding these proteins. The nucleotide sequence of the full-length cDNA of mouse "YS68" isolated by the present inventors is indicated in SEQ ID NO:11, and the amino acid sequence of the protein encoded by this cDNA is indicated in SEQ ID NO:12. In addition, the nucleotide sequence of the full-length cDNA of human "YS68" isolated by the present inventors is indicated in SEQ ID NO:13, and the amino acid sequence of the protein encoded by this cDNA is indicated in SEQ ID NO:14.

Hematopoietic stem cells contributing to lifelong hematopoiesis are formed by the differentiation of hemangioblasts, the common mother cells of hematocytes and blood vessels. Several transcription factors thought to be important for primitive hematopoiesis have been reported according to recent gene disruption experiments. Not only angiogenesis but also hematopoiesis was not confirmed in mouse with disruption in SCL (Porcher et al., Cell 86:47-57, 1996; Visvader et al., Genes Dev. 12:473-479, 1998). In addition, AML-1 and c-Myb knockout mice did not show abnormalities in angiogenesis, but they completely lacked definitive hematopoiesis (Okuda et al., Cell 84:321-330, 1996; Lin et al., Curr. Top Microbiol. Immunol. 211:79-87, 1996). However, how these transcription factors interact with each other at the stage of primitive hematopoiesis and become involved in determining the fate of cells remains unknown.

The mouse "YS68" gene (SEQ ID NO: 11) identified by the present inventors was isolated by subtracting cDNA derived from embryonic day 13 mouse yolk sac, which is said to lack the hemangioblast, from cDNA derived from embryonic day 9 yolk sac, which is suggested to have a hemangioblast. The isolated "Y568" gene (SEQ ID NO: 11) was expected to encode a protein of 1,265 amino acids, and showed an expression pattern with a high level expression in embryonic day 9 yolk sac followed by a gradual decrease. In addition, an expression of the gene was observed in the AGM region (considered to be the site of hematopoietic stem cell development) from day 10 embryos and in embryonic day 13 livers; the expression then shifted to strong expression at the thymus and spleen of day 16 embryos. Furthermore, expression in these regions considerably diminished in adult mice. Thus, the "Y568" cloned by the present inventors with such an expression pattern in the developmental stage can be considered as a new member of molecules involved in primitive hematopoiesis.

Although "YS68" is expected to be a nuclear protein because it has multiple nuclear transport signals in its C-terminal region, strong expression was observed not only in the nucleus but also around the nucleus in hepatocytes (Example 6). The finding that WD repeats necessary for binding to proteins existed in the N-terminus, and immunoprecipitation caused coprecipitation of multiple proteins (Example 4) suggested that transport of this protein to the nucleus is regulated by interactions with other proteins.

The idea that blood cells develop from the vascular endothelium has existed for a relatively long time, but was actually proven only recently. Jaffredo et al. stained the entire avian blood vessel with fluorescence-labeled LDL and revealed that the stained vascular endothelium differentiated into hematocytes (Jaffredo et al., Development 125:4575-4783, 1998). In addition, Hara et al. found that hemangioblasts can be concentrated by sorting the cells of the AGM region by PCLP-1 (podocalyxin-like protein 1). Localization of hemangioblasts in the vascular endothelium was suggested by the localized PCLP-1 expression in the AGM region in the vascular endothelium (Hara et al., Immunity 11:567-578, 1999). As shown in Example 5, the expression site of YS68 in the AGM region was the same vascular endothelium as PCLP-1. In addition, this expression pattern is the same as those of AML-1 and SCL, both of which are known to be important for primitive hematopoiesis. Considering that expression of YS68 in the hematocyte of CD34 positive cells, which are thought to be a group of relatively immature hematocytes (Example 6), is strong, YS68 is suggested to function in the process of differentiation from hemangioblasts to hematocytes.

The "YS68" proteins of this invention and DNAs encoding the proteins are useful as differentiation markers and as regulating factors of developmental differentiation and the hematopoietic function of hematopoietic stem cells. Additionally, they may be applicable for diagnosis, prevention, and treatment of diseases in which a protein of this invention is involved. In current medicine, means for artificial amplification of hematopoietic stem cells does not exist. Artificial in vitro proliferation of hematopoietic stem cells may be enabled by forced expression of YS68 using a virus vector in hemangioblasts that are the origin of hematopoietic cells, or by administration of cytokines or compounds that induces the expression of YS68. Therefore, YS68 may be applied to medical treatment, as a new alternative to bone marrow transplant.

In addition, many human blood cell tumors, such as myeloid leukemia and lymphoid leukemia, are often caused by abnormalities in transcription factors, and human "YS68" gene of this invention is likely to be one of the causative genes of these diseases. Therefore, human "YS68" may be particularly applied to genetic diagnosis or gene therapy of such diseases. Furthermore, drug development targeting the human "YS68" gene and protein themselves or molecules that regulate them, or molecules or genes that are regulated by the human "YS68" protein may be useful in the treatment and prevention of the above-mentioned diseases.

Furthermore, this invention includes proteins that are functionally equivalent to the "YS68" protein (SEQ ID NO:12 and 14). For example, mutant forms of the "YS68" protein are included in such proteins. The term "functionally equivalent" herein means that the protein of interest has the function of regulating the development and/or differentiation of hematopoietic cells or has the function of interacting with other proteins.

For example, the function of a protein to regulate the development and/or differentiation of hematopoietic cells can be evaluated using as an index the expression characteristics within the hematopoietic tissues, such as those described in Example 2. On the other hand, the function of a protein to interact with other proteins can be determined, for example, by utilizing immunoprecipitation, such as those described in Example 4.

As a method well known by a person skilled in the art for preparing a protein functionally equivalent to a given protein, methods for introducing mutations into proteins are known. For example, one skilled in the art can prepare proteins functionally equivalent to the "YS68" proteins (SEQ ID NO:12 and 14) by introducing an appropriate mutation in the amino acid sequence of the protein by site-directed mutagenesis (Hashimoto-Gotoh et al., Gene 152:271-275, 1995; Zoller et al., Methods Enzymol. 100:468-500, 1983; Kramer et al., Nucleic Acids Res. 12:9441-9456, 1984; Kramer et al., Methods. Enzymol. 154:350-367, 1987; Kunkel, Proc. Natl. Acad. Sci. USA 82:488-492, 1985; Kunkel, Methods Enzymol. 85:2763-2766, 1988). Mutation of amino acids can occur in nature, too. The proteins of the present invention include those proteins that comprise the amino acid sequences of the "YS68" protein (SEQ ID NO:12 and 14), wherein one or more amino acids are mutated and yet are functionally equivalent to the protein comprising the sequence of "YS68" protein. It is considered that the number of amino acids to be mutated in such a mutant, is generally 100 amino acids or less, preferably 50 amino acids or less, more preferably 20 amino acids or less, and more preferably 5 amino acid or less.

As for the amino acid residue to be mutated, it is preferable that it is mutated into a different amino acid such that the properties of the amino acid side-chain are conserved. Examples of properties of amino acid side chains are, hydrophobic amino acids (A, I, L, M, F, P, W, Y, V), hydrophilic amino acids (R, D, N, C, E, Q, G, H, K, S, T), and amino acids comprising the following side chains: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W) (The parenthetic letters indicate the one-letter codes of amino acids).

It is well known that a protein having deletion, addition, and/or substitution of one or more amino acid residues in the sequence of a protein can retain the original biological activity (Mark et al., Proc. Natl. Acad. Sci. USA 81:5662-5666, 1984; Zoller et al., Nucleic Acids Res. 10:6487-6500, 1982; Wang et al., Science 224:1431-1433; Dalbadie-McFarland et al., Proc. Natl. Acad. Sci. USA 79:6409-6413, 1982).

The term "substantially pure" as used herein in reference to a given polypeptide means that the polypeptide is substantially free from other biological macromolecules. For example, the substantially pure polypeptide is at least 75%, 80, 85, 95, or 99% pure by dry weight. Purity can be measured by any appropriate standard method known in the art, for example, by column chromatography, polyacrylamide gel electrophoresis, or HPLC analysis.

Accordingly, the invention includes a polypeptide having a sequence shown as SEQ ID NO:12 or 14. The invention also includes a polypeptide, or fragment thereof, that differs from the corresponding sequence shown as SEQ ID NO:12 or 14. The polypeptide can differ from the sequence of SEQ ID NO:12 or 14 by having one or more amino acids substituted, deleted, inserted and/or added. For example, the polypeptide can be a fusion protein, having an additional amino acid sequence at the N- or C-terminus of SEQ ID NO:12 or 14. In preferred embodiments, the protein has no more than 50, 30, 20, 10 or 5 amino acids substituted, deleted, inserted and/or added. Preferably, the difference is a difference or change at one or more non-essential residues or one or more conservative amino acid substitutions, as defined above. In one embodiment, the polypeptide includes an amino acid sequence at least about 60% identical to a sequence shown as SEQ ID NO:12 or 14, or a fragment thereof. Preferably, the polypeptide is at least 50%, 60%, 65%, 70%, 75%, 80%, 85%, 90%, 95%, 98%, 99% or more identical to SEQ ID NO:12 or 14 and has at least one YS68 activity described herein, e.g., the protein can regulate development or differentiation of hematopoietic cells. Preferred polypeptide fragments of the invention are at least 10%, preferably at least 20%, 30%, 40%, 50%, 60%, 70%, or more, of the length of the sequence shown as SEQ ID NO:12 or 14 and have at least one YS68 activity described herein. Or alternatively, the fragment can be merely an immunogenic fragment.

A fusion protein comprising "YS68" protein is encompassed in the protein, wherein one or more amino acids residues are added to the amino acid sequence of "YS68". Fusion proteins are fusions of the "YS68" protein and other peptides or proteins, and are included in the present invention. Fusion proteins can be made by techniques well known to a person skilled in the art, such as by linking the DNA encoding the "YS68" protein (SEQ ID NO:12 and 14) with DNA encoding other peptides or proteins so as the frames match, inserting this linked DNA into an expression vector, and expressing it in a host. There is no restriction as to the peptides or proteins to be fused to a protein of the present invention.

Known peptides, for example, FLAG (Hopp et al., Biotechnology 6:1204-1210, 1988), 6×His consisting of six His (histidine) residues, 10×His, Influenza agglutinin (HA), human c-myc fragment, VSV-GP fragment, p18HIV fragment, T7-tag, HSV-tag, E-tag, SV40T antigen fragment, lck tag, α-tubulin fragment, B-tag, Protein C fragment, and such, can be used as peptides to be fused to a protein of the present invention. Examples of proteins that may be fused to a protein of the present invention are, GST (glutathione-S-transferase), Influenza agglutinin (HA), immunoglobulin constant region, β-galactosidase, MBP (maltose-binding protein), and such. Fusion proteins can be prepared by fusing commercially available DNA encoding these peptides or proteins with a DNA encoding a protein of the present invention and expressing the fused DNA prepared.

Furthermore, a protein, in which multiple amino acid residues have been added to the amino acid sequence of the "YS68" protein, includes a protein encoded by the nucleotide sequence starting from "a" at position 98 to "g" at position 6922 of SEQ ID NO:15 (protein comprising the amino acid sequence, wherein an amino acid sequence comprising "Met-Ala-Ala-Glu-Arg-Arg-Cys-Gly-Ser" (SEQ ID NO:16) is added to the N terminus of the amino acid sequence of SEQ ID NO:14).

In addition, as a method well known to those skilled in the art for preparing proteins that are functionally equivalent to a known protein, methods that utilize hybridization techniques (Sambrook et al., Molecular Cloning 2nd ed., 9.47-9.58, Cold Spring Harbor Lab. Press, 1989) can be mentioned. More specifically, those skilled in the art may readily isolate DNAs having high homology to the DNA sequences (SEQ ID NO:11 and 13) encoding the "YS68" protein, based on the entire DNA sequence or parts thereof, and isolate DNA encoding proteins functionally equivalent to the "YS68" protein from these DNAs. The present invention includes proteins that are functionally equivalent to the "YS68" protein, and which are encoded by DNAs that hybridize under stringent conditions with DNA encoding the "YS68" protein. When isolating a cDNA that has high sequence homology to the DNA encoding the "YS68" protein, it is considered to be preferable to use embryonic stage hematopoietic tissues (for example, tissues such as the AGM region and yolk sac during early development; and thymus, spleen, and liver during mid to late development).

Hybridization conditions for isolating DNAs encoding proteins that are functionally equivalent to the "YS68" protein can be appropriately selected by those skilled in the art. Conditions for hybridization, for example, may be those with low stringency. Low stringency conditions means that the washing conditions after hybridization are, for example, 42° C., 2×SSC, and 0.1% SDS, or preferably 50° C., 2×SSC, and 0.1% SDS. Examples of hybridization conditions that are more preferable are conditions with high stringency. An example of high stringency conditions is 65° C., 0.1×SSC and 0.1% SDS. Under these conditions, the higher the temperature, the higher the homology of the obtained DNA will be. However, several factors such as temperature and salt concentration can influence the stringency of hybridization and one skilled in the art can appropriately select such factors to accomplish a similar stringency.

In addition, instead of hybridization, DNA encoding functionally equivalent proteins to "YS68" protein can be isolated by gene amplification methods, for example, by polymerase chain reaction (PCR), which uses primers that are synthesized based on sequence information of DNA encoding the "YS68" protein (SEQ ID NO:11 and 13).

A protein that is functionally equivalent to a "YS68" protein, encoded by a DNA that is isolated by such hybridization techniques and gene amplification techniques, will normally have a high amino acid sequence homology to the "YS68" protein (SEQ ID NO:12 and 14). The proteins of this invention also include proteins that are functionally equivalent to a "YS68" protein and at the same time have a high sequence homology to the amino acid sequence of SEQ ID NO:12 or 14. High sequence homology typically means a homology of 30% or more, preferably a homology of 50% or more, more preferably a homology of 70% or more, and even more preferably a homology of 90% or more (for example, homology of 95% or more). To determine the homology of a protein, an algorithm described in the literature (Wilbur et al., Proc. Natl. Acad. Sci. USA 80:726-730, 1983) can be used.

The proteins of this invention may have different amino acid sequences, molecular weights, and isoelectric points, as well as differences in the presence or absence of sugar chains and their forms, depending on the cells or hosts to produce the protein or production method, which will be described later. However, so long as the obtained protein has the same function as the "YS68" protein, it is included in this invention. For example, if a protein of this invention is expressed in a prokaryotic cell such as *E. coli*, a methionine residue will be added to the N terminus of the amino acid sequence of the original protein. The proteins of this invention will also include such proteins.

The proteins of the present invention can be prepared as recombinant proteins or naturally occurring proteins, by methods well known by those skilled in the art. A recombinant DNA can be prepared by inserting a DNA (for example, the DNA comprising the nucleotide sequence of SEQ ID NOs: 11 or 13) which encodes a protein of the present invention into an appropriate vector, collecting the recombinant obtained by introducing the vector into appropriate host cells, obtaining the extract, and purifying by subjecting the extract to chromatography such as ion exchange, reverse, gel filtration, or affinity chromatography in which an antibody against a protein of the present invention is fixed on column or by combining more than one of these columns.

Also when a protein of the present invention is expressed within host cells (for example, animal cells and *E. coli*) as a fusion protein with glutathione-S-transferase protein or as a recombinant protein supplemented with multiple histidines, the expressed recombinant protein can be purified using a glutathione column or nickel column.

After purifying the fusion protein, it is also possible to exclude regions other than the objective protein by cutting with thrombin or factor-Xa as required.

A naturally occurring protein can be isolated by methods known by a person skilled in the art, for example, by using an affinity column in which the antibody binding to a protein of the present invention (described below) is bound against an extract of tissues or cells expressing a protein of the present invention is expressed. An antibody can be a polyclonal or a monoclonal antibody.

The present invention also contains partial peptides of the proteins of the present invention. A partial peptide of the present invention comprises at least 7 amino acids or more, preferably 8 amino acids or more, and more preferably 9 amino acids or more. The partial peptides can be used, for example, for preparing an antibody against a protein of the present invention, screening a compound binding to a protein of the present invention, and for screening accelerators or inhibitors of a protein of the present invention. The partial peptides can be also used as antagonists or a competitive inhibitors against a protein of the present invention.

A partial peptide of the invention can be produced by genetic engineering, known methods of peptide synthesis, or by digesting a protein of the invention with an appropriate peptidase. For peptide synthesis, for example, solid phase synthesis or liquid phase synthesis may be used.

As used herein, an "isolated nucleic acid" is a nucleic acid, the structure of which is not identical to that of any naturally occurring nucleic acid or to that of any fragment of a naturally occurring genomic nucleic acid spanning more than three genes. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in random, uncharacterized mixtures of different DNA molecules, transfected cells, or cell clones, e.g., as these occur in a DNA library such as a cDNA or genomic DNA library.

Accordingly, in one aspect, the invention provides an isolated or purified nucleic acid molecule that encodes a polypeptide described herein or a fragment thereof Preferably, the isolated nucleic acid molecule includes a nucleotide sequence that is at least 60% identical to the nucleotide sequence shown in SEQ ID NO:11 or 13. More preferably, the isolated nucleic acid molecule is at least 65%, 70%, 75%, 80%, 85%, 90%, 91%, 92%, 93%, 94%, 95%, 96%, 97%, 98%, 99%, or more, identical to the nucleotide sequence shown in SEQ ID NO:11 or 13. In the case of an isolated nucleic acid molecule which is longer than or equivalent in length to the reference sequence, e.g., SEQ ID NO:11 or 13, the comparison is made with the full length of the reference sequence. Where the isolated nucleic acid molecule is shorter that the reference sequence, e.g., shorter than SEQ ID NO:11 or 13, the comparison is made to a segment of the reference sequence of the same length (excluding any loop required by the homology calculation).

As used herein, "% identity" of two amino acid sequences, or of two nucleic acid sequences, is determined using the algorithm of Karlin and Altschul (Proc. Natl. Acad. Sci. USA 87:2264-2268, 1990), modified as in Karlin and Altschul, Proc. Natl. Acad. Sci. USA 90:5873-5877, 1993). Such an algorithm is incorporated into the NBLAST and XBLAST programs of Altschul et al. (J. Mol. Biol. 215:403-410, 1990). BLAST nucleotide searches are performed with the NBLAST program, score=100, wordlength=12. BLAST protein searches are performed with the XBLAST program, score=50, wordlength=3. To obtain gapped alignment for comparison purposes GappedBLAST is utilized as described in Altschul et al. (Nucleic Acids Res. 25:3389-3402, 1997). When utilizing BLAST and GappedBLAST programs the default parameters of the respective programs (e.g., XBLAST and NBLAST) are used to obtain nucleotide sequences homologous to a nucleic acid molecule of the invention.

A DNA encoding a protein of the present invention can be used for the production of the protein in vivo or in vitro as described above as well as for, for example, application to gene therapy for diseases attributed to genetic abnormality in the gene encoding the protein of the present invention. Any form of the DNA can be used, so long as it encodes a protein of the present invention. Specifically, cDNA synthesized from mRNA, genomic DNA, or chemically synthesized DNA can be used. The present invention includes a DNA comprising a given nucleotide sequence based on degeneracy of genetic codons, as long as it encodes a protein of the present invention.

A DNA of the present invention can be prepared by methods known to those skilled in the art. For example, a DNA of the present invention can be prepared from a cDNA library from cells which express a protein of the present invention by conducting hybridization using a partial sequence of the DNA of the present invention (e.g., SEQ ID NO:11 and 13) as a probe. A cDNA library can be prepared, for example, by the method described in Sambrook et al., Molecular Cloning, Cold Spring Harbor Laboratory Press, 1989, or using commercially available cDNA libraries. A cDNA library can be also prepared by extracting RNA from cells expressing a protein of the present invention, synthesizing cDNA using reverse transcriptase, synthesizing an oligo DNA base on the sequence of the DNA of the present invention (for example, SEQ ID NOs:11 and 13), conducting PCR by using these as primers, and amplifying cDNA encoding the protein of the present invention.

In addition, by sequencing the nucleotides of the obtained cDNA, a translation region encoded by the cDNA can be determined, and the amino acid sequence of a protein of the present invention can be obtained. Moreover, by screening the genomic DNA library using the obtained cDNA as a probe, genomic DNA can be isolated.

More specifically, mRNAs may first be prepared from a cell, tissue, or organ (for example, embryonic stage hematopoietic tissues such as AGM region and yolk sac of early development; thymus, spleen, and liver of mid to late development) in which a protein of the invention is expressed. Known methods can be used to isolate mRNAs; for instance, total RNA is prepared by the guanidine ultracentrifugation (Chirgwin et al., Biochemistry 18:5294-5299, 1979) or the AGPC method (Chomczynski et al., Anal. Biochem. 162: 156-159, 1987), and mRNA is purified from total RNA using mRNA Purification Kit (Pharmacia) and such. Alternatively, mRNA may be directly purified by QuickPrep mRNA Purification Kit (Pharmacia).

The obtained mRNA is used to synthesize cDNA using reverse transcriptase. A cDNA may be synthesized using kits, such as the AMV Reverse Transcriptase First-strand cDNA Synthesis Kit (Seikagaku Kogyo). Alternatively, a cDNA may be synthesized and amplified following the 5'-RACE method (Frohman et al., Proc. Natl. Acad. Sci. USA 85:8998-9002, 1988; Belyavsky et al., Nucleic Acids Res. 17:2919-2932, 1989) which uses a primer and such, described herein, the 5'-Ampli FINDER RACE Kit (Clontech), and polymerase chain reaction (PCR).

A desired DNA fragment is prepared from the PCR products and ligated with a vector DNA. The recombinant vectors are used to transform E. coli and such, and a desired recombinant vector is prepared from a selected colony. The nucleotide sequence of the desired DNA can be verified by conventional methods, such as the dideoxynucleotide chain termination method.

A DNA of the invention may be also designed to have a sequence that is expressed more efficiently by taking into account the frequency of codon usage in the host to be used for expression (Grantham et al., Nucleic Acids Res. 9:43-74, 1981). A DNA of the present invention may be altered by a commercially available kit or a conventional method. For instance, a DNA may be altered by digestion with restriction enzymes, insertion of synthetic oligonucleotides or appropriate DNA fragments, addition of linkers, or insertion of the initiation codon (ATG) and/or the stop codon (TAA, TGA, or TAG).

The DNAs of this invention include a DNA that (a) hybridizes under stringent conditions with a DNA consisting of the nucleotide sequence of SEQ ID NO:11 or 13 and (b) encodes a protein that is functionally equivalent to a protein of this invention mentioned above. Stringent conditions for hybridization can be selected appropriately by those skilled in the art, and those conditions specifically mentioned above may be used. Under these conditions, DNA having higher homology are obtained as the temperature is raised. The above-mentioned DNA to be hybridized is preferably a naturally occurring DNA, for example, a cDNA or chromosomal DNA.

The present invention also provides vectors into which a DNA of the present invention is inserted. The vectors of the present invention are useful to retain a DNA of the present invention in host cell, or to express a protein of the present invention.

When E. coli is used as the host cell and a vector is amplified therein to produce a large amount in E. coli (e.g., JM109, DH5α, HB101, or XL1Blue), the vector should have an "ori" that may be amplified in E. coli and a marker gene for selecting transformed E. coli (e.g., a drug-resistance gene selected by a drug (e.g., ampicillin, tetracycline, kanamycin, or chloramphenicol)). For example, the M13-series vectors, the pUC-series vectors, pBR322, pBluescript, pCR-Script, and so on can be used. In addition to the vectors described above, pGEM-T, pDIRECT, and pT7, for example can also be used for subcloning and extracting cDNA. When a vector is used to produce a protein of the present invention, an expression vector is especially useful. For example, an expression vector to be expressed in E. coli should have the above characteristics to be amplified in E. coli. When E. coli, such as JM109, DH5α, HB101, or XL1 Blue, are used as the host cell, the vector should, in addition to the above characteristics, have a promoter so that the vector is copied in the host, for example, the lacZ promoter (Ward et al., Nature 341:544-546, 1989; FASEB J. 6:2422-2427, 1992), the araB promoter (Better et al., Science 240:1041-1043, 1988), or the T7 promoter and such, that can efficiently express the desired gene in *E. coli*. As such a vector, for example, pGFX-5X-1 (Pharmacia), "QIAexpress system" (Qiagen), pEGFP or pET (in this case, the host is preferably BL21 which expresses T7 RNA polymerase) can be used in addition to the above vectors.

A vector also may contain a signal sequence for polypeptide secretion. As a signal sequence for protein secretion, the pelB signal sequence (Lei et al., J. Bacteriol. 169:4379, 1987) can be used in the case of producing proteins into the periplasm of *E. coli*. For introducing a vector into host cells, for example, the calcium chloride method, and the electroporation method can be used.

Besides *E. coli*, for example, expression vectors derived from mammals (for example, pcDNA3 (Invitrogen) and pEGF-BOS (Nucleic Acids. Res. 18(17):5322, 1990), pEF, pCDM8); expression vectors derived from insect cells (for example, "Bac-to-BAC baculovirus expression system" (GIBCO BRL), pBacPAK8); expression vectors derived from plants (for example pMH1, pMH2); expression vectors derived from animal viruses (for example, pHSV, pMV, pAdexLcw); expression vectors derived from retroviruses (for example, pZIPneo); expression vector derived from yeast (for example, "Pichia Expression Kit" (Invitrogen), pNV11, SP-Q01); expression vectors derived from *Bacillus subtilis* (for example, pPL608, pKTH50) can be used as vectors for producing a protein of the present invention.

In order to express a vector in animal cells, such as CHO, COS, or NIH3T3 cells, the vector should have a promoter necessary for expression in such cells, for example, the SV40 promoter (Mulligan et al., Nature 277:108, 1979), the MMLV-LTR promoter, the EF1α promotor (Mizushima et al., Nucleic Acids Res. 18:5322, 1990), or the CMV promoter, and such, and preferably a marker gene for selecting transformants (for example, a drug resistance gene selected by a drug (e.g., neomycin, G418)). Examples of vectors with these characteristics include pMAM, pDR2, pBK-RSV, pBK-CMV, pOPRSV, pOp13, and so on.

In addition, for the purpose of stably expressing a gene and amplifying the copy number of the gene in cells, for example, a method wherein a vector comprising the complementary DHFR gene (for example pCHO I) is introduced into CHO cells in which the nuclei acid synthesizing pathway is deleted and amplified by methotrexate (MTX) can be used. On the other hand, in the case of transient expression of a gene, a method wherein a vector (e.g., pcD) comprising replication origin of SV40 is transformed using COS cells comprising the SV40 T antigen expressing gene on chromosomes can be used. The origin used for replication may be those of polyomavirus, adenovirus, bovine papilloma virus (BPV), and the like. In addition, the expression vector may include a selection marker gene for amplification of the gene copies in host cells. Examples of such markers include, but are not limited to, the aminoglycoside transferase (APH) gene, the thymidine kinase (TK) gene, the *E. coli* xanthine-guanine phosphoribosyl transferase (Ecogpt) gene, and the dihydrofolate reductase (dhfr) gene.

On the other hand, a DNA of the present invention can be expressed in vivo in animals, for example, by inserting a DNA of the present invention into an appropriate vector and introducing it in vivo by a conventional method, such as the retrovirus method, the liposome method, the cationic liposome method, and the adenovirus method. By using these methods, gene therapy against diseases attributed to mutation of 'YS68' gene of the present invention can be effected. As a vector, for example, adenovirus vector (for example pAdex-lcw), and retrovirus vector (for example, pZIPneo) can be used, but the present invention is not restricted thereto. Common gene manipulation, for example, insertion of a DNA of the present invention to a vector, can be performed according to any standard method (Molecular Cloning, 5.61-5.63). Administration into a living body can be either an ex vivo method, or in vivo method.

The present invention relates to a host cell into which a vector of the present invention has been introduced. The host cell into which a vector of the invention is introduced is not particularly limited. *E. coli* or various animal cells can be used. The host cells of the present invention can be used, for example, as production system for producing or expressing a protein of the present invention. The present invention provides methods of producing a protein of the invention both in vitro or in vivo. For in vitro production, eukaryotic cells or prokaryotic cells can be used as host cells.

Useful eukaryotic cells as host include animal, plant, or fungi cells. As animal cells, mammalian cells, such as CHO (J. Exp. Med. 108:945, 1995), COS, 3T3, myeloma, baby hamster kidney (BHK), HeLa, and Vero cells; amphibian cells, such as *Xenopus* oocytes (Valle et al., Nature 291:340-358, 1981); or insect cells, such as Sf9, Sf21, and Tn5 cells can be used. CHO cells lacking the DHFR gene (dhfr-CHO) (Proc. Natl. Acad. Sci. USA 77:4216-4220, 1980) or CHO K-1 (Proc. Natl. Acad. Sci. USA 60:1275, 1968) may be also used. In animal cells, CHO cells are particularly preferable for mass expression. A vector can be introduced into host cells by, for example, the calcium phosphate method, the DEAE dextran method, the cationic liposome DOTAP (Boehringer Mannheim), the electroporation method, or the lipofection method.

As plant cells, plant cells originating from *Nicotiana tabacum* are known as a protein-production system, and may be used as callus cultures. As fungi cells, yeast cells such as *Saccharomyces*, including *Saccharomyces cerevisiae*, or filamentous fungi such as *Aspergillus*, including *Aspergillus niger*, are known and may be used herein.

Useful prokaryotic cells include bacterial cells, such as *E. coli*, for example, JM109, DH5α, HB101 are known. Regarding others, *Bacillus subtilis* is known.

These host cells are transformed by a desired DNA, and the resulting transformants are cultured in vitro to obtain a protein. Transformants can be cultured using known methods. Culture medium for animal cell, for example, DMEM, MEM, RPMI1640, or IMDM may be used with or without serum supplement such as fetal calf serum (FCS). The pH of the culture medium is preferably between about pH 6 to 8. Such cells are typically cultured at about 30 to 40° C. for about 15 to 200 hr, and the culture medium may be replaced, aerated, or stirred if necessary.

Animal and plant hosts may be used for in vivo production. For example, a desired DNA can be introduced into an animal or plant host. Encoded proteins are produced in vivo, and then recovered. These animal and plant hosts are included in the host cells of the present invention.

Animals to be used for the production systems described above include, but are not limited to, mammals and insects. Mammals, such as goat, porcine, sheep, mouse, and bovine, may be used (Vicki Glaser, SPECTRUM Biotechnology Applications (1993)). Alternatively, the mammals may be transgenic animals.

For instance, a desired DNA may be prepared as a fusion gene with a gene encoding a protein specifically produced into milk, such as goat β casein. DNA fragments comprising a fusion gene having the desired DNA are injected into goat embryos, which are then introduced back to female goats. Proteins are recovered from milk produced by the transgenic goats (i.e., those born from the goats that had received the modified embryos) or from their offspring. To increase the amount of milk containing the proteins produced by transgenic goats, appropriate hormones may be administered to them (Ebert et al., Bio/Technology 12:699-702, 1994).

Alternatively, insects, such as the silkworm, may be used. A desired DNA inserted into baculovirus can be used to infect silkworms, and a desired protein is then recovered from their body fluid (Susumu et al., Nature 315:592-594, 1985).

As plants, for example, tobacco can be used. In use of tobacco, a desired DNA is inserted into a plant expression vector, such as pMON530, which is then introduced into a bacteria, such as *Agrobacterium tumefaciens*. Then, the bacteria is used to infect tobacco, such as *Nicotiana tabacum*, and a desired polypeptide is recovered from the leaves of the plant (Julian et al., Eur. J. Immunol. 24:131-138, 1994).

A protein of the present invention obtained as above may be isolated from the interior or exterior (e.g. medium) of the cells or hosts, and purified as a substantially pure homogeneous protein. The method for protein isolation and purification is not limited to any specific method; in fact, any standard method may be used. For instance, column chromatography, filter, ultrafiltration, salt precipitation, solvent precipitation, solvent extraction, distillation, immunoprecipitation, SDS-polyacrylamide gel electrophoresis, isoelectric point electrophoresis, dialysis, and recrystallization may be appropriately selected and combined to isolate and purify the protein.

For chromatography, for example, affinity chromatography, ion-exchange chromatography, hydrophobic chromatography, gel filtration, reverse phase chromatography, adsorption chromatography, and such may be used (Strategies for Protein Purification and Characterization: A Laboratory Course Manual. Ed. Daniel R. Marshak et al., Cold Spring Harbor Laboratory Press, 1996). These chromatographies may be performed by liquid chromatography, such as HPLC and FPLC. Thus, the present invention provides for highly purified proteins, produced by the above methods.

A protein of the present invention may be optionally modified or partially deleted by treating it with an appropriate protein modification enzyme before or after purification. Useful protein modification enzymes include, but are not limited to, trypsin, chymotrypsin, lysylendopeptidase, protein kinase, and glucosidase.

The present invention provides an antibody that binds to a protein of the invention. The antibody of the invention can be used in any form, such as monoclonal or polyclonal antibodies, and includes antiserum obtained by immunizing a rabbit with a protein of the invention, all classes of polyclonal and monoclonal antibodies, human antibodies, and humanized antibodies produced by genetic recombination.

A protein of the invention used as an antigen to obtain an antibody may be derived from any animal species, but is preferably derived from a mammal such as a human, mouse, or rat, or more preferably from a human. A human-derived protein may be obtained from the nucleotide or amino acid sequences disclosed herein.

In the present invention, a protein to be used as an immunization antigen may be a complete protein or a partial peptide of a protein. A partial peptide may be, for example, an amino (N)-terminal or carboxy (C)-terminal fragment of the protein. Herein, "an antibody" is defined as an antibody that specifically reacts with either the full-length or a fragment of a protein.

A gene encoding a protein of the invention or its fragment may be inserted into a known expression vector, which is then used to transform a host cell as described herein. The desired protein or its fragment may be recovered from the exterior or interior of the host cells by any standard method, and may be used as an antigen. Alternatively, cells expressing the protein or their lysates, or a chemically synthesized protein may be used as an antigen. Short peptides are preferably bound with carrier proteins such as bovine serum albumin, ovalbumin, and keyhole limpet hemocyanin to be used as the antigen.

Any mammalian animal may be immunized with the antigen, but preferably the compatibility with parental cells used for cell fusion is taken into account. In general, animals of the orders Rodentia, Lagomorpha, or Primate are used.

Rodents include, for example, mouse, rat, and hamster. Lagomorphs include, for example, rabbit. Primates include, for example, a monkey of catarrhine (old world monkey) such as *Macaca fascicularis*, rhesus monkey, sacred baboon, or chimpanzee.

Methods for immunizing animals against antigens are known in the art. Intraperitoneal injection or subcutaneous injection of antigens is used as a standard method for immunization of mammals. More specifically, antigens may be diluted and suspended in an appropriate amount with phosphate buffered saline (PBS), physiological saline, etc. If desired, the antigen suspension may be mixed with an appropriate amount of a standard adjuvant, such as Freund's complete adjuvant, made into emulsion, and then administered to mammalian animals. Preferably, it is followed by several administrations of antigen mixed with an appropriately amount of Freund's incomplete adjuvant every 4 to 21 days. An appropriate carrier may also be used for immunization. After immunization as above, serum is examined for increase of the amount of desired antibodies by a standard method.

Polyclonal antibodies against a protein of the present invention may be prepared by collecting blood from the immunized mammal examined for the increase of desired antibodies in the serum, and separating serum from the blood by any conventional method. Polyclonal antibodies may be used as serum containing the polyclonal antibodies, or if necessary, a fraction containing the polyclonal antibodies may be isolated from the serum. Immunoglobulin G or M can be prepared by obtaining a fraction which recognizes only a protein of the present invention using an affinity column coupled with the protein of the present invention and further purifying this fraction by using protein A or protein G column.

To prepare monoclonal antibodies, immune cells are collected from the mammal immunized against an antigen and checked for the increased level of desired antibodies in the serum as described above, and are subjected to cell fusion. The immune cells used for cell fusion are preferably obtained from spleen. Other parental cells can be fused with the above immunocyte; for example, preferably myeloma cells of mammalians, and more preferably myeloma cells which acquired the property for selecting fused cells by drugs can be used.

The above immunocyte and myeloma cells can be fused by known methods, for example, the method by Milstein et al. (Galfre et al., Methods Enzymol. 73:3-46, 1981).

Resulting hybridomas obtained by the cell fusion may be selected by cultivating them in a standard selection medium, such as the HAT medium (medium containing hypoxanthine, aminopterin, and thymidine). The cell culture is typically continued in the HAT medium for several days to several weeks, a sufficient time to allow all the other cells, except desired hybridoma (non-fused cells), to die. Then, by the standard limiting dilution method, a hybridoma cell producing the desired antibody is screened and cloned.

In addition to the above method, in which a non human animal is immunized against an antigen for preparing hybridoma, human lymphocytes, such as that infected by EB virus, may be immunized with a protein, protein expressing cells, or their lysates in vitro. Then, the immunized lymphocytes are fused with human-derived myeloma cells capable of indefinitely dividing, such as U266, to yield a hybridoma producing a desired human antibody having binding ability to the protein can be obtained (Unexamined Published Japanese Patent Application (JP-A) No. Sho 63-17688).

Next, the monoclonal antibody, obtained by transplanting the obtained hybridomas into the abdominal cavity of a mouse and by extracting ascites, can be purified by, for example, ammonium sulfate precipitation, protein A or protein G column, DEAE ion exchange chromatography, or an affinity column to which a protein of the present invention is coupled. An antibody of the present invention can be used not only for purification and detection of a protein of the present invention, but also as a candidate for agonists and antagonists of a protein of the present invention. In addition, an antibody can be applied to antibody treatment for diseases associated with a protein of the present invention. When the obtained antibody is used for the administration to the human body (antibody treatment), a human antibody or a humanized antibody is preferable for reducing immunogenicity.

For example, transgenic animals having a repertory of human antibody genes may be immunized against a protein, protein expressing cells, or their lysates as an antigen. Antibody producing cells are collected from the animals, and fused with myeloma cells to obtain hybridoma, from which human antibodies against a protein can be prepared (see WO92-03918, WO93-2227, WO94-02602, WO94-25585, WO96-33735, and WO96-34096).

Alternatively, an immune cell, such as an immunized lymphocyte, producing antibodies may be immortalized by an oncogene and used for preparing monoclonal antibodies.

Monoclonal antibodies thus obtained can be also recombinantly prepared using genetic engineering techniques (see, for example, Borrebaeck C. A. K. and Larrick, J. W., THERAPEUTIC MONOCLONAL ANTIBODIES, published in the United Kingdom by MACMILLAN PUBLISHERS LTD, 1990). A DNA encoding an antibody may be cloned from an immune cell, such as a hybridoma or an immunized lymphocyte producing the antibody, inserted into an appropriate vector, and introduced into host cells to prepare a recombinant antibody. The present invention also provides recombinant antibodies prepared as described above.

Furthermore, an antibody of the present invention may be a fragment of an antibody or modified antibody, so long as it binds to one or more of the proteins of the invention. For instance, the antibody fragment may be Fab, F(ab')$_2$, Fv, or single chain Fv (scFv), in which Fv fragments from H and L chains are ligated by an appropriate linker (Huston et al., Proc. Natl. Acad. Sci. USA 85:5879-5883, 1988). More specifically, an antibody fragment may be generated by treating an antibody with enzymes such as papain or pepsin. Alternatively, a gene encoding an antibody fragment may be constructed, inserted into an expression vector, and expressed in an appropriate host cell (see, for example, Co et al., J. Immunol. 152:2968-2976, 1994; Better et al., Methods Enzymol. 178:476-496, 1989; Pluckthun et al., Methods Enzymol. 178: 497-515, 1989; Lamoyi, Methods Enzymol. 121:652-663, 1986; Rousseaux et al., Methods Enzymol. 121:663-669, 1986; Bird et al., Trends Biotechnol. 9:132-137, 1991).

An antibody may be modified by conjugation with a variety of molecules, such as polyethylene glycol (PEG). The present invention provides such modified antibodies. The modified antibody can be obtained by chemically modifying an antibody. These modification methods are conventional in this field.

Alternatively, an antibody of the present invention may be obtained as a chimeric antibody, between a variable region derived from nonhuman antibody and the constant region derived from human antibody; or as a humanized antibody, comprising the complementarity determining region (CDR) derived from nonhuman antibody, the frame work region (FR) derived from human antibody, and the constant region.

Obtained antibodies may be purified into homogeneity. An antibody used in the present invention can be separated and purified by conventional methods used for separating and purifying usual proteins. For example, the separation and purification of a protein can be performed by an appropriately selected and combined use of column chromatography, such as affinity chromatography, filter, ultrafiltration, salting-out, dialysis, SDS polyacrylamide gel electrophoresis, isoelectric focusing, and others (Antibodies: A Laboratory Manual. Ed Harlow and David Lane, Cold Spring Harbor Laboratory, 1988); however, the present invention is not limited thereto. The concentration of antibodies obtained above can be determined by measuring absorbance, by the enzyme-linked immunosorbent assay (ELISA), and so on.

Examples of columns used for affinity chromatography include protein A columns and protein G columns. Examples of columns using protein A column include Hyper D, POROS, Sepharose F. F. (Pharmacia), etc.

In addition to affinity chromatography, the chromatography includes, for example, ion-exchange chromatography, hydrophobic chromatography, gel filtration, reverse-phase chromatography, adsorption chromatography, and the like (Strategies for Protein Purification and Characterization: A Laboratory Course Manual. Ed Daniel R. Marshak et al., Cold Spring Harbor Laboratory Press, 1996). The chromatographic procedures can be carried out by liquid-phase chromatography such as HPLC, FPLC, or the like.

For example, measurement of absorbance, enzyme-linked immunosorbent assay (ELISA), enzyme immunoassay (EIA), radioimmunoassay (RIA), and/or immunofluorescence may be used to measure the antigen binding activity of an antibody of the invention. In ELISA, an antibody of the present invention is immobilized on a plate, a protein of the invention is applied to the plate, and then a sample containing a desired antibody, such as culture supernatant of antibody producing cells or purified antibodies, is applied. Then, a secondary antibody that recognizes the primary antibody and is labeled with an enzyme, such as alkaline phosphatase, is applied, and the plate is incubated. Next, after washing, an enzyme substrate, such as p-nitrophenyl phosphate, is added to the plate, and the absorbance is measured to evaluate the antigen binding activity of the sample. A fragment of a protein, such as a C-terminal fragment, may be used as a protein. BIAcore (Pharmacia) may be used to evaluate the activity of an antibody according to the present invention.

The above methods allow for the detection or measurement of the proteins of the invention, by exposing an antibody of the invention to a sample assumed to contain a protein of the invention, and detecting or measuring the immune complex formed by the antibody and the protein. Because the method of detection or measurement of proteins according to the invention can specifically detect or measure proteins, the method may be useful in a variety of experiments in which the protein is used.

The present invention provides a polynucleotide having at least 15 nucleotides that is complementary to the DNA that encodes the "YS68" protein (SEQ ID NO:11 or 13) or the complementary strand thereof.

Herein, the term "complementary strand" is defined as one strand of a double strand DNA composed of A:T and G:C base pairs to the other strand. In addition, "complementary" is defined as not only those completely matching within a continuous region of at least 15 nucleotides, but also having a homology of at least 70%, preferably at least 80%, more preferably 90%, and even more preferably 95% or higher within that region. The homology may be determined using the algorithm described herein.

Probes or primers for detection and amplification of a DNA encoding a protein of this invention, or nucleotides or nucleotide derivatives for suppressing protein expression (for example, antisense oligonucleotides and ribozymes, or DNA encoding them) are included in these polynucleotides. In addition, such polynucleotides may be also used for preparing DNA chips.

When used as a primer, the region on the 3' side is designed to be complementary to a DNA encoding a protein of the invention, and restriction enzyme recognition sequence and tags can be added to the 5' side.

For example, an antisense oligonucleotide that hybridizes with a portion of the nucleotide sequence of SEQ ID NO:11 or 13 is also included in the antisense oligonucleotides of the present invention. An antisense oligonucleotide is preferably one against at least 15 continuous nucleotides in the nucleotide sequence of SEQ ID NO:11 or 13. More preferably, it is an antisense oligonucleotide having at least 15 continuous nucleotides that contains the translation initiation codon.

Derivatives or modified products of antisense oligonucleotides can be used as antisense oligonucleotides. Examples of such modified products are, lower alkyl phosphonate modifications such as methyl-phosphonate-type or ethyl-phosphonate-type, phosphothioate modifications and phosphoamidate modifications.

The term "antisense oligonucleotides" as used herein means, not only those in which the entire nucleotides corresponding to those constituting a specified region of a DNA or mRNA are complementary, but also those having a mismatch of one or more nucleotides, so long as DNA or mRNA and an oligonucleotide can specifically hybridize with the nucleotide sequence of SEQ ID NO:11 or 13.

An antisense oligonucleotide derivative of the present invention has inhibitory effect on the function of a protein of the present invention as a result that the derivative inhibits the expression of the protein of the invention by acting upon cells producing the protein of the invention and by binding to the DNA or mRNA encoding the protein to inhibit its transcription or translation or to promote the degradation of the mRNA.

An antisense oligonucleotide derivative of the present invention can be made into an external preparation, such as a liniment and a poultice, by mixing with a suitable base material which is inactive against the derivatives.

Also, as necessary, the derivatives can be formulated into tablets, powders, granules, capsules, liposome capsules, injections, solutions, nose-drops, and freeze-drying agents and such by adding excipients, isotonic agents, solubilizing agents, stabilizers, preservative substance, pain-killers, and such. These can be prepared by following usual methods.

An antisense oligonucleotide derivative is given to a patient by directly applying onto the ailing site or by injecting into a blood vessel so that it will reach the site of ailment. An antisense-mounting medium can also be used to increase durability and membrane-permeability. Examples are, liposome, poly-L-lysine, lipid, cholesterol, lipofectin or derivatives of these.

The dosage of an antisense oligonucleotide derivative of the present invention can be adjusted suitably according to the patient's condition and used in desired amounts. For example, a dose range of 0.1 to 100 mg/kg, preferably 0.1 to 50 mg/kg can be administered.

An antisense oligonucleotide of the invention inhibits the expression of a protein of the invention and thereby is useful for suppressing the biological activity of the protein of the invention. Also, expression-inhibitors comprising an antisense oligonucleotide of the invention are useful in that they can inhibit the biological activity of a protein of the invention. It is thought that it is possible to use an antisense oligonucleotides of this invention for the purpose of suppressing biological activities of a protein of the invention.

A protein of the invention may be used for screening compounds binding to the protein. Specifically, a protein may be used in methods of screening for compounds comprising the steps of: (1) exposing a protein of the present invention to a test sample in which a compound binding to the protein is expected to be contained; (2) detecting the binding activity of the protein to the test sample; and (3) selecting the compound having the binding activity to the protein.

A protein of the present invention to be used for screening may be a recombinant protein, a protein derived from the nature, or partial peptide thereof. Alternatively, the protein may be in a form expressed on a cell surface or in a form of cell membrane fraction. Any test sample, for example, cell extracts, cell culture supernatant, products of fermenting microorganism, extracts from marine organism, plant extracts, purified or crude proteins, peptides, non-peptide compounds, synthetic low molecular compounds and naturally occurring compounds, can be used. A protein of the present invention to be contacted with a test sample can be contacted, for example, as a purified protein, a soluble protein, a form bound to a carrier, a fusion protein with another protein, a form expressed on cell membrane, or a cell membrane fraction.

By using a protein of the present invention, for example, in a method for screening for proteins binding to the protein thereof, many methods well known by a person skilled in the art can be used. Such a screening can be conducted by, for example, the immunoprecipitation method, specifically, in the following manner. A gene encoding a protein of the present invention is expressed in a host cell, such as an animal cell, by inserting the gene into an expression vector for foreign gene, such as pSV2neo, pcDNA I, pCD8. As a promoter to be used for the expression, any promoter which can be generally used can be selected; for example, the SV40 early promoter (Rigby in Williamson (ed.), Genetic engineering, vol. 3. Academic Press, London, p. 83-141, 1982), the EF-1α promoter (Kim et al., Gene 91:217-223, 1990), the CAG promoter (Niwa et al., Gene 108:193-200, 1991), the RSV LTR promoter (Cullen Methods in Enzymology 152:684-704, 1987), the SRα promoter (Takebe et al., Mol. Cell. Biol. 8:466, 1988), the CMV immediate early promoter (Seed et al., Proc. Natl. Acad. Sci. USA 84:3365-3369, 1987), the SV40 late promoter (Gheysen et al., J. Mol. Appl. Genet. 1:385-394, 1982), the Adenovirus late promoter (Kaufman et al., Mol. Cell. Biol. 9:946, 1989), the HSV TK promoter, and so on may be used.

To express a foreign gene by introducing the gene into animal cells, the electroporation method (Chu et al., Nucl. Acid Res. 15:1311-1326, 1987), the calcium phosphate method (Chen et al., Mol Cell. Biol. 7:2745-2752, 1987), the DEAE dextran method (Lopata et al., Nucl. Acids Res. 12:5707-5717, 1984; Sussman et al., Mol. Cell. Biol. 4:1642-1643, 1985), the Lipofectin method (Derijard, Cell 7:1025-1037, 1994; Lamb et al., Nature Genetics 5:22-30, 1993;

Rabindran et al., Science 259:230-234, 1993), and such can be exemplified, and any method can be used.

A protein of the present invention can be expressed as a fusion protein comprising a recognition site (epitope) of a monoclonal antibody by introducing the epitope of the monoclonal antibody, whose property has been revealed, to N or C terminus of the protein of the present invention. A commercially available epitope-antibody system can be used (Experimental Med. 13:85-90, 1995). Through a multiple cloning site, a vector which can express a fusion protein with, for example, β-galactosidase, maltose binding protein, glutathione S-transferase, green florescence protein (GFP), is available in the market.

Methods have been reported in which fusion proteins are prepared by introducing only small epitopes comprising several to a dozen of amino acids, so that the properties of the proteins of the present invention may not change by making the proteins fusion proteins. Epitopes, for example, polyhistidine (His-tag), influenza aggregate HA, human c-myc, FLAG, Vesicular stomatitis virus glycoprotein (VSV-GP), T7 gene 10 protein (T7-tag), human simple herpes virus glycoprotein (HSV-tag), epitope such as E-tag (an epitope on monoclonal phage), and monoclonal antibodies recognizing these can be used as an epitope-antibody system for screening a protein binding to a protein of the present invention (Experimental Med. 13:85-90, 1995).

In the immunoprecipitation, an immune complex is formed by adding these antibodies to cell eluate prepared by using an appropriate detergent. This immune complex comprises a protein of the present invention, a protein having a binding affinity for the protein, and an antibody. Immunoprecipitation can be conducted by an antibody against a protein of the present invention, besides using antibodies against the above epitopes. An antibody against a protein of the present invention can be prepared, for example, by introducing a gene encoding the protein of the present invention into an appropriate $E.\ coli$ expression vector; expressing the gene in $E.\ coli$; purifying the expressed protein; and immunizing animals, for example, rabbits, mice, rats, goats, domestic fowls, and such, with such protein. The antibody can be prepared also by immunizing the above animals against a synthesized partial peptide of a protein of the present invention.

An immune complex can be precipitated, for example, by Protein A Sepharose or Protein G Sepharose when the antibody is mouse IgG antibody. When a protein of the present invention is prepared as a fusion protein with an epitope, for example GST, an immune complex can be formed by using a substance specifically binding to these epitopes, such as glutathione-Sepharose 4B, in the same manner as in the use of an antibody against a protein of the present invention.

Popular Immunoprecipitation can be performed by following or according to, for example, the reference (Harlow, E. and Lane, D.: Antibodies pp. 511-552, Cold Spring Harbor Laboratory publications, New York (1988)).

SDS-PAGE is commonly used for analysis of immunoprecipitated proteins and the binding protein can be analyzed depending on the molecular weight of the protein by using gel with an appropriate concentration. In general, because it is difficult to detect a protein binding to a protein of the present invention by a common staining method, such as Coomassie staining or silver staining, the detection sensitivity for the protein can be improved by culturing in a culture medium containing radioactive isomer, $^{35}$S-methionine or $^{35}$S-cystein, labeling proteins in the cells, and detecting the proteins. The target protein can be purified from the SDS-polyacrylamide gel and its sequence can be determined directly after the molecular weight of the protein is determined.

The present inventors have detected multiple proteins that bind to a protein of this invention by immunoprecipation in the Example (Example 4).

To isolate proteins that bind to a protein of the present invention by using the protein, for example, West western blotting (Skolnik et al., Cell 65:83-90, 1991) may be used. More specifically, it is conducted as follows: (1) constructing a cDNA library using a phage vector (λgt11, ZAP, etc.) from cells, tissues, and organs (for example, AGM region and yolk sac during early development; thymus, spleen, and liver during mid to late development, and such) that are expected to express binding proteins that bind to the protein of this invention; (2) expressing the cDNA library on LB-agarose and immobilizing the expressed protein onto a filter; (3) reacting the purified and labeled protein of this invention with the filter; and (4) detecting the plaque expressing the protein that binds to the protein of this invention by the label. Methods to label a protein of this invention may be a method that utilizes the binding characteristics of biotin and avidin; a method utilizing antibodies that bind specifically to the protein of this invention or to peptides or polypeptides fused to the protein of this invention (for example GST and such); a method that utilizes radioisotopes; a method that utilizes fluorescence; and such.

Further, another embodiment of the screening method of this invention is exemplified by a method utilizing the two-hybrid system using cells (Fields et al., Trends. Genet. 10:286-292, 1994; Dalton et al., Cell 68:597-612; "MATCHMAKER Two-Hybrid System", "Mammalian MATCHMAKER Two-Hybrid Assay Kit", "MATCHMAKER One-Hybrid System" (all manufactured by Clonetech); and "HybriZAP Two-Hybrid Vector System" (manufactured by Stratagene)). In the two-hybrid system, a protein of this invention or a partial peptide thereof may be fused to the DNA binding region of SRF or GAL4, and expressed in yeast. A cDNA library is constructed from cells predicted to express proteins that bind to the protein of this invention, wherein the cDNA library is constructed in such a way that the proteins are expressed as fusion proteins with transcription activation regions of VP16 or GAL4. The cDNA library is transfected into the above yeast, and then positive clones are detected to isolate the cDNA derived from the library (expression of a protein that binds to the protein of the invention in yeast leads to the binding of the two proteins, and results in the activation of the reporter gene, which allows to detect positive clones). The protein encoded by the isolated cDNA may be obtained by introducing the cDNA into $E.\ coli$ and expressing it therein. Thus, it is possible to prepare proteins that bind to a protein of this invention and genes encoding them. The reporter gene used in the two-hybrid system may be such as Ade2 gene, Lac Z gene, CAT gene, luciferase gene, PAI-1 (Plasminogen activator inhibitor type 1) gene, and such besides HIS3 gene, but are not limited to these examples.

A protein binding to a protein of the present invention can be screened using affinity chromatography. For example, a preferred method for screening of the present invention utilizes affinity chromatography. A protein of the invention is immobilized on a carrier of an affinity column, and a test sample, in which a protein capable of binding to the protein of the invention is supposed to be expressed, is applied to the column. A test sample herein may be, for example, cell extracts, cell lysates, etc. After loading the test sample, the column is washed, and proteins bound to the protein of the invention can be prepared.

The amino acid sequence of the obtained protein is analyzed, an oligo DNA was synthesized based on the sequence, and cDNA libraries are screened using the DNA as a probe to obtain a DNA encoding the protein.

A biosensor using the Surface Plasmon Resonance phenomenon may be used as a means for detecting or quantifying the bound compound in the present invention. When such a biosensor is used, the interaction between a protein of the invention and a test compound can be observed in real-time as a surface plasmon resonance signal, using only a minute amount of proteins without labeling (for example, BIAcore, Pharmacia). Therefore, it is possible to evaluate the binding between a protein of the invention and a test compound using a biosensor such as BIAcore.

Methods of screening molecules that bind when an immobilized protein of the present invention is exposed to synthetic chemical compounds, natural substance banks, or a random phage peptide display library, and methods of screening using high-throughput based on combinatorial chemistry techniques (Wrighton et al., Science 273:458-64, 1996; Verdine, Nature 384:11-13, 1996; Hogan, Jr., Nature 384:17-9, 1996) are well known to those skilled in the art as methods for isolating not only proteins but also chemical compounds that bind to a protein of the present invention (including agonist and antagonist).

Compounds that bind to a protein of this invention serve as drug candidates for promoting or inhibiting the activity of the protein of this invention, and may be applied to treatment of diseases caused by expressional or functional abnormalities of the protein of this invention, or diseases that may be treated by regulating the activity of the protein of this invention. Compounds obtained by using the screening method of this invention, wherein the structure of compounds having binding activity toward a protein of this invention is partially altered by addition, deletion, and/or replacement, are also included as compounds that bind to a protein of this invention.

When a compound binding to a protein of the present invention is used as a pharmaceutical for humans and other mammals, such as, mice, rats, guinea pigs, rabbits, chicken, cats, dogs, sheep, pigs, bovines, monkeys, baboons, chimpanzees, the isolated compound can be administered not only directly, but also as dosage forms using known pharmaceutical preparation methods. For example, according to the need, the drugs can be taken orally as sugarcoated tablets, capsules, elixirs and microcapsules; or non-orally in the form of injections of sterile solutions or suspensions with water or any other pharmaceutically acceptable liquid. For example, the compounds can be mixed with pharmacologically acceptable carriers or medium, specifically, sterilized water, physiological saline, plant-oil, emulsifiers, suspending agent, surface-active agent, stabilizers, flavoring agents, excipients, vehicles, preservatives and binders, into a unit dose form required for generally accepted drug implementation. The amount of active ingredient in these preparations makes a suitable dosage within the indicated range acquirable.

Examples of additives which can be mixed to tablets and capsules are, binders such as gelatin, corn starch, tragacanth gum and gum acacia; excipients such as crystalline cellulose; swelling agents such as corn starch, gelatin and alginic acid; lubricants such as magnesium stearate; sweeteners such as sucrose, lactose or saccharin; flavoring agents such as peppermint, *Gaultheria adenothrix* oil and cherry. When the unit dosage form is a capsule, a liquid carrier such as oil can also be included in the above ingredients. Sterile composites for injection can be formulated following normal drug implementations using vehicles such as distilled water used for injections.

Physiological saline, glucose, and other isotonic liquids including adjuvants, such as D-sorbitol, D-mannose, D-mannitol, and sodium chloride, can be used as aqueous solutions for injections. These can be used in conjunction with suitable solubilizers, such as alcohol, specifically ethanol; polyalcohols such as propylene glycol and polyethylene glycol; and non-ionic surfactants such as Polysorbate 80™ and HCO-50.

Sesame oil or Soy-bean oil can be used as a oleaginous liquid and may be used in conjunction with benzyl benzoate or benzyl alcohol as solubilizers; they further may be formulated with a buffer such as phosphate buffer and sodium acetate buffer, a pain-killer such as procaine hydrochloride, a stabilizer such as benzyl alcohol and phenol, and an antioxidant. The prepared injection may be filled into a suitable ampule.

Methods well known to one skilled in the art may be used to administer the pharmaceutical compounds of the present invention to patients, for example as intraarterial, intravenous, percutaneous injections and also as intranasal, transbronchial, intramuscular percutaneous, or oral administrations. The dosage varies according to the body-weight and age of a patient and the administration method, but one skilled in the art can suitably select them. If the compound can be encoded by a DNA, the DNA can be inserted into a vector for gene therapy to perform the therapy. The dosage and method of administration vary according to the body-weight, age, and symptoms of a patient, but one skilled in the art can select them suitably.

Although there are some differences according to the symptoms, the dose of a compound that binds with a transcriptional regulatory factor of the present invention and inhibits its activity is about 0.1 mg to about 100 mg per day, preferably about 1.0 mg to about 50 mg per day and more preferably about 1.0 mg to about 20 mg per day, when administered orally to a normal adult (weight 60 kg).

When administering parenterally in the form of an injection to a normal adult (weight 60 kg), although there are some differences according to the patient, target organ, symptoms and method of administration, it is convenient to intravenously inject a dose of about 0.01 mg to about 30 mg per day, preferably about 0.1 to about 20 mg per day and more preferably about 0.1 to about 10 mg per day. Also, in the case of other animals too, it is possible to administer an amount converted to 60 kgs of body-weight or an amount converted to body surface.

All publications and patents cited herein are incorporated by reference in their entirety.

DESCRIPTION OF DRAWINGS

FIG. 3 depicts photographs demonstrating the result of electrophoresis showing the result of analyzing YS68 expression by RT-PCR in the yolk sac at each stage of a developing embryo.

FIG. 4 depicts photographs demonstrating the result of electrophoresis showing the result of analyzing YS68 expression by RT-PCR in the AGM region at each stage of a developing embryo is shown in (A); and in (B) the E10.5 AGM region was cultivated in the presence or absence of oncostatin M (OSM), and RNA was prepared on the 5th day of cultivation. Expression of YS 68 was then compared to those of uncultivated AGM region by RT-PCR.

FIG. 8 depicts a comparison of the amino acid sequences between human (SEQ ID NO: 14) and mouse YS68 fSEQ ID NO: 12).

FIG. 11 depicts photographs showing the result of immunostaining of YS68 in tissues. The dorsal aorta (A, B, C, D, and E), the umbilical artery (F) of an E11.5 mouse; and the blood vessels within an E9 yolk sac (H) were stained with erythroid marker TER119 (A, B, and G) and with anti-YS68 antibody (C, D, E, and H). B and D are enlargements of A and C, respectively, and E shows a different view of the aorta. The site where the hematocyte is budding from the vascular endothelium is indicated by an arrow.

FIG. 13 depicts photographs showing the result of investigation on the expression of YS68 in hematocytes isolated from E14 liver. The Giemsa stained hematocytes of the liver (A); hematocytes of the E14.5 liver (B); CD34 negative cells (C); and CD34 positive cells (D) were stained with anti-YS68 antibodies. Whether the sorted cells are CD34 positive or not was confirmed (E-H). E-F and G-H are taken from the same views, E and G are fluorescence photographs, and F and H are visual photographs. Most of the cells sorted by CD34 were weakly CD34 positive to strongly positive (E and F). Cells that passed through the CD34 column were hardly expressing any CD34 (G and H).

DETAILED DESCRIPTION

The present invention will be described specifically by way of examples below, however this invention is not restricted in any way to these examples.

Example 1

Isolation of YS68 Gene

To obtain molecules that are expressed specifically in hemangioblasts, an experiment was carried out in which cDNA of an E14 yolk sac was subtracted from the cDNA of an E9 yolk sac. Poly A RNAs were purified from each of the E9 and E14 yolk sacs, respectively; then PCR-Select cDNA Subtraction Kit (Clonetech) was used for the subtraction. The obtained cDNA fragments were subcloned into pGEM-T vectors (Promega), and then, after selecting highly expressed cDNAs in E9 yolk sacs by dot blotting, selected cDNA were sequenced. The clone #68 was a novel gene fragment that was not registered in the database. Thus, a primer was designed from the sequence of this gene fragment, and using mouse 15-day Embryo Marathon-Ready cDNA (Clonetech) as a template, a full-length cDNA was isolated by the 5'-RACE method. Mouse YS68 encodes 1,265 amino acids, but is expected to have further upstream sequence.

Figure 1:
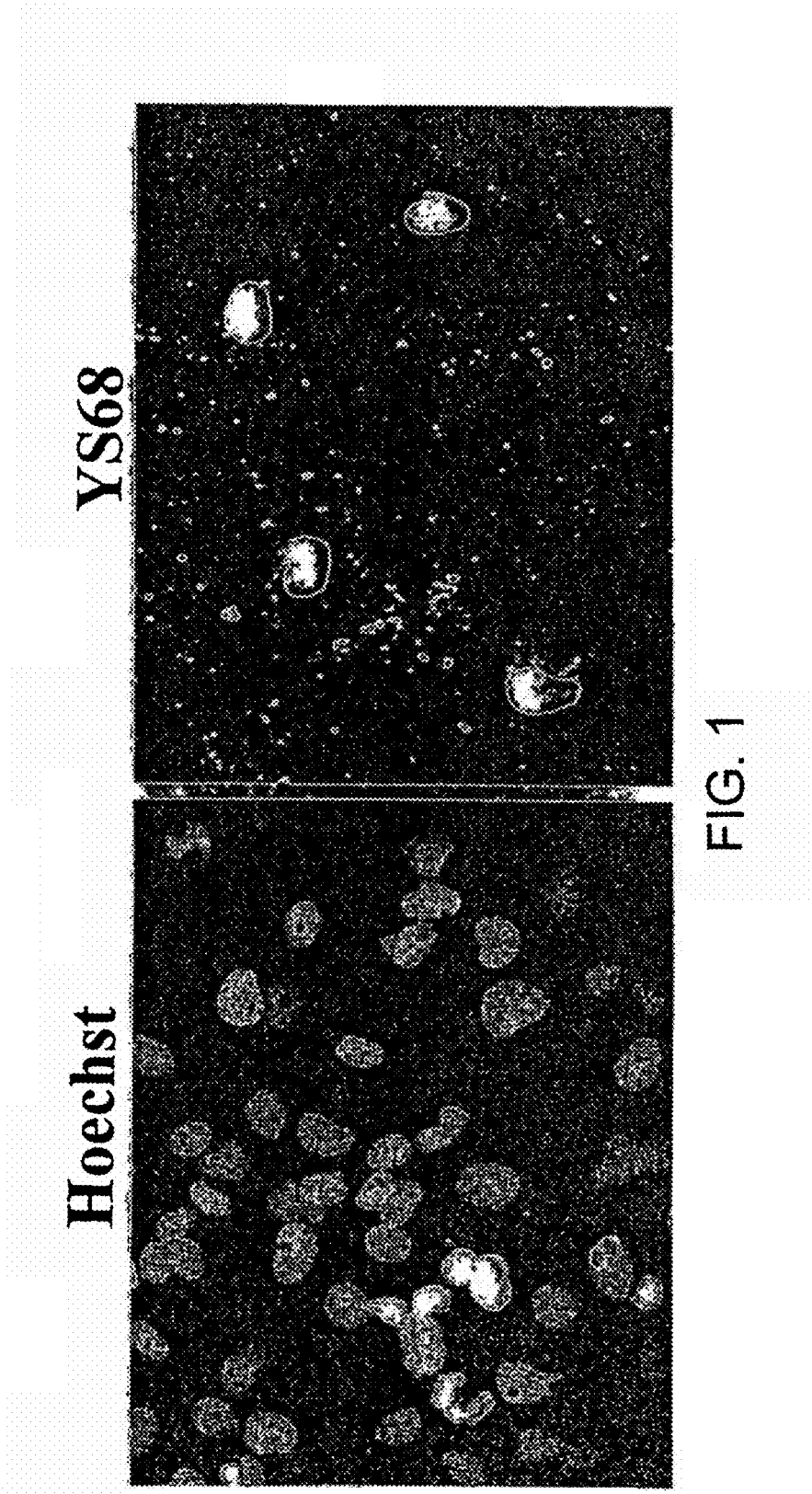
FIG. 1 depicts photomicrographs indicating the localization of YS68 within cells. YS68 tagged with a flag epitope is expressed in COS7 cells, and upon staining with anti-Flag antibodies, the expression sites of YS68 were investigated (right). In addition, the same cells were treated with Hoechst to selectively stain the nucleus (left).

The obtained YS68 did not have a characteristic motif within its amino acid sequence. However, existence of multiple nuclear transport signals was confirmed. Consequently, YS68 was anticipated to be a protein that functions in the nucleus. Therefore, to confirm the hypothesis, a vector (pEF-BOSE-Flag (Nakashima et al., FEBS Let. 403:79-82, 1997) that expresses the mouse YS68 protein (1265 amino acids) tagged with Flag was transfected to COS7 cells. After 24 hours, the cells were fixed with 4% formalin, and was treated with 0.1% Triton-X 100. Then, this was reacted with anti-Flag antibodies, followed by FITC-labeled anti-mouse IgG, and was observed through a fluorescence microscope. Consequently, expression of YS68 was strong in the nucleus, as expected (FIG. 1). Since the cell nucleus is the site where DNA transcription occurs, YS68 is anticipated to be a transcription factor involved with DNA transcription.

Figure 8:
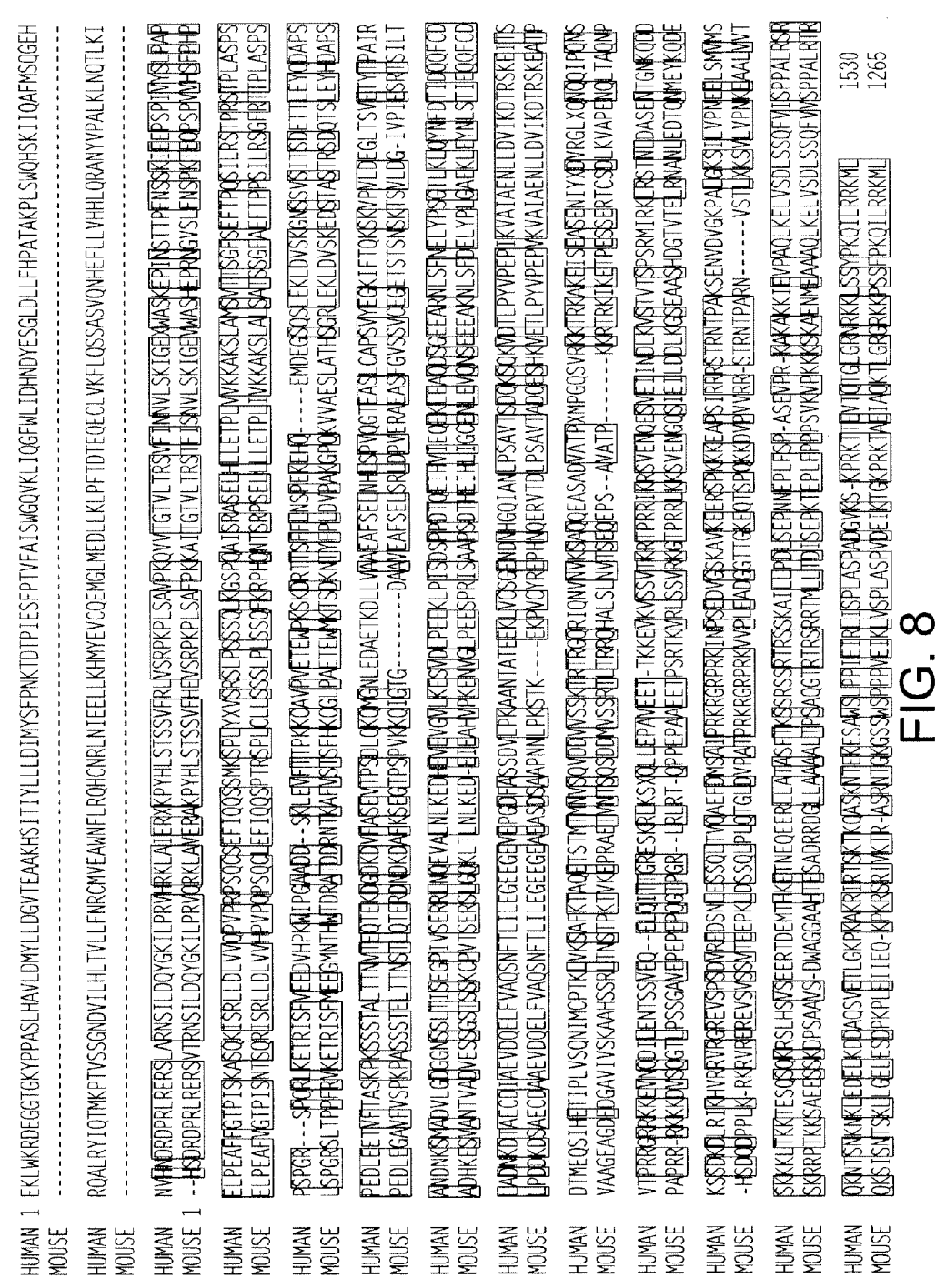

Human YS68 gene was isolated by 5'-RACE and 3'-RACE by designing a primer based on the genetic sequence of mouse YS68. More specifically, based on the genetic sequence of mouse YS68, EST fragments that are thought to be YS68 homologues in humans were searched in the EST database. Primers were designed based on this EST fragment, and using human fetal liver Marathon-Ready cDNA (Clonetech) as a template, the 5' region and the 3' region cDNA were isolated by 5'-RACE and 3'-RACE according to the instructed procedure. The isolated cDNA nucleotide sequence is described in SEQ ID NO:11, and the amino acid sequence of the protein encoded by this cDNA is described in SEQ ID NO:12. A comparison of human and mouse YS68 amino acid sequences is shown in FIG. 8.

Example 2

Expression Pattern Analysis of YS68

The expression distribution of YS68 within tissues was analyzed by Northern blotting. Total RNA was prepared from each tissues of embryonic or adult mice using ISOGEN (Wako). 25 µg/lane of these samples were electrophoresed. After blotting onto a nylon membrane, hybridization was performed with YS68 cDNA fragments labeled with $^{32}$P. Hybridization was performed in ExpressHyb solution (Clonetech) at 68° C. for 2 hours; then, after several washings with 2×SSC and 0.1% SDS at room temperature, followed by several washings with 0.1×SSC and 0.1% SDS at 65° C., autoradiography was performed.

Figure 2:
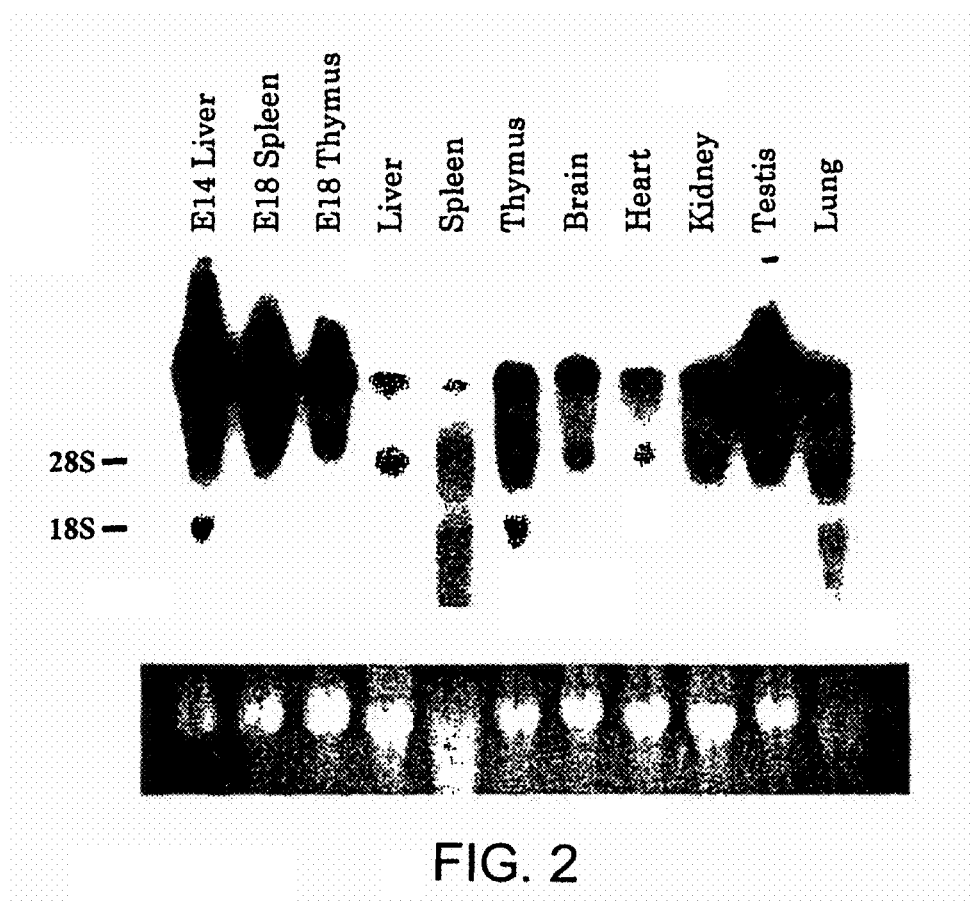
FIG. 2 depicts photographs demonstrating the result of electrophoresis showing the expression distribution of YS68 in tissues. RNA was prepared from liver, thymus, or spleen tissues of an embryonic day 14 (E14) or embryonic day 18 (E18) mouse embryo, respectively, or from the tissues of an adult mouse to perform Northern hybridization. The lower panel shows 18S ribosomal RNA before blotting as a control.

The expression of YS68 in adult tissue was the strongest in testis, followed those in kidney and lung. Observation of YS68 expression in hematopoietic tissues showed that expression was very strong in liver, thymus and spleen that function as hematopoietic tissues during the embryonic stage. However, expression in these tissues rapidly decreased or was absent in those of adult (FIG. 2).

Further, the expression pattern in tissues known to be involved in primitive hematopoiesis was investigated in detail. The site of hematopoiesis is known to shift during the embryonic stage as described below from previous studies. First, primitive hematopoiesis starts in the yolk sac at E8, and definitive hematopoiesis begins later in the AGM region at E10.5. Hematocytes that developed in AGM are immediately transported to liver that is formed around E11.5, then differentiate and proliferate at this site until immediately after birth. Meanwhile, hematopoiesis begins to take place in thymus and spleen that are formed around E16.5. After birth, the site of hematopoiesis changes to bone marrow. Based on these facts, the expression pattern of YS68 in these tissues was analyzed in further detail by RT-PCR. Total RNA was extracted from each tissue of mouse embryos at each developmental stage, or an adult mouse; and 1 µg of each total RNA was reverse transcribed to cDNA using SUPERSCRIPT II preamplification system (Gibco). This was used as a template and a YS68-specific primer (68•3: 5'-CACCCGTGAAGAAACAAAT-AGGCA-3'/SEQ ID NO:3, 68•4: 5'-CCTTTGGTACATGAGCTTCTATTT-5'/SEQ ID NO:4) or a G3PDH-specific primer was used to perform PCR (25 cycles of 94° C. for 30 seconds, 62° C. for 30 seconds, and 72° C. for 30 seconds). Then was electrophoresed on 1% agarose gel, and the gel was stained with ethidium bromide.

Figure 5:
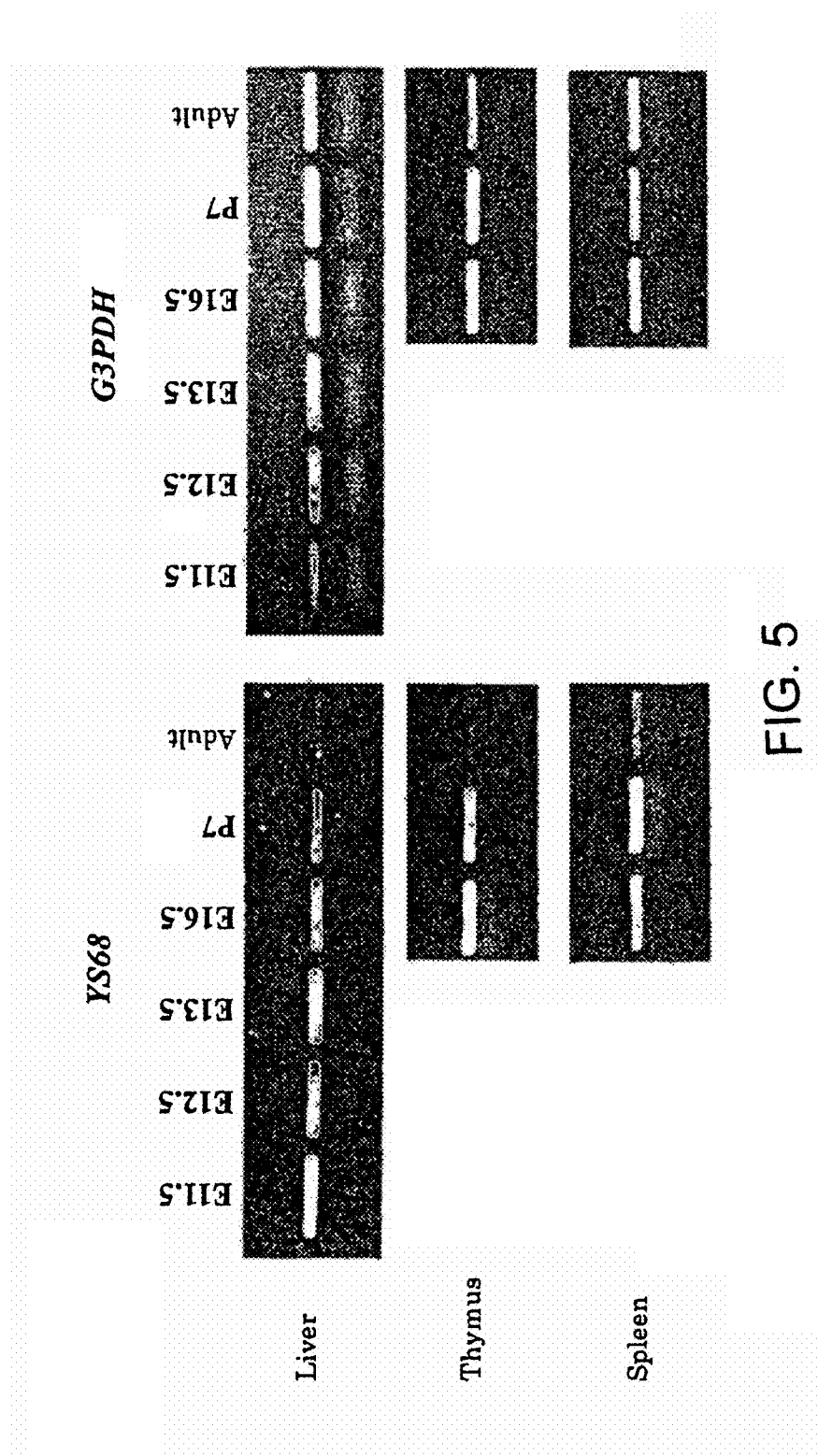
FIG. 5 depicts photographs demonstrating the result of electrophoresis showing the result of comparison of the expression level of YS68 by RT-PCR upon extraction of RNA from liver, thymus and spleen of embryonic (E11.5 to E16.5), 7-day-old, and adult mice, respectively.

Expression of YS68 decreased gradually in the yolk sac, as development proceeded (FIG. 3). Against expectations, expression of YS68 was low in the AGM region at E10.5, when definitive hematopoiesis begins (FIG. 5A). On the other hand, in liver, thymus, and spleen known to function as sites for hematopoiesis in the embryonic stage, expression of YS68 was very high (FIG. 4) and correlated to the period when these tissues function as hematopoietic organs.

Furthermore, the expression distribution of YS68 in mouse embryo was analyzed by in situ hybridization. A vector constructed by inserting a 545 by cDNA of the 5'-region of YS68 (positions 898 to 1443) into pBluescript II was used as a template to perform in vitro transcription using T7 RNA polymerase or T3 RNA polymerase (Boeringer Mannheim), and to synthesize sense or antisense $^{35}$S-labeled RNA, respectively. The mouse embryo was removed and frozen to produce slices using a cryostat. After immobilization and acetylation with 4% paraformaldehyde/PBT, hybridization was performed overnight at 55° C. with the above-mentioned RNA probe. After treating the reaction solution with RNase A, it was washed several times and autoradiography was performed.

Figure 6A:
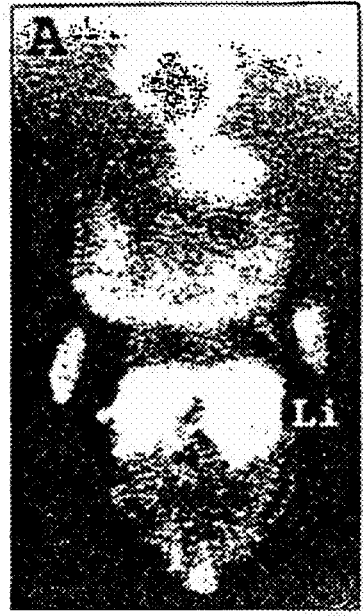
FIG. 6 depicts photographs showing the result of in situ hybridization on slices prepared from an E11.5 embryo. A is an autoradiogram, and B is an image obtained by staining the same slice by hematoxylin. Li: liver.
Figure 6B:
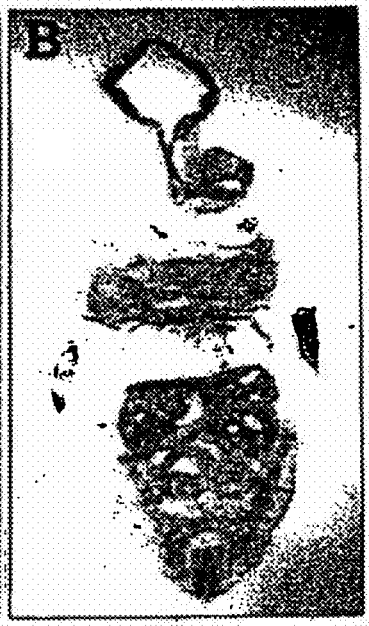
Figure 7A:
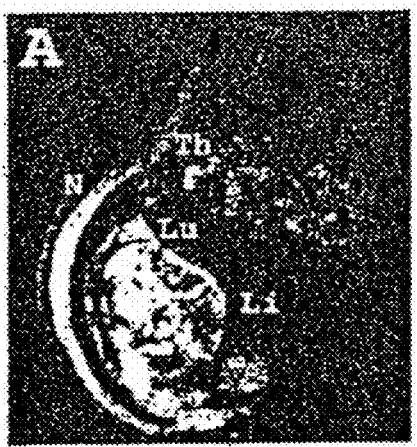
FIG. 7 depicts photographs showing the result of in situ hybridization on slices prepared from an E14.5 embryo. A and C are autoradiograms, while B and D are images obtained by staining the same slices by hematoxylin. Li: liver, Lu: lung, Th: thymus, and N: neural tube.
Figure 7B:
Figure 7C:
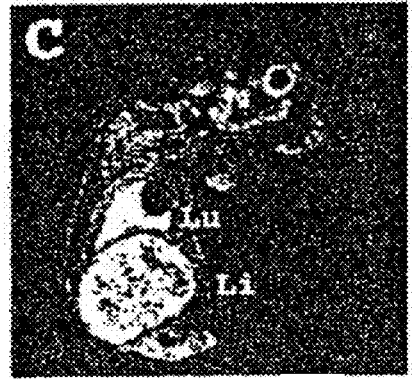
Figure 7D:
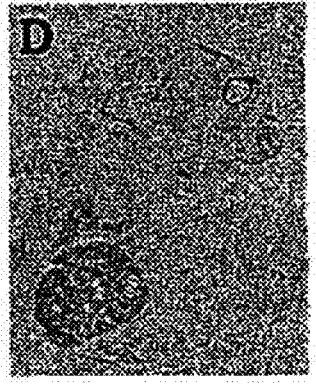

The expression of YS68 was the strongest in liver at E11.5 (FIG. 6). YS68 was mainly strongly expressed in liver and in the developing thymus, and expression was also confirmed in lungs and neural tube at E14.5 (FIG. 7).

These results indicate that the expression of YS68 is localized in tissues where active hematopoiesis takes place in a period-specific manner, and strongly suggests that YS68 is a molecule involved in primitive hematopoiesis. Its expression was low in the E10.5 AGM region, which is thought to be the site of development for hematopoietic cells. However this may be due to the absolute number of cells involved in hematopoiesis within the entire AGM region, which is not so high. In fact, Suda et al. revealed that the percentage of hemangioblasts in the AGM region at E10.5 is 5% or less using TEK as a marker for hemangioblasts (Hamaguchi et al., Blood 93:1549-1556, 1999). On the other hand, when E10.5 AGM region is dispersed and cultivated on a dish, the emergence of hematocytes can be confirmed around the 5th day of cultivation (Mukouyama et al., Immunity 8:105-114, 1998). Interestingly, the expression of YS68 had increased in AGM derived cells cultivated for 5 days (FIG. 4B). According to these results, the expression of YS68 is expected to rise in cells that have acquired hematopoietic ability, or in immature hematocytes.

Example 3

Full-Length Cloning of Mouse and Human YS68

Using primers constructed from the YS68 gene sequence obtained so far, 5'-RACE was performed using the mouse 15-day Embryo Marathon-Ready cDNA and human fetal liver Marathon-Ready cDNA (Clonetech) as templates, to clone the upstream 5' region of mouse and human YS68 gene. Full-length human and mouse cDNA sequences were determined by repeating this 5'-RACE protocol.

Figure 9:
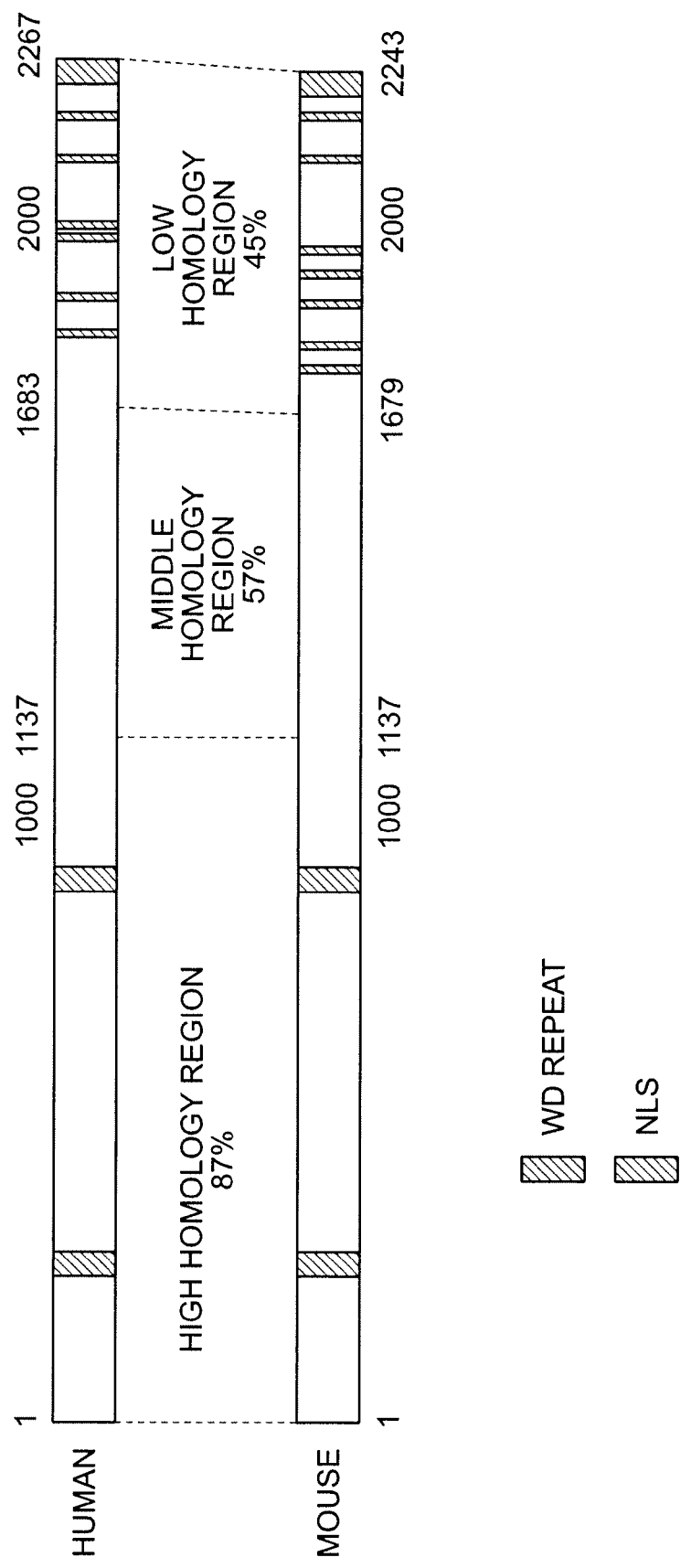
FIG. 9 depicts the comparison of the amino acid structures of human and mouse YS68.

Consequently, human and mouse YS68 (SEQ ID NOs: 14 and 12, respectively) were anticipated to encode 2,266 and 2,243 amino acids, respectively (FIG. 9). Comparing the human (SEQ ID NO: 14) and mouse (SEQ ID NO: 12) amino acid sequences, interestingly, the N-terminal region (human 1-1137 of SEQ ID NO: 14, mouse 1-1137 of SEQ ID NO: 12) had a very high homology of 87%, whereas the homology in the central region (human 1138-1683 of SEQ ID NO: 14, mouse 1138-1679 of SEQ ID NO: 12) was 57%, and that in the C-terminal region (human 1684-2266 of SEQ ID NO: 14, mouse 1680-2243 of SEQ ID NO: 12) was very low, showing a homology of 45%. In the C-terminal region with low homology, many nuclear transport signals existed. On the other hand, in the N-terminal region with high homology, two WD repeats existed, which repeats are known to be necessary for interaction among proteins. Since the homology in this region is very high between humans and mice, this region is anticipated to be important for the function of YS68.

Example 4

Proteins Binding to YS68

It was expected that YS68 is bound to some protein in vivo because a protein-binding site (WD repeats) exists in the N-terminal region of YS68. Therefore, cell lysate was prepared from cultivated cells of embryonic liver and immunoprecipitation with anti-YS68 antibody was performed. Then, SDS polyacrylamide gel electrophoresis was performed to investigate whether a protein that coprecipitates with YS68 exists. Specifically, cultivated mouse liver cells at E14.5 were solubilized with lysis buffer (0.5% NP-40, 10 mM Tris-HCl pH7.6, 150 mM NaCl, 5 mM EDTA, 2 mM $Na_3VO_4$, 1 mM phenylmethylsulfonyl fluoride, and 5 µg/ml aprotinin). After incubation overnight at 4° C. with anti-YS68 antibodies, protein G was added and was further incubated for 1 hour. SDS polyacrylamide gel electrophoresis was conducted after immunoprecipitation, and the gel was stained with silver.

Figure 10:
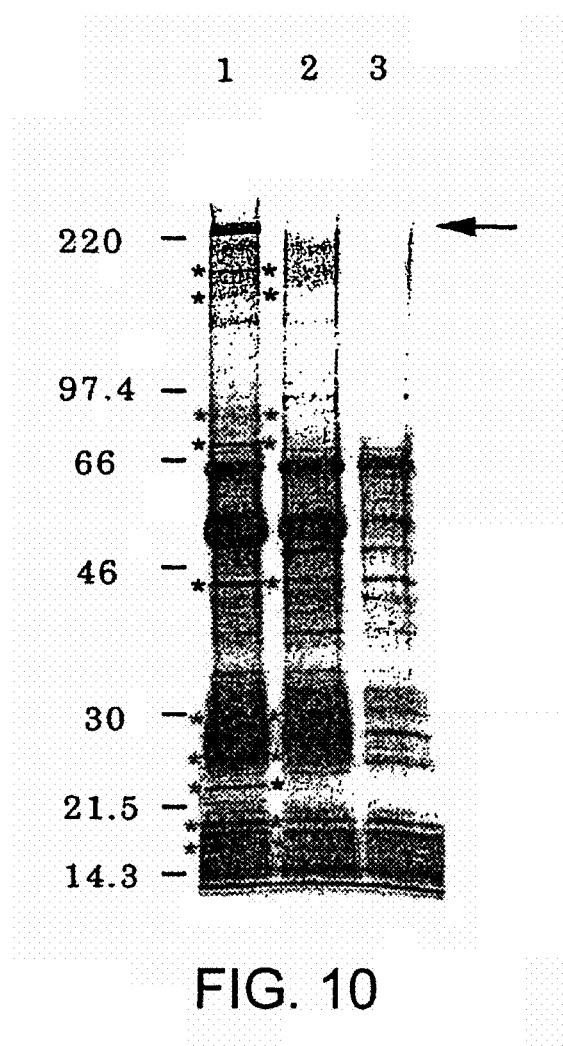
FIG. 10 depicts a photograph showing the result of analysis on proteins that coprecipitate with YS68. After primary cultivation of E14.5 liver, cell lysate was prepared. Then, the lysate was subjected to immunoprecipitation with anti-YS68 antibody and protein A (Lane 1), rabbit IgG and protein A (Lane 2), and protein A alone (Lane 3). Following SDS-PAGE, the gel was visualized by silver staining. Arrow: YS68; and *: protein that coprecipitated with YS68.

Consequently, existence of multiple molecules that coprecipitate with YS68 within cells of embryonic liver was confirmed (FIG. 10). This suggested that YS68 functions by binding to several types of proteins within the cell.

Example 5

Expression Site of YS68 within Tissues

For detailed analysis of the YS68 expression site, the YS68 protein was used to immunize rabbits to produce polyclonal antibodies against YS68. The protein encoding the 1208-1482 amino acid region of mouse YS68 was expressed in *E. coli*, was purified according to standard procedures, and was used as the antigen in the production of YS68 polyclonal antibodies. Immunization was carried out on rabbits (New Zealand White, 2.5 kg, female) using 200 µg antigen for 1 immunization, with an interval of 10 days for 4 immunizations. Then upon collection of whole blood, antiserum was obtained. Furthermore, an affinity column with immobilized antigens was prepared, and anti-YS68 polyclonal antibodies were purified from the antiserum.

Using these antibodies, the expression site in the AGM region of E11.5 embryo was investigated by immunostaining. Immunostaining was conducted as follows. First, slices of frozen mouse embryo were prepared using a cryostat (Leica). This was immobilized with 4% formaldehyde and was treated with methanol. After treatment with 0.3% aqueous hydrogen peroxide, blocking was carried out with 3% BSA, then upon reaction with primary antibodies overnight at 4° C. and with secondary antibodies (HRP-labeled anti-rabbit IgG) at room temperature for 1 hour, washing was repeated 3 times with PBS, and visualization was accomplished by the addition of substrate (Metal Enhanced DAB substrate kit, Pierce).

Consequently, the hematocytes existing in the endothelium were stained using red blood cell marker TER119 (used as a control; FIG. 11A, B), whereas, the vascular endothelium was stained specifically using anti-YS68 antibody (FIGS. 11C, D, and E). Interestingly, YS68 was darkly stained in the hematocytes emerging from the endothelium cells (FIG. 11E, arrow). In addition, strong expression of YS68 was indicated in the vascular endothelium of the umbilical vein (FIG. 11F). In contrast to TER119, which selectively stained hematocytes in the blood vessel, YS68 expression was stronger in vascular endothelium than in hematocytes in E9.5 yolk sacs (FIGS. 11G and H).

Example 6

Expression of YS68 within Cells

A liver was surgically removed from an embryo (E14.5), cut into small pieces with tweezers, and incubated in cell dissociation buffer (Gibco) at 37° C. for 30 minutes. The cells were further treated with 0.1% collagenase at 37° C. for 1 hour, and were loosened by pipetting. After washing several times with PBS, the cells were suspended in DMEM containing 10% FCS, and were cultivated on a 10-cm dish.

To investigate the localization of endogenous YS68 within cells, cultured hepatic cells were stained with anti-YS68 antibodies. First, the cells were fixed with 4% formalin, and then treated with 0.1% Triton-X 100 for cell staining. Next, cells were reacted with the primary antibodies, and then with secondary antibodies. The cells were visualized in the same manner as in Example 5.

Figure 12A:
FIG. 12 depicts photographs showing the result of staining primary culture cells of E14.5 liver with anti-YS68 antibodies (A), or with rabbit IgG (B). The expression of YS 68 was strong at the nucleus and around the nucleus.
Figure 12B:

Consequently, although YS68 has multiple nuclear transport signals, strong expression was found not only in the nucleus, but also around the nucleus, which expression depended on cells (FIG. 12). Next, similar analysis for the expression in hematocytes was carried out. YS68 expression in hematocytes separated from embryonic liver was found to have varied strengths of expression depending on the cell type (FIG. 13B).

Therefore, the group of hematocytes was sorted using CD34, which is a marker for immature hematocytes, and YS68 expression in CD34-positive cells was investigated. To collect CD34-positive cells, embryonic liver (E14.5) was incubated in a dissociation buffer at 37° C. for 30 minutes, and then the cells were dissociated by pipetting in PBS. After passing through a nylon mesh filter (Falcon), the cells were suspended in a sample buffer (0.5% BSA, 2 mM EDTA in PBS). The cells were reacted with biotin labeled anti-CD34 antibodies (Pharmingen), followed by FITC labeled streptavidin at 4° C., and then were incubated with anti-FITC microbeads. CD34 positive cells were eluted using MACS (Magnetic Cell Sorting) column according to the instructed protocol. The cells were centrifuged on a slide glass at 400 rpm for 5 minutes to fix them onto the slide glass. Cell staining was performed in the same manner as described above.

Consequently, hematocytes that were concentrated using anti-CD34 antibodies (FIG. 12D) showed a higher expression of YS68 compared to hematocytes that passed through the CD34 column (FIG. 12C). Therefore, YS68 expression is anticipated in less differentiated CD34 positive hematocytes.

Example 7

Localization of Each Domain of YS68 within Cells

Using cDNA prepared from mouse embryonic liver as a template, cDNA encoding the N-terminal region (amino acids 5-1148) and C-terminal region (amino acids 981-2243) of mouse YS68 (SEQ ID NO: 12) were amplified by PCR. The amplified cDNAs were inserted downstream of the Flag region of animal cell expression vector pEFBOSE-F to produce pEFBOSE-F-YS68(5-1148) and pEFBOSE-F-YS68 (981-2243) that expresses the N-terminal region of YS68 and the C-terminal region of YS68 (SEQ ID NO: 12), respectively. The expression vectors were then transfected into COS-7 cells using lipofectamine 2000 (Gibco), and 24 hours later, the cells were immobilized with methanol. To investigate the localizations of each YS68 expressed within the cells, the cells were reacted with anti-Flag antibody, followed by peroxidase-labeled anti-mouse IgG, and finally substrate was added for visualization.

Figure 14:
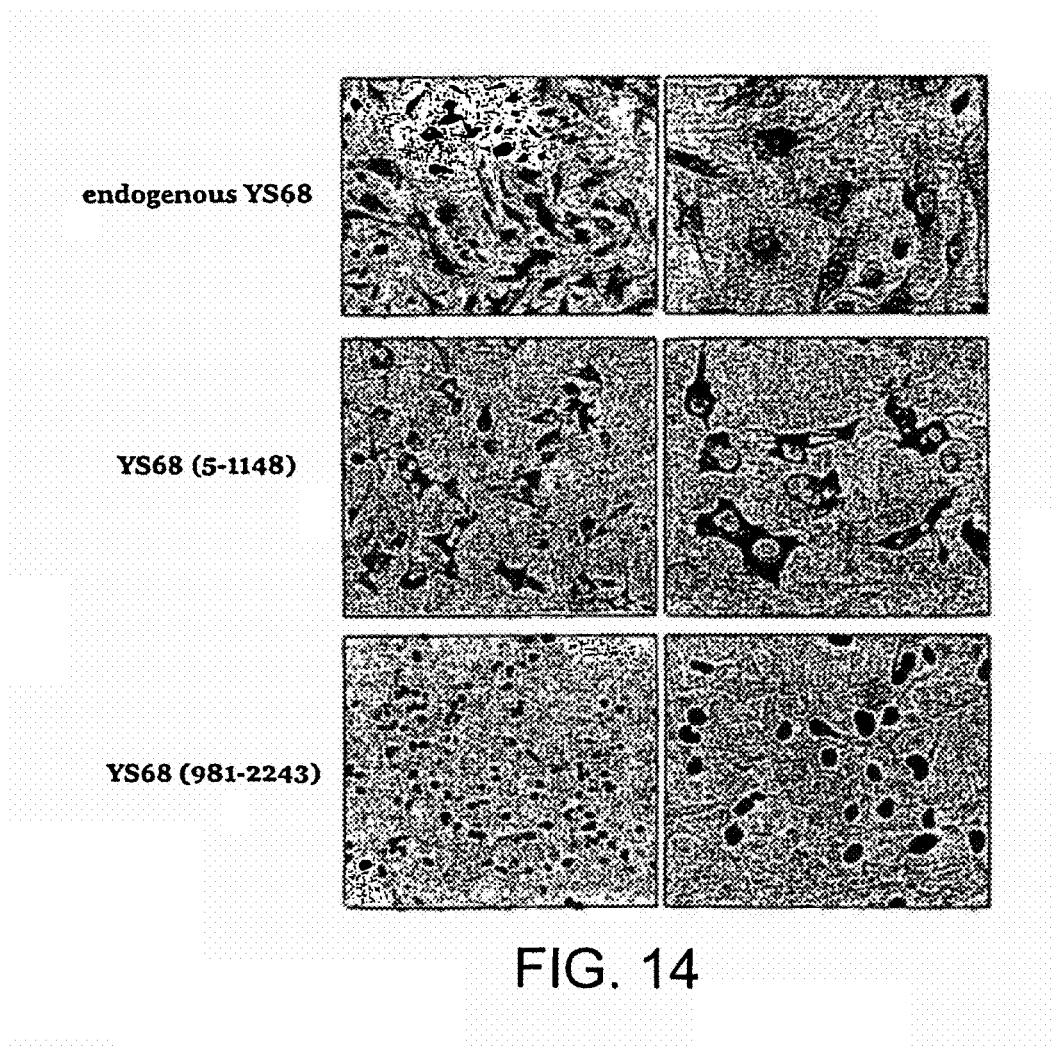
FIG. 14 depicts photographs showing the localization of YS68 within cells. A slightly magnified photograph is shown on the left, and a largely magnified photograph is shown on the right. Cells derived from fetal liver were stained with anti-YS68 antibodies to investigate endogenous expression sites of YS68 (top row). In addition, pEFBOSE-F-YS68 (5-1148) that expresses the N-terminal region of YS68 (middle row), or pEFBOSE-F-YS68 (981-2243) that expresses the C-terminal region of YS68 (bottom row) were transfected to COS7 cells, and these cells were stained with anti-Flag antigens to investigate the localization within the cell.

Due to the multiple nuclear transport signals in the YS68 C-terminal region (FIG. 9), localization of YS68 in the nucleus was anticipated; however, endogenous YS68 was localized not only in the nucleus but also around the nucleus (FIG. 12). Additionally, constructs lacking the YS68 N-terminal region or the C-terminal region were prepared and were expressed in COS cells, and their localizations were investigated. The results confirmed that YS68 lacking the C-terminal region had strong tendency to localize in the cytoplasm, and YS68 lacking the N-terminal region in the nucleus (FIG. 14). These results suggested the possibility that the N-terminal region is inhibiting the transfer of YS68 into the nucleus. Since two WD repeats necessary for protein interaction exist in the N-terminal region, it was speculated that binding of this region to some molecule might possibly inhibit the transfer into the nucleus.

INDUSTRIAL APPLICABILITY

The present invention provides novel "YS68" proteins predicted to be involved in primitive hematopoiesis and genes encoding the proteins. The genes may be utilized as markers for hematopoietic cells involved in primitive hematopoiesis and as factors regulating hematopoiesis. In addition, they may be utilized for purification and cloning of new factors involved in hematopoiesis, and even as tools for drug development for various diseases arising due to abnormalities in expression of the genes of this invention caused by abnormalities in expression regulation in vivo. Further, the "YS68" genes of this invention may be involved in blood tumors. Therefore, drug development against tumors utilizing the proteins of this invention is anticipated. By designing medicaments that target the genes of this invention, development of drugs that have new mechanisms of action may be enabled. Proteins and genes derived from humans are especially preferred in drug development compared to those derived from other organisms

What is claimed is:

1. A purified polypeptide comprising the amino acid sequence of SEQ ID NO:14.

2. The polypeptide of claim 1, wherein the polypeptide consists of the amino acid sequence of SEQ ID NO: 14.

3. The polypeptide of claim 1, wherein the polypeptide comprises the amino acid sequence encoded by position 98 to 6922 of the nucleic acid sequence of SEQ ID NO: 15.

4. The polypeptide of claim 1, wherein the polypeptide comprises the amino acid sequence of SEQ ID NO: 14 fused to a peptide or protein selected from the group consisting of FLAG, 6×His, 10×His, Influenza agglutinin (HA), human c-myc fragment, VSV-GP fragment, p18HIV fragment, T7-tag, HSV-tag, E-tag, SV40T antigen fragment, lck tag, α-tubulin fragment, B-tag, Protein C fragment, GST (glutathione-S-transferase), immunoglobulin constant region, β-galactosidase and MBP (maltose-binding protein).

5. A purified polypeptide comprising a fragment of the amino acid sequence of SEQ ID NO:14, wherein the fragment is at least 10% of the length of the sequence of SEQ ID NO: 14.

6. The polypeptide of claim 5, wherein the fragment of the amino acid sequence of SEQ ID NO: 14 is fused to a peptide or protein selected from the group consisting of FLAG, 6×His, 10×His, Influenza HA, human c-myc fragment, VSV-GP fragment, p18HIV fragment, T7-tag, HSV-tag, E-tag, SV40T antigen fragment, lck tag, α-tubulin fragment, B-tag, Protein C fragment, GST, immunoglobulin constant region, β-galactosidase and MBP.

7. A purified polypeptide comprising the amino acid sequence from position 1 to 1137 of SEQ ID NO: 14.

8. The polypeptide of claim 7, wherein the polypeptide consists of a fragment of the sequence of SEQ ID NO: 14, the fragment comprising the amino acid sequence from position 1 to 1137 of SEQ ID NO: 14.

9. The polypeptide of claim 7, wherein the polypeptide comprises the amino acid sequence from position 1 to 1137 of SEQ ID NO: 14 fused to a peptide or protein selected from the group consisting of FLAG, 6×His, 10×His, Influenza HA, human c-myc fragment, VSV-GP fragment, p18HIV fragment, T7-tag, HSV-tag, E-tag, SV40T antigen fragment, lck tag, α-tubulin fragment, B-tag, Protein C fragment, GST, immunoglobulin constant region, β-galactosidase and MBP.

10. A purified polypeptide comprising the amino acid sequence from position 1684 to 2266 of SEQ ID NO: 14.

11. The polypeptide of claim 10, wherein the polypeptide consists of a fragment of the sequence of SEQ ID NO: 14, the fragment comprising the amino acid sequence from position 1684 to 2266 of SEQ ID NO: 14.

12. The polypeptide of claim 10, wherein the polypeptide comprises the amino acid sequence from position 1684 to 2266 of SEQ ID NO: 14 fused to a peptide or protein selected from the group consisting of FLAG, 6×His, 10×His, Influenza HA, human c-myc fragment, VSV-GP fragment, p18HIV fragment, T7-tag, HSV-tag, E-tag, SV40T antigen fragment, lck tag, α-tubulin fragment, B-tag, Protein C fragment, GST, immunoglobulin constant region, β-galactosidase and MBP.

13. A purified polypeptide consisting of a fragment of the amino acid sequence of SEQ ID NO: 14, wherein the fragment is at least 10% of the length of the sequence of SEQ ID NO: 14.

* * * * *